(12) United States Patent
Haberer et al.

(10) Patent No.: US 10,131,635 B2
(45) Date of Patent: Nov. 20, 2018

(54) COMPOSITIONS AND METHODS OF USING THE COMPOSITIONS FOR PLAQUE SOFTENING

(71) Applicant: ALUMEND, LLC, Sioux Falls, SD (US)

(72) Inventors: Barbara R. Haberer, Hartford, SD (US); Therese J. Downey, Sioux Falls, SD (US); Ronald E. Utecht, Volga, SD (US); Jeffrey E. Elbert, Waterloo, IA (US)

(73) Assignee: Alumend, LLC, Sioux Falls, SD (US)

( * ) Notice: Subject to any disclaimer, the term of this patent is extended or adjusted under 35 U.S.C. 154(b) by 0 days.

(21) Appl. No.: 14/777,248

(22) PCT Filed: Jan. 31, 2014

(86) PCT No.: PCT/US2014/014196
§ 371 (c)(1),
(2) Date: Sep. 15, 2015

(87) PCT Pub. No.: WO2014/149198
PCT Pub. Date: Sep. 25, 2014

(65) Prior Publication Data
US 2016/0046584 A1     Feb. 18, 2016

Related U.S. Application Data

(60) Provisional application No. 61/793,170, filed on Mar. 15, 2013.

(51) Int. Cl.

| | | |
|---|---|---|
| *C07D 221/14* | (2006.01) | |
| *C07D 405/14* | (2006.01) | |
| *C07D 498/18* | (2006.01) | |
| *C07D 498/22* | (2006.01) | |
| *A61K 31/473* | (2006.01) | |
| *A61K 31/4985* | (2006.01) | |
| *A61K 41/00* | (2006.01) | |
| *A61M 25/10* | (2013.01) | |
| *A61N 5/06* | (2006.01) | |
| *A61K 47/54* | (2017.01) | |
| *A61N 5/067* | (2006.01) | |

(52) U.S. Cl.
CPC .......... *C07D 221/14* (2013.01); *A61K 31/473* (2013.01); *A61K 31/4985* (2013.01); *A61K 41/0042* (2013.01); *A61K 47/545* (2017.08); *A61M 25/104* (2013.01); *A61N 5/062* (2013.01); *C07D 405/14* (2013.01); *C07D 498/18* (2013.01); *C07D 498/22* (2013.01); *A61N 2005/067* (2013.01); *Y02A 50/406* (2018.01)

(58) Field of Classification Search
CPC .. A61K 31/473; C07D 221/14; C07D 471/12; A61M 25/104

USPC ......................................................... 546/100
See application file for complete search history.

(56) References Cited

U.S. PATENT DOCUMENTS

| | | |
|---|---|---|
| 5,235,045 A | 8/1993 | Lewis et al. |
| 5,917,045 A | 6/1999 | Lewis et al. |
| 6,410,505 B1 | 6/2002 | Lewis et al. |
| 6,569,129 B1 | 5/2003 | Holmes et al. |
| 7,514,399 B2 | 4/2009 | Utecht et al. |
| 2002/0119581 A1 | 8/2002 | Daniloff et al. |
| 2002/0198385 A1* | 12/2002 | Lewis ................. C07D 221/14 546/122 |
| 2006/0182751 A1 | 8/2006 | Gazzard et al. |
| 2007/0184083 A1 | 8/2007 | Coughlin |
| 2010/0280595 A1 | 11/2010 | Bilge et al. |

FOREIGN PATENT DOCUMENTS

| | | |
|---|---|---|
| WO | 200031039 A1 | 6/2000 |
| WO | 200032577 A2 | 6/2000 |

OTHER PUBLICATIONS

Clarke et al. American Journal of the Medical Sciences, vol. 232, No. 6, 1956, p. 654-666.
Koji Suzuki et al: "Design and Synthesis of Calcium and Magnesium Ionophores Based on Double-Armed Diazacrown Ether Compounds and Their Application to Anion-Sensing Component for an Ion-Selective Electrode", Analytical Chemistry, American Chemical Society, US, vol. 67, No. 2, Jan. 15, 1995, pp. 324-334.
Jianxing Zhang et al: "Synthesis and photochemical protein crosslinking studies of hydrophilic naphthalimides", Bioorganic & Medicinal Chemistry Letters, vol. 12, No. 6, Mar. 1, 2002 (Mar. 1, 2002), pp. 853-856.
Yi Qin Gao et al: "Theoretical Investigation of the Directional Electron Transfer in 4-Aminonaphthalimide Compounds +" The Journal of Physical Chemistry A, vol. 106, No. 10, Mar. 1, 2002 (Mar. 1, 2002), pp. 1956-1960.
S. Karthikeyan et al: "Probing Strain in Thermoplastic Elastomers Using Fluorescence Resonance Energy Transfer", Macromolecules, vol. 42, No. 14, Jul. 28, 2009 (Jul. 28, 2009), pp. 5175-5178.
J.L. Meyer et al. Calc. Tiss. Res.,vol. 13, 1973, p. 295-303, abstract.
Tsuneo Ariyoshi,Kiyoyuki Eishi, Ichiro Sakamoto, Seiji Matsukuma, Tomohiro Odate: Clinical Drug Investigation Issue 4, PP Effect of Etidronic Acid on Arterial Calcification in Dialysis Patients,vol. 26, No. 4, 2006, p. 215-222.
Jianxing Zhang et al.: Journal of Biomedical Optics, vol. 9, No. 5, 2004, pp. 1089-1092, XP002726519, compounds 3-5,11.

\* cited by examiner

*Primary Examiner* — Rita J Desai
(74) *Attorney, Agent, or Firm* — Burns & Levinson, LLP; Shawn P. Foley

(57) ABSTRACT

Disclosed herein is a compound for use in a composition applied to a blood vessel, wherein the compound softens and/or disrupts the crystalline matrix of calcified plaque. Methods of treatment comprising applying the disclosed composition are also disclosed. Plaque-softening compounds are also disclosed.

18 Claims, 21 Drawing Sheets

IVUS Analysis a. Catheter artifact outlined in yellow, lumen traced in red, maximal and minimal diameters shown in light and dark blue respectively, arterial wall outlined in purple. b. Calcified plaque circled in red, acoustic shadow denoted by a red bracket.

COMPOSITIONS AND METHODS OF USING THE COMPOSITIONS FOR PLAQUE SOFTENING

CROSS-REFERENCE TO RELATED APPLICATIONS

This application is a U.S. national stage application under 35 U.S.C. 371 of international Application No. PCT/US2014/014196 filed on Jan. 31, 2014, which in turn claims priority to U.S. Provisional Application No. 61/793,170, filed on Mar. 15, 2013, both of which are incorporated by reference herein in their entirety for all purposes.

DESCRIPTION OF THE INVENTION

Field of the Invention

The present invention is directed to compounds that may disrupt the hard and crystalline structure of plaque. These compounds may be used in a composition to soften plaque. Methods of use of the disclosed compounds and/or compositions are also disclosed.

BACKGROUND OF THE INVENTION

Vascular plaque causes several medical conditions, including but not limited to, coronary artery disease, carotid artery disease, and peripheral artery disease.

Atherogenesis is the developmental process of atheromatous plaques. The build-up of an atheromatous plaque is a slow process, developed over a period of several years through a complex series of cellular events occurring within the arterial wall, and in response to a variety of local vascular circulating factors. Atheromatous plaques form in the arterial tunica intima, a region of the vessel wall located between the endothelium and the tunica media. The bulk of these lesions are made of excess fat, collagen, and elastin. At first, as the plaques grow, only wall thickening occurs without any significant narrowing. Stenosis is a late event, which may never occur and is often the result of repeated plaque rupture and healing responses, not just the atherosclerotic process by itself. Such vascular stenoses are alternatively referred to as vascular lesions.

Intracellular microcalcifications form within vascular smooth muscle cells of the surrounding muscular layer, specifically in the muscle cells adjacent to the atheromas. In time, as cells die, this leads to extracellular calcium deposits between the muscular wall and outer portion of the atheromatous plaques. The outer, older portions of the plaque become more calcific, less metabolically active and more physically rigid over time.

Two plaque types can be distinguished:

The fibro-lipid (fibro-fatty) plaque is characterized by an accumulation of lipid-laden cells underneath the intima of the arteries, typically without narrowing the lumen due to compensatory expansion of the bounding muscular layer of the artery wall. Beneath the endothelium there is a "fibrous cap" covering the atheromatous "core" of the plaque. The core consists of lipid-laden cells (macrophages and smooth muscle cells) with elevated tissue cholesterol and cholesterol ester content, fibrin, proteoglycans, collagen, elastin, and cellular debris. In advanced plaques, the central core of the plaque usually contains extracellular cholesterol deposits (released from dead cells), which form areas of cholesterol crystals with empty, needle-like clefts. At the periphery of the plaque are younger "foamy" cells and capillaries. These type of plaques are sometimes referred to as vulnerable plaques, and usually produce the most damage to the individual when they rupture, often leading to fatal myocardial infarction when present within the coronary arteries.

The fibrous plaque is also localized under the intima, within the wall of the artery resulting in thickening and expansion of the wall and, sometimes, spotty localized narrowing of the lumen with some atrophy of the muscular layer. The fibrous plaque contains collagen fibers (eosinophilic), precipitates of calcium (hematoxylinophilic) and, rarely, lipid-laden cells.

Atheromas within the vessel wall are soft and fragile with little elasticity. In addition, the calcification deposits between the outer portion of the atheroma and the muscular wall of the blood vessel, as they progress, lead to a loss of elasticity and stiffening of the blood vessel as a whole.

The calcification deposits, after they have become sufficiently advanced, are partially visible on coronary artery computed tomography or electron beam tomography (EBT) as rings of increased radiographic density, forming halos around the outer edges of the atheromatous plaques, within the artery wall. On CT, >130 units on the Hounsfield scale (some argue for 90 units) has been the radiographic density usually accepted as clearly representing tissue calcification within arteries. A carotid intima-media thickness scan (CIMT can be measured by B-mode ultrasonography) measurement has been recommended by the American Heart Association as the most useful method to identify atherosclerosis.

Intravascular ultrasound (IVUS) and optical coherence tomography (OCT) are the current most sensitive intravascular methods for detecting and measuring more advanced atheroma within living individuals. However, these imaging systems are seldom used for assessment of atheroma in view of their cost, which is not reimbursed in many medical environments, as well as invasive risks.

Angiography, since the 1960s, has been the traditional way of evaluating atheroma. However, angiography is only motion or still images of dye mixed with the blood within the arterial lumen and do not directly visualize atheroma. Rather, the wall of arteries, including atheroma with the arterial wall, generally remain invisible, with only limited shadows which define their contoured boundaries based upon x-ray absorption. The limited exception to this rule is that with very advanced atheroma, with extensive calcification within the wall, a halo-like ring of radiodensity can be seen in older patient, especially when arterial lumens are visualized end-on. On cine-floro, cardiologists and radiologists typically look for these calcification shadows to recognize arteries before they inject any contrast agent during angiograms.

Interventional vascular procedures, such as percutaneous transluminal angioplasty (PTA) for peripheral vascular disease and percutaneous transluminal coronary angioplasty (PTCA) for coronary artery disease, are typically performed using an inflatable balloon dilatation catheter to restore increased luminal diameter at the vascular lesion. During a typical PTA procedure, the dilatation catheter is positioned within the blood vessel at the location of the narrowing caused by the lesion, and the balloon is expanded with inflation fluid to dilate the vessel lumen. Following the dilatation, it is common to introduce a second balloon catheter which carries and deploys an expandable metal stent which serves to maintain vessel patency.

However, patients with calcified plaque present a much more difficult challenge for intervention. Indeed, presentation of diffuse, calcified vascular plaque within coronary arteries is often one of the most critical exclusion criteria for PTCA patient candidates, and these patients are instead required to receive invasive coronary artery bypass graft (CABG) surgery to alleviate the coronary blood flow deficiencies. On the other hand, patients presenting diffuse, calcified vascular plaque in their peripheral arteries and veins may still be eligible for PTA vascular intervention, but these patients typically require a preliminary interventional procedure involving plaque removal, such as atherectomy catheters.

In the event that an atherectomy procedure is required, the interventional physician must first deploy an embolic protection device (EPD) within the vessel being treated at a location which is distal (i.e., downstream relative to blood flow) to the atherectomy treatment site. Despite the adjunctive use of such an EPD, plaque particulates which are dislodged by the atherectomy device can occasionally escape the EPD and travel downstream within the vasculature causing a stroke, heart attack or otherwise permanently compromised distal vascular blood flow. In any event, the use of atherectomy devices produces substantial trauma to the blood vessel, and can produce serious complications such as thrombosis, as well as poor vascular healing response leading to premature restenosis.

To the extent that the interventional physician performs a PTA procedure within a blood vessel containing a lesion formed of calcified plaque, dilating such a lesion is more likely to produce increased vascular damage to the vascular tissue, such as microdissections of the vascular tissue.

It is accordingly a primary object of the invention to provide a compound, in the form of a composition, to be administered to a patient in need thereof, wherein the compound will disrupt the crystalline structure of the calcified plaque resulting in at least one of a softening of the plaque, and an increase in lumen diameter.

SUMMARY OF THE INVENTION

In accordance with the invention, there is disclosed a compound having the general formula (V):

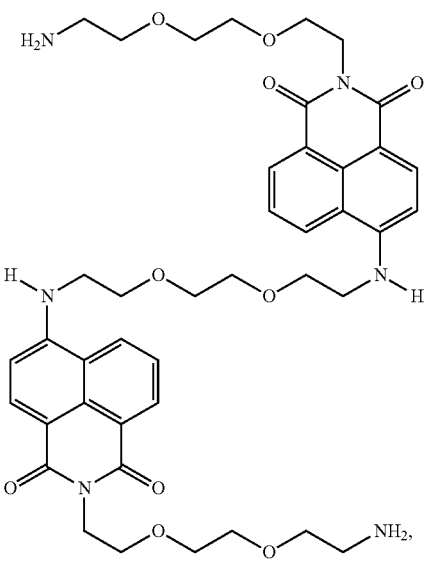

or geometrical isomers thereof.

In another aspect, there is disclosed a compound selected from the group consisting of:

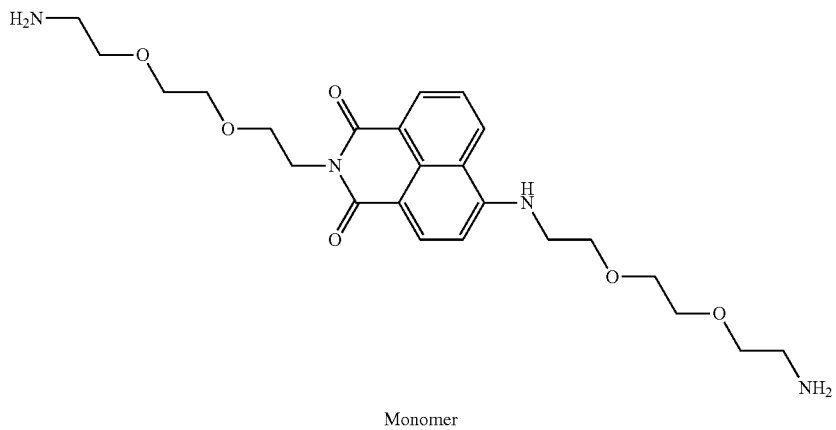

Monomer

-continued
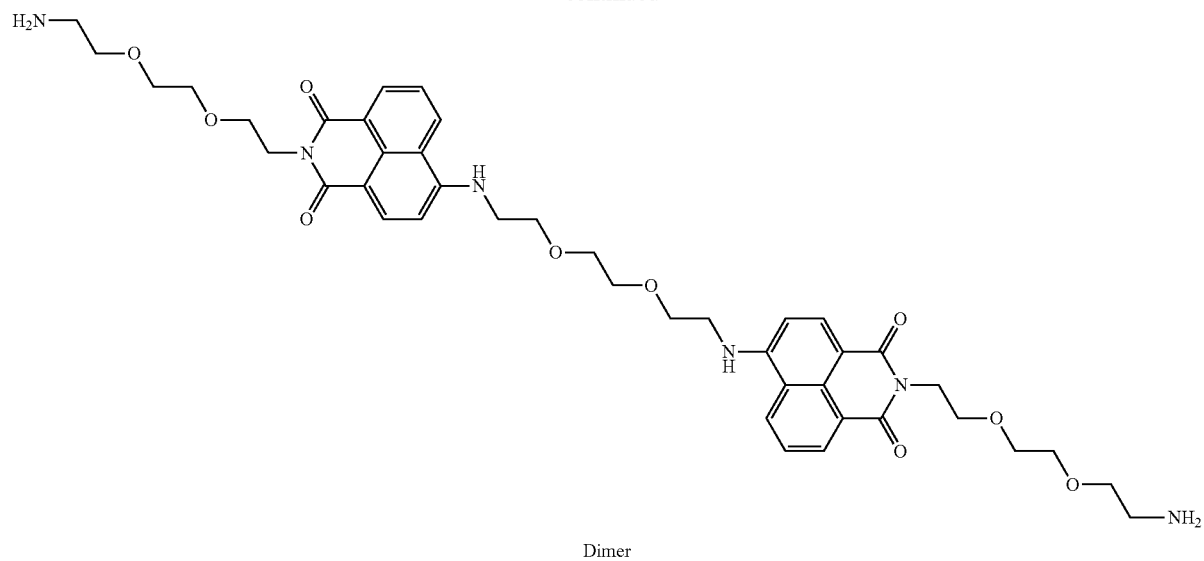
Dimer
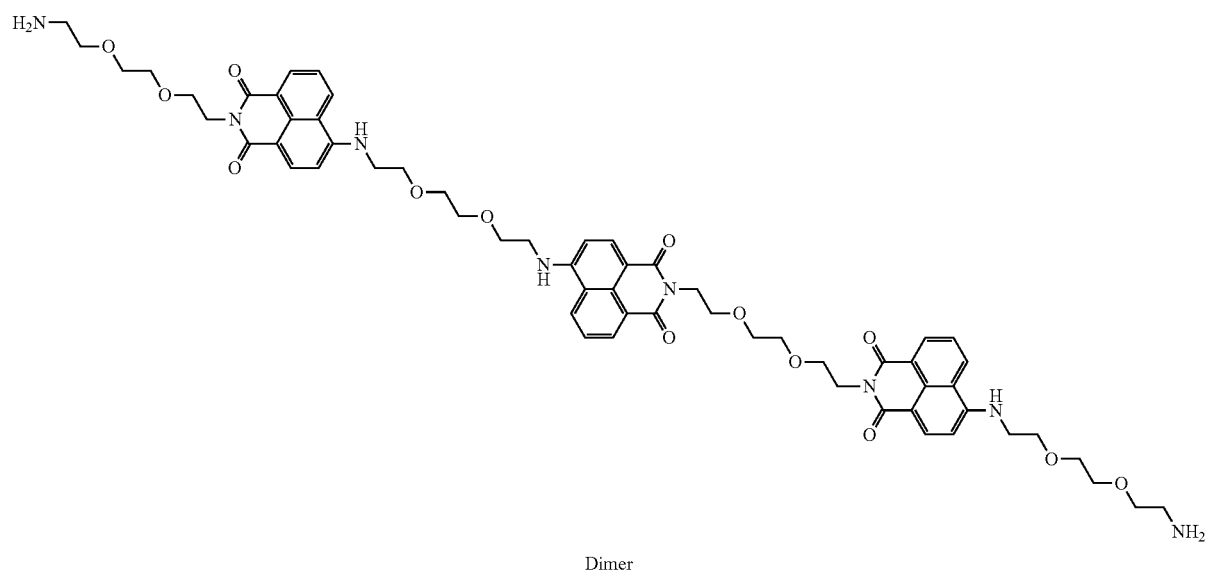
Dimer
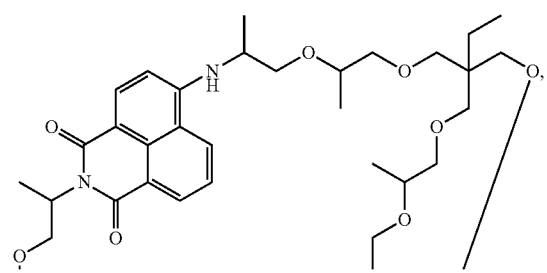

-continued

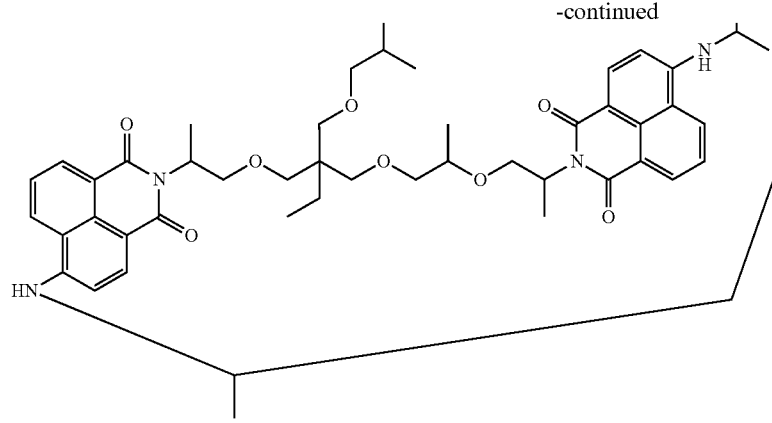

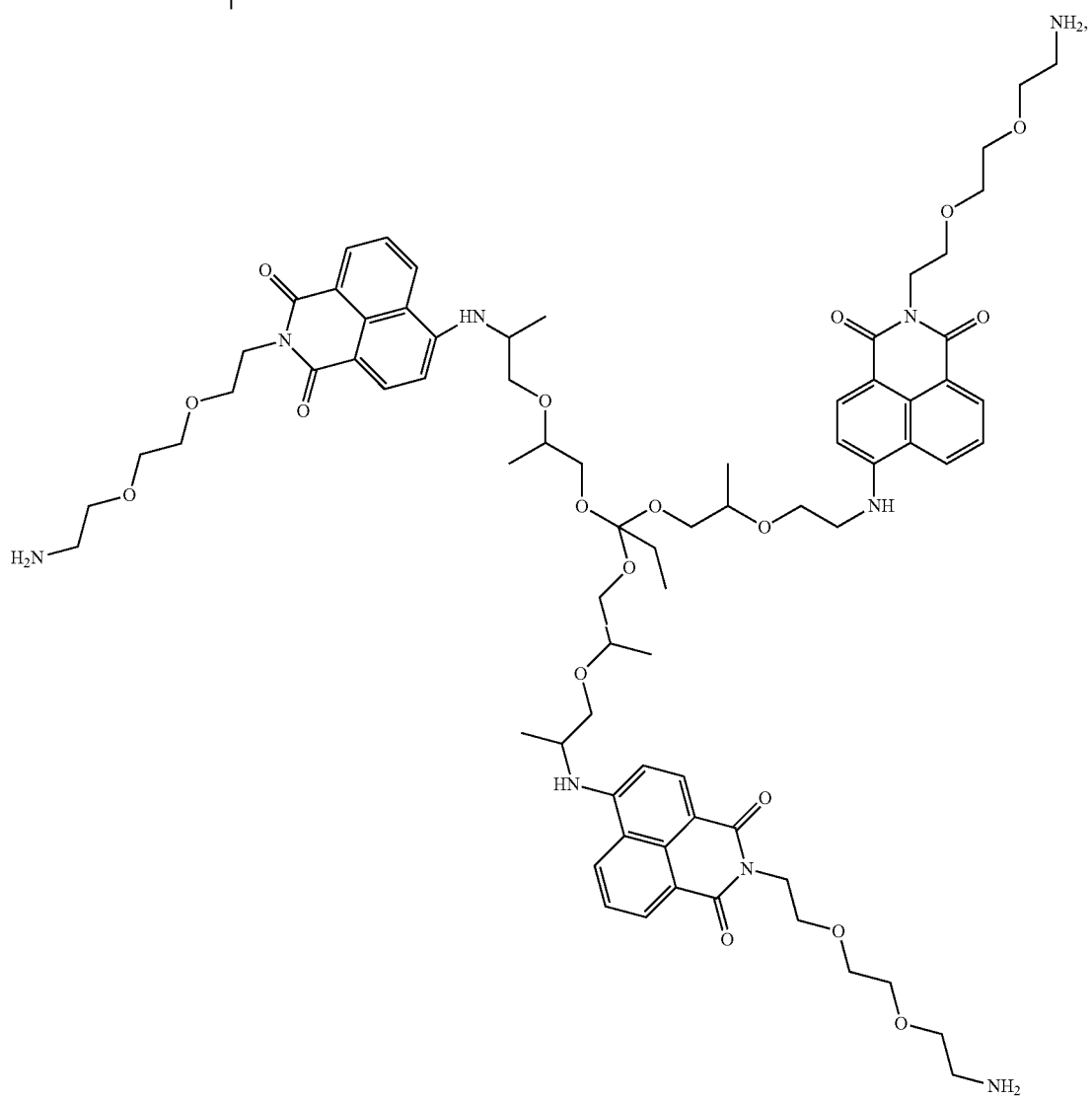

polydispersity isomers, and derivatives thereof.

In a further aspect, there is disclosed a naphthalimide compound comprising a solubilizing functional group, wherein the compound has an affinity for calcium.

There is also disclosed a method of softening plaque in a treatment zone of a blood vessel comprising a plaque matrix, the method comprising; applying a bolus of a composition comprising a plaque-softening compound to the treatment zone of the blood vessel.

In another aspect, there is disclosed a method of increasing a lumen diameter of an isolated section of a blood vessel, comprising isolating a section of the blood vessel lumen; and applying to the isolated section a plaque-softening compound, wherein the lumen area of the blood vessel is increased compared to the lumen area of a blood vessel that has not been treated with the compound.

Moreover, there is disclosed a method of tacking-up of plaque against a wall of a vessel's lumen, comprising isolating a section of vessel's lumen comprising plaque; and applying to the plaque a compound comprising at least six ethyleneoxy groups, wherein the plaque tacks-up against the wall of the vessel's lumen.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate one (several) embodiment(s) of the invention and together with the description, serve to explain the principles of the invention.

BRIEF DESCRIPTION OF THE DRAWINGS

FIGS. 4A and B are photos of an isolated section of a blood vessel comprising a plaque matrix. FIGS. 4C-D are photos of the same blood vessel after it has been subjected to angioplasty. FIGS. 4E-F are photos of the same artery after it has been treated with a plaque-softening compound.

FIGS. 5A and B are photos of an isolated section of a blood vessel comprising a plaque matrix. FIGS. 5C-D are photos of the same blood vessel after it has been subjected to angioplasty. FIGS. 5E-F are photos of the same artery after it has been treated with a plaque-softening compound.

FIGS. 6A-C are photos of an isolated section of a blood vessel comprising a plaque matrix. FIGS. 6D-F are photos of the same blood vessel after it has been treated with a plaque-softening compound.

FIG. 7A is a photo of an isolated section of a blood vessel comprising a plaque matrix. FIGS. 7B-C are photos of the same blood vessel after it has been subjected to angioplasty. FIGS. 7D-E are photos of the same artery after it has been treated with a plaque-softening compound.

DESCRIPTION OF THE EMBODIMENTS

Figure 1A:
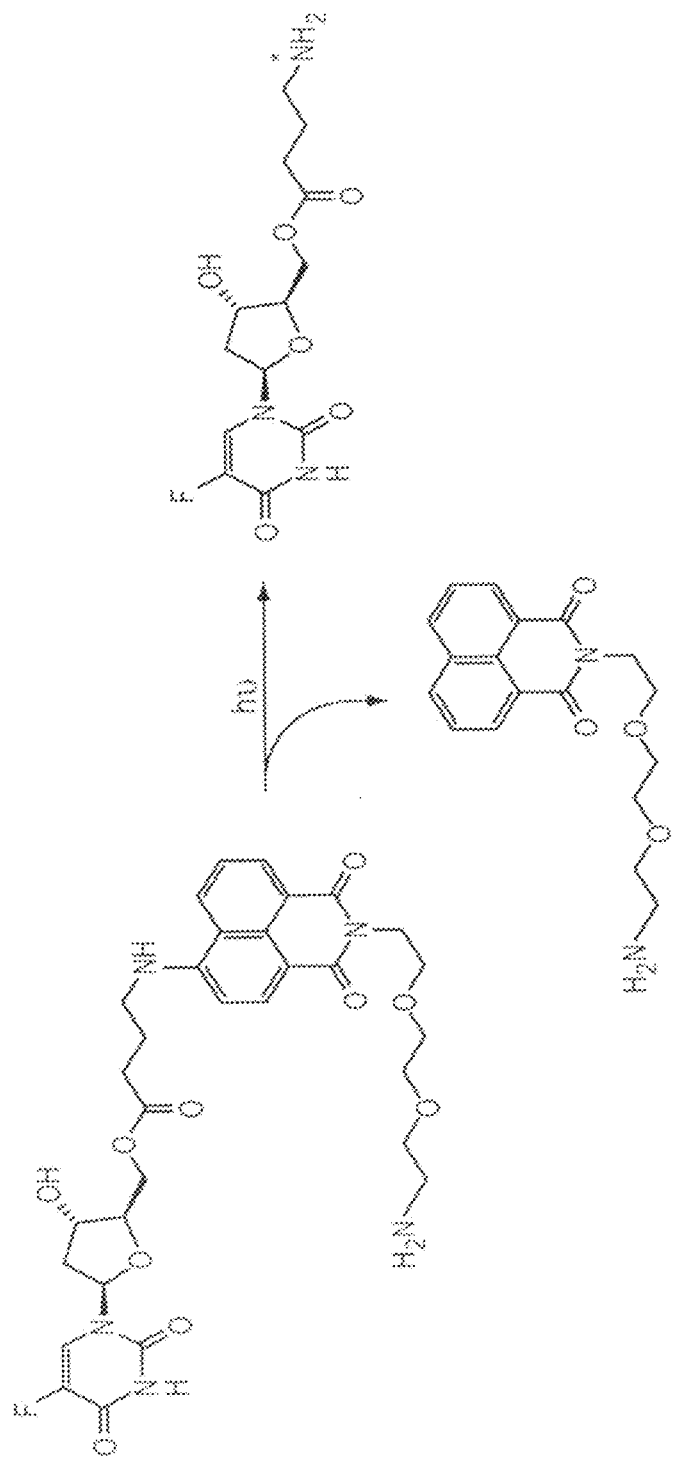
FIG. 1 illustrates an exemplary reaction scheme for tethering a pharmacological agent to a tissue, such as a blood vessel.

Reference will now be made in detail to the present embodiment(s) (exemplary embodiments) of the invention, an example(s) of which is (are) illustrated in the accompanying drawings. Wherever possible, the same reference numbers will be used throughout the drawings to refer to the same or like parts.

The present invention is directed to a naphthalimide compound comprising a solubilizing functional group. Without being bound to any particular theory, it is hypothesized that the naphthalimide compound may disrupt the crystal structure of the inorganic portion of the atheromatous plaque by introducing defects into the crystal structure thereby weakening and softening the plaque. This softening may facilitate additional compression of the plaque during treatment of the blood vessel thereby resulting in less damage to the blood vessel, which is known to be the result of hard and sharp pieces of the calcified plaque disrupted by balloon angioplasty.

The naphthalimide compound may comprise a hydrophobic component that allows the compound to penetrate the greasy portion of the plaque and access the calcium crystalline matrix. The disclosed naphthalimide compound may have a higher affinity for calcium. The structure of the disclosed compound may allow it specifically bind to calcium and other alkali earth metals. The naphthalimide compound may be a 4-amino-1,8-naphthalimide compound having a structure selected from the group consisting of:

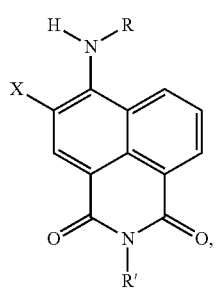

(I)

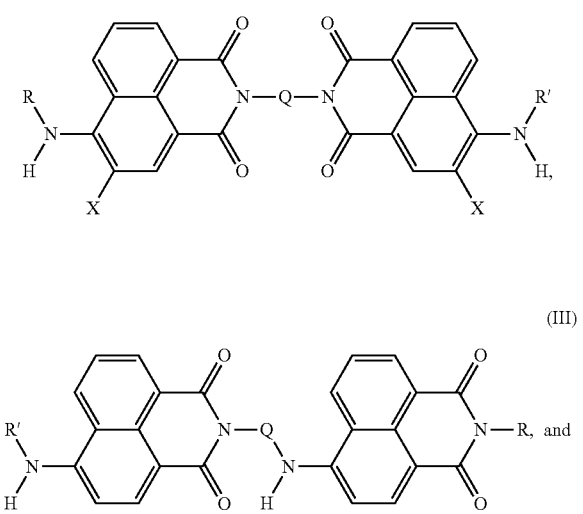

(II)

(III)

(IV)

wherein R, R', and Q are each independently selected from the group consisting of straight-chain and branched chain alkyl groups having from 2 to 200 carbons, optionally substituted with one or more ether, amide or amine groups; and wherein X is hydrogen. Naphthalimide compounds which may be used include those described in U.S. Pat. Nos. 5,235,045; 5,565,551; 5,776,600; 5,917,045; 6,410,505; 7,514,399; and 8242,114, the disclosures of all of which are hereby incorporated by reference.

In an aspect, R' can be a substituted alkyl group, wherein the alkyl group is substituted with heteroatoms, such as N, O, P, and S or halogens, such as F, Br, Cl, or I. In another aspect, R' can include an amine, a carboxylate, a phosphate, and/or a sulfate.

In an aspect, Q is a polyethylene moiety. Moreover, Q can be a moiety that contains amines and carboxyl groups arranged in a fashion reminiscent of EDTA-like ligands, phosphate groups and/or organic acids arranged in a fashion able to interact with calcium, or functional motifs able to interact with calcium such as luciferin.

In another aspect, Q is an acid or an alcohol, but can also be a thioester, an organophosphorous ester, an anhydride, an amide, a carbamate, or an urea. In order to covalently bond to In another aspect, the naphthalimide compound has the following structure:

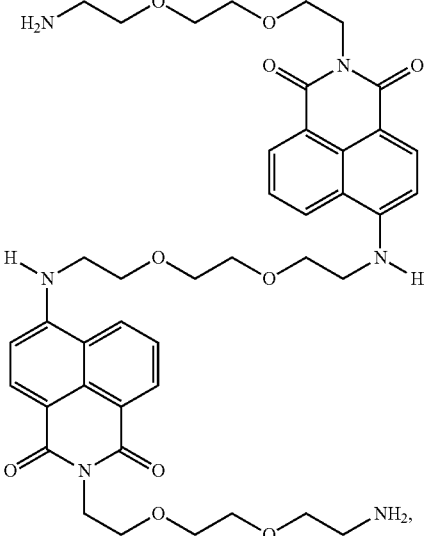

and can include its geometric isomers.

It is hypothesized that upon photoactivation the polyethylene moiety linking the two naphthalimides becomes an intermediate with photoactivated terminal amines. This intermediate has an affinity for binding to amino acid residues on biological molecules, and forms the linkage via a condensation reaction. In particular, the naphthalimide may have a higher affinity for linear protein structures such as collagen or elongated elastin when compared to globular proteins, such as albumin, because the constant twisting and turning of the backbone pulls the hydrogen bonds "out of phase". Moreover, the dimer, shown above, penetrates plaque easily and the diffusion rate is minimally constrained The polyether moieties attached in the imide positions impart solubility and the naphthalimide rings are for photoactivation. The solubilizing tails are also believed to mimic a crown ether effect present in known chelating agents. Thus, it is believed that these solubilizing tails would have the ability to penetrate the crystalline regions and disrupt the structure that makes the plaque hard and sharp. To be clear, however, there is a balancing act to be achieved between solubility and diffusion that must be considered in formulating compounds for use in the present invention.

Below are some additional compounds including a monomer, dimer, and trimer of naphthalimide rings. Polymers and derivatives of the compounds below are also contemplated.

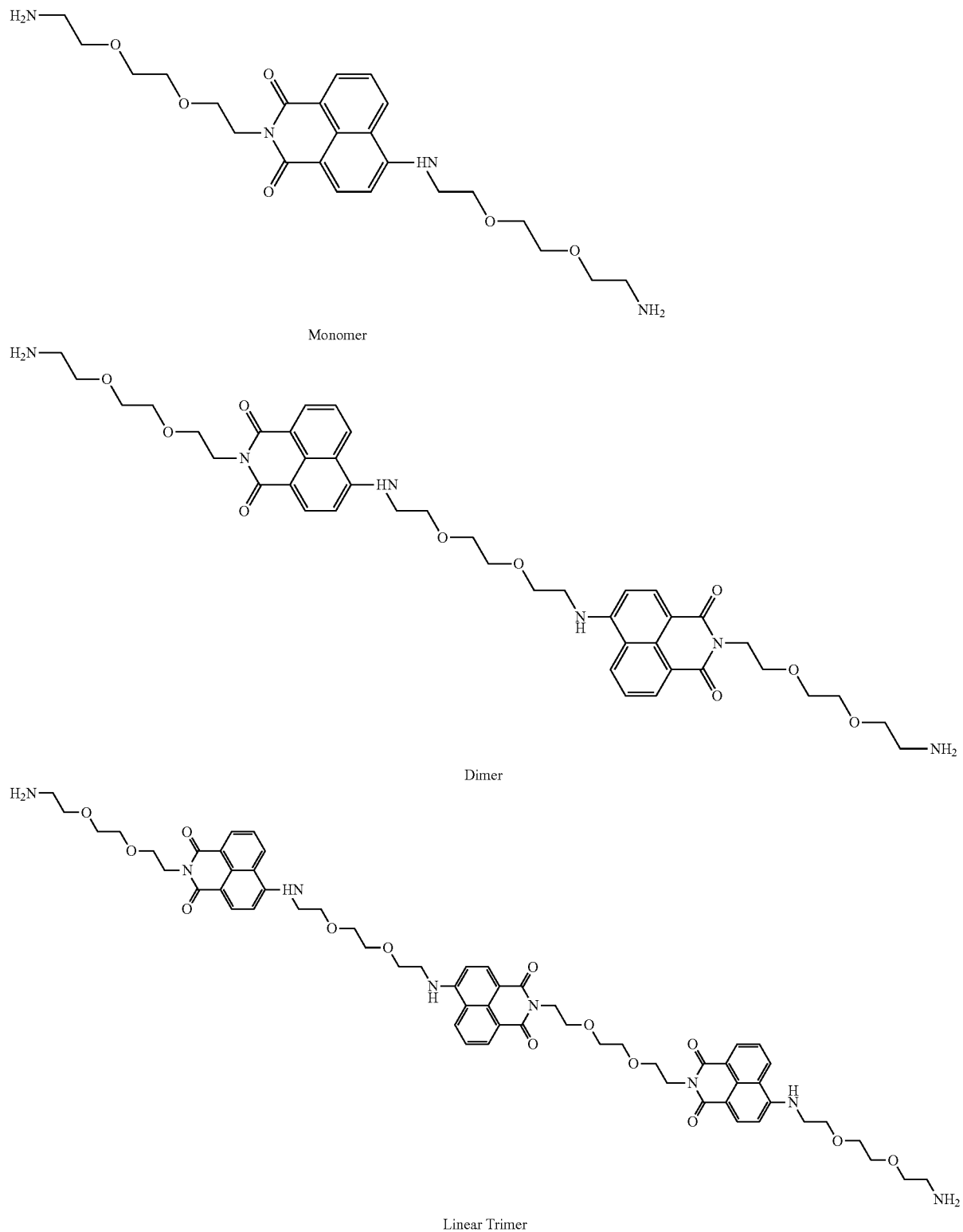 [SMILES: NCCOCCOCCNc1ccc2c3c(cccc13)C(=O)N(CCOCCOCCN)C2=O ; NCCOCCOCCN1C(=O)c2cccc3c(NCCOCCOCCNc4ccc5c6c(cccc46)C(=O)N(CCOCCOCCN)C5=O)ccc(c23)C1=O ; NCCOCCOCCNc1ccc2c3c(cccc13)C(=O)N(CCOCCOCCN1C(=O)c3cccc4c(NCCOCCOCCNc5ccc6c7c(cccc57)C(=O)N(CCOCCOCCN)C6=O)ccc(c34)C1=O)C2=O]
Monomer
Dimer
Linear Trimer
The dimeric structure of the disclosed naphthalimide compound is designed to lie along the extended backbone of the collagen helix as shown below.

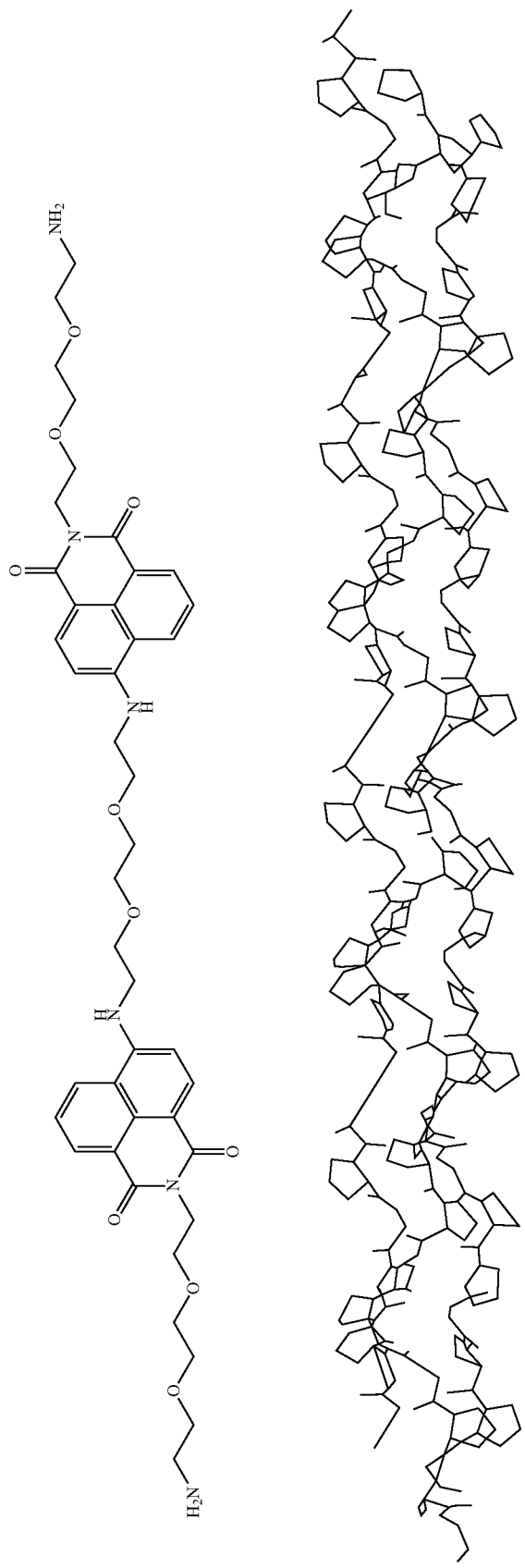

In considering alternative compounds for use in the disclosed composition, it is noted that as molecules get longer, at some point the strong hydration associated with the terminal amines and the weaker hydration associated with the oxygen atoms will fail to overcome the insolubility of the greasy naphthalimide and the naphthalimide will be insoluble and therefore not useful. In particular, as the molecule becomes longer and therefore more "greasy" it will more likely stick to one collagen molecule and not span the gap between two collagen molecules. For this reason, linear trimers, such as exemplified above, may not be preferred.

In order to overcome the challenges of longer compounds, like a linear trimer, a "capped" trimer, as shown below, comprising no terminal amines and the polyethylene groups have been changed to polypropylene groups may be used. This molecule may have a smaller hydrodynamic radius and it may be more hydrophobic. This may present an advantage in faster diffusion and an ability to penetrate plaque more effectively. The downside may be reduced water solubility.

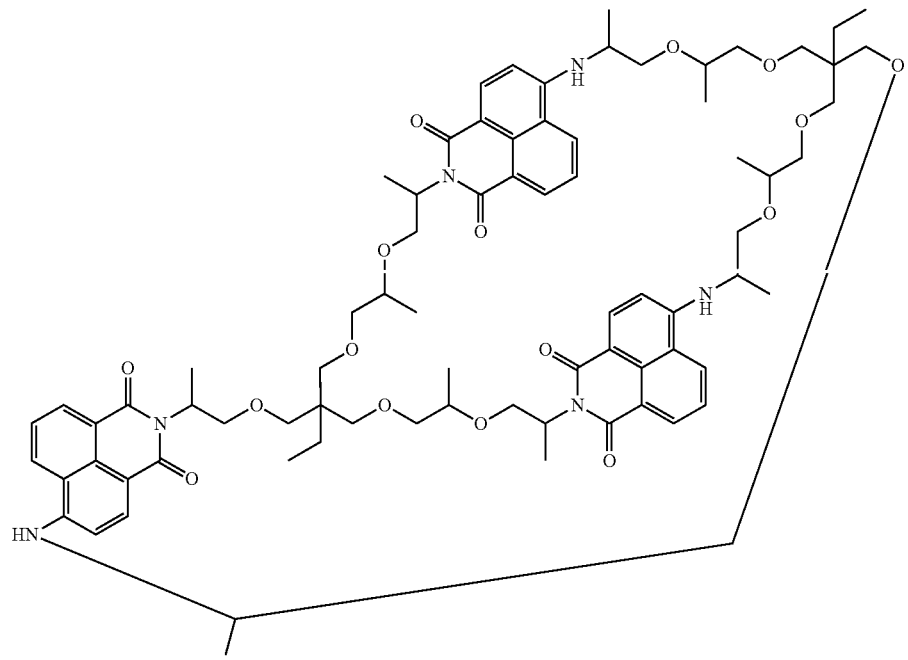 [SMILES: CCC12COCC(C)Nc3ccc4c5c(cccc35)C(=O)N(C4=O)C(C)COCC(CC)(COCC(C)OCC(C)N3C(=O)c4cccc5c(ccc(c45)C3=O)NC(C)COC(C)COC1)COCC(C)OCC(C)N1C(=O)c3cccc4c(ccc(c34)C1=O)NC(C)COC(C)COC2]

A "starred timer" having three terminal amines, but not in a linear arrangement can be used as a compound of the invention. In addition, it is believed that this design increases the likelihood of linking with collagen molecules. This behavior is not obvious from the monomer and dimer structures. Derivatives and polydisperse isomers of the compound below are also contemplated.

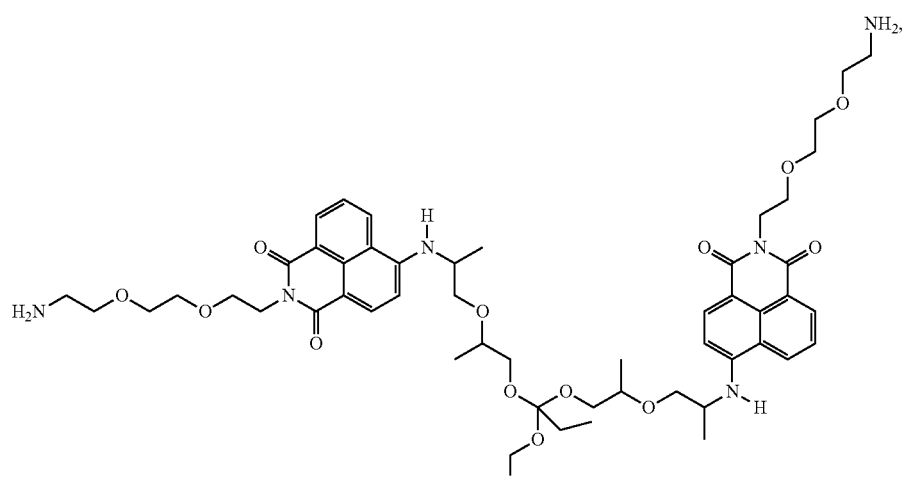

-continued

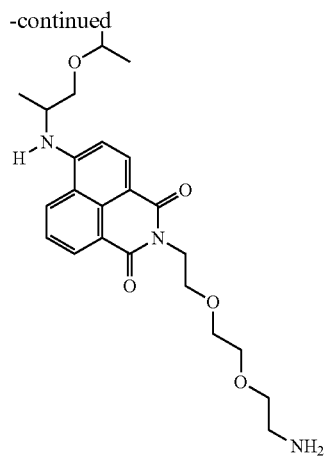

Figure 14:
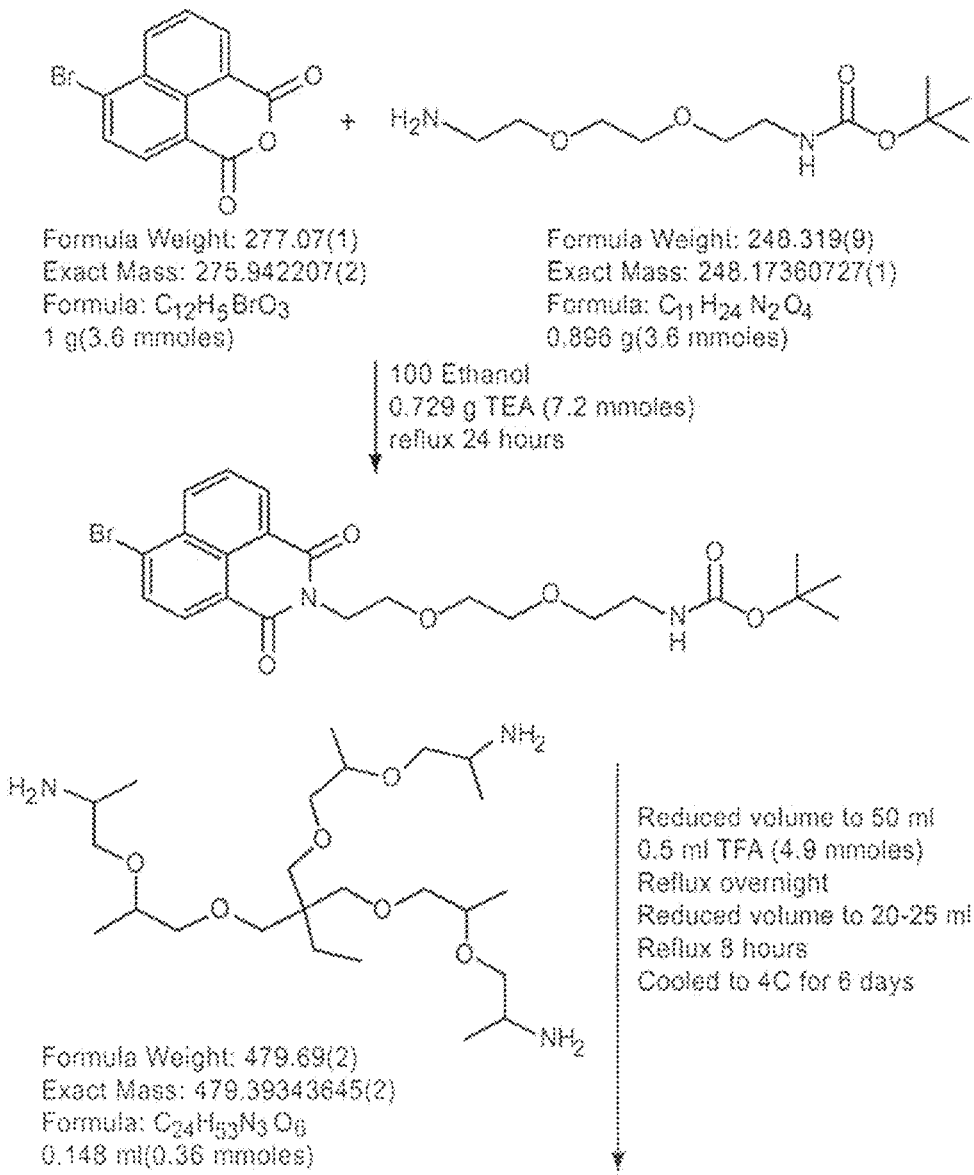
FIG. 14 is an exemplary reaction scheme for the formation of a starred naphthalimide trimer.
Figure 14:
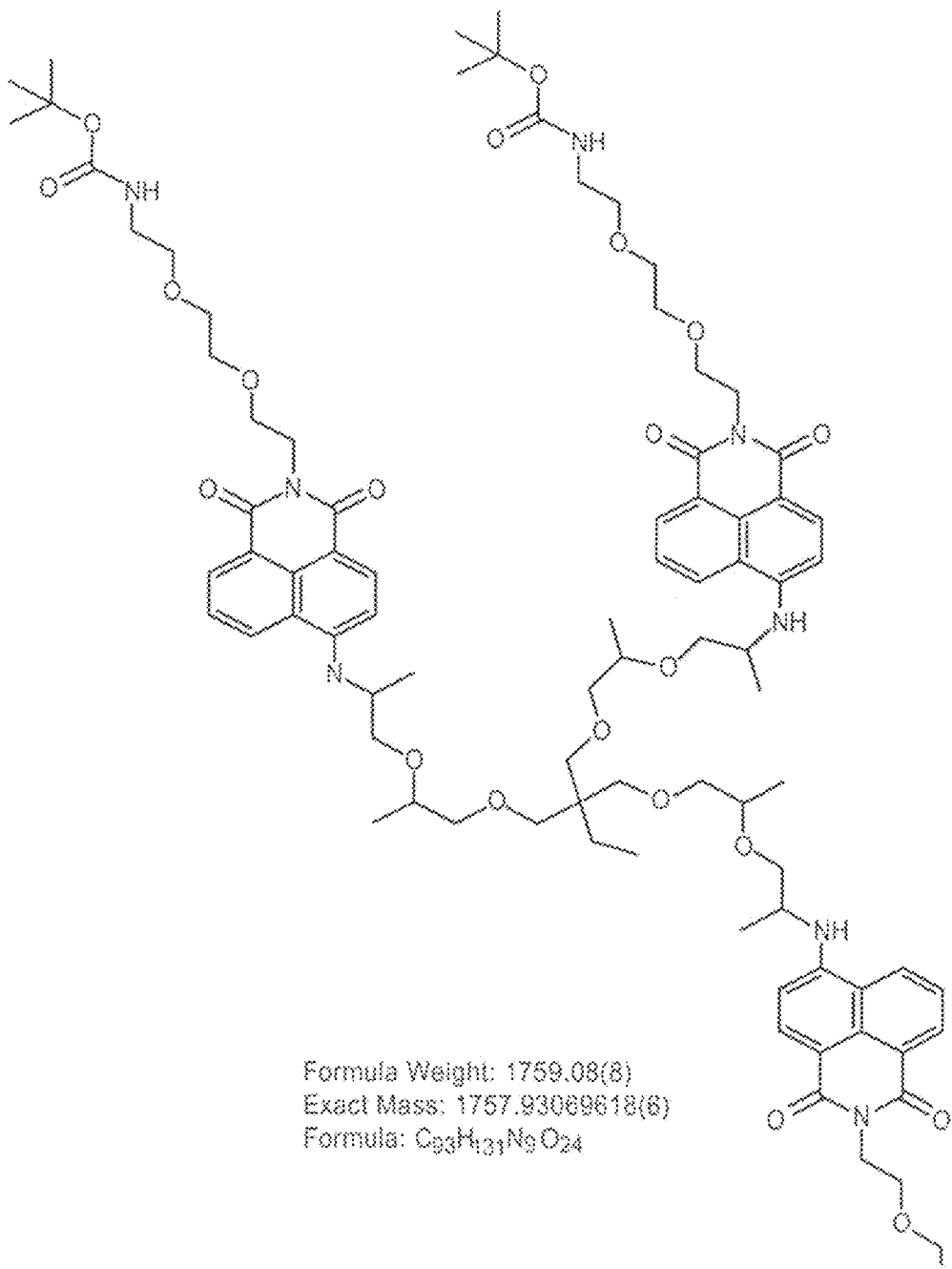

The "starred" trimer is designed to overcome any intramolecular links that may form between the compound and the collagen matrix. The center group of the linker retains the polyether functionality but the branched nature and additional methyl groups may reduce the tendency of the linker to hydrogen bond to the collagen backbone while retaining the ability to associate with water. These characteristics may increase the likelihood of collagen intermolecular bonds and thereby increase the effectiveness of the compound. FIG. 14 illustrates a possible synthetic pathway for creation of the starred trimer shown above.

The "starred timer" extending along a collagen matrix is shown below. With this compound, the water solubility might be lower, the compound may have a longer reach inside a blood vessel, may be more effective in penetrating plaque, may provide improved structural reinforcement to a blood vessel, the diffusion rate might be slower or the preferential localization with collagen might be lower. Derivatives of the compound below are also contemplated.

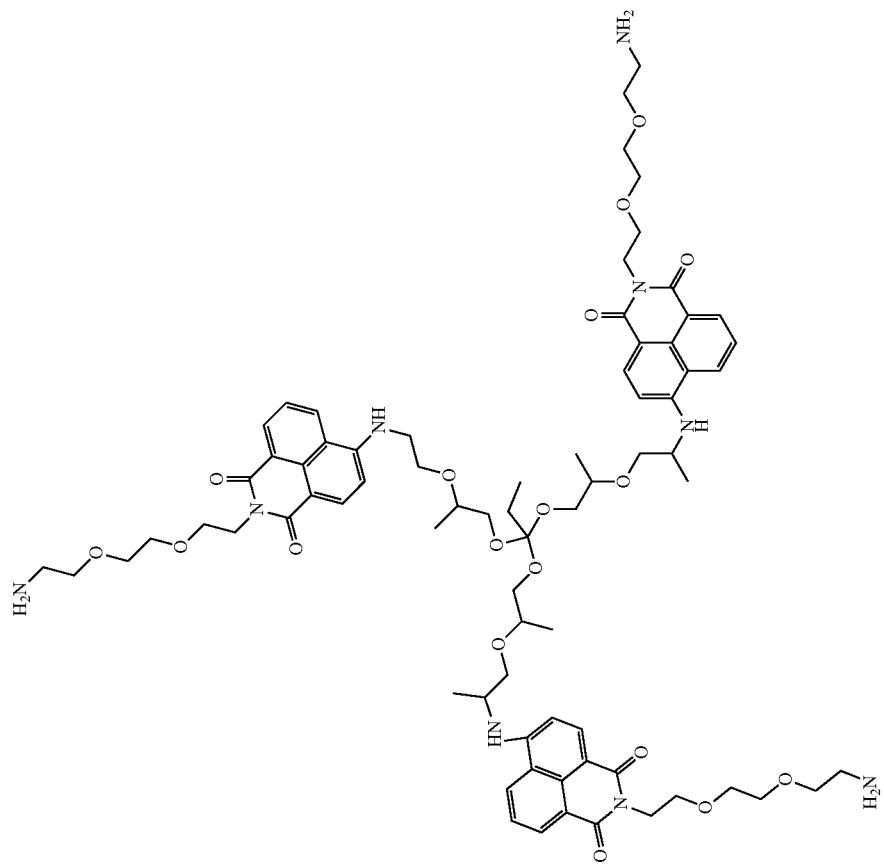
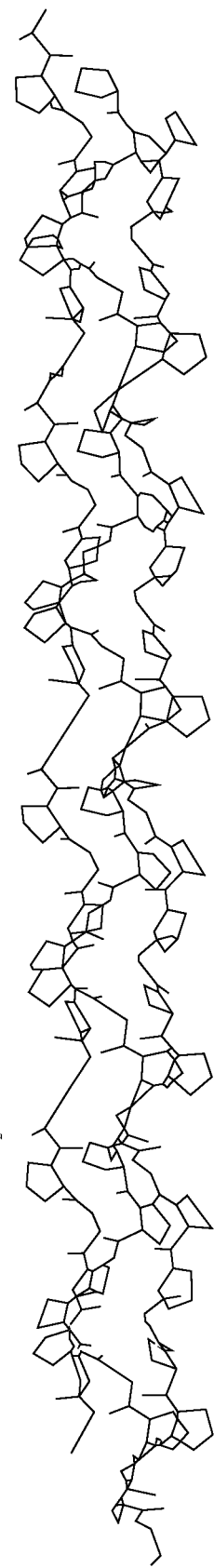

Compounds other than the naphthalimide compounds disclosed above and their derivatives are also contemplated for use in a composition. In particular, compounds that possess functional groups that allow for water solubility, increased tissue diffusion, and calcium solubilization are considered useful for the present invention. Exemplary compounds, include but are not limited to, EDTA-like ligands, luciferin based ligands, polyether ligands, phosphate based ligands, and organic acids.

Ethylenediaminetetraacetic acid (EDTA) is a member of the polyamino carboxylic acid family of ligands. EDTA binds to metals in a hexadentate fashion with an octahedral geometry. Numerous variants of this basic structure have been used by chelating agents with various affinities for different metals, such as calcium. Examples of compounds having a basic structure similar to EDTA, include but are not limited to, ethylene glycol tetraacetic acid (EGTA); diethylene triamine pentaacetic acid (DTPA); 1, 2-bis[o-aminophenoxy)ethane-N,N,N'N'-tetraacetic acid (BAPTA); and Amino-5-(3-dimethylamino-6-dimethylammonio-9-xanthenyl)phenoxy]-2-(2-amino-5-methylphenoxy)ethane-N,N,N',N'-tetraacetic acid. EDTA is completely hydrophilic and it is expected that it cannot penetrate the greasy portion of plaque. Moreover, a relatively low binding constant (10.69 log $K_f$) between EDTA and calcium renders it unlikely that EDTA would be capable of removing calcium from plaque in a blood vessel.

Additional compounds, known for their use in fluorescence imaging, can be used and comprise four carboxylic acid functional groups, such as Fura 2 ($C_{29}H_{22}N_3O_{14}^{5-}$), which binds to free intracellular calcium; Fura 2-AM ($C_{44}H_{47}N_3O_{24}$); Fluo 3 ($C_{36}H_{30}Cl_2N_2O_{13}$); Fluo3-AM ($C_{51}H_{50}Cl_2N_2O_{23}$); Indo 1 ($C_{32}H_{31}N_3O_{12}$); Indo 1-AM ($C_{47}H_{51}N_3O_{22}$); Quin 2 ($C_{26}H_{23}K_4N_3O_{10}$); and Rhod 2-AM ($C_{52}H_{59}ClN_4O_{19}$). These compounds are available from suppliers such as Donjindo Molecular Technologies. The conjugated aromatic group provides a fluorescence. The added aromatic group teaches that changes can be made to the structure of the compound without compromising the ability to soften plaque. Moreover, these groups are inherently greasy and therefore lipid soluble, which may provide the ability to penetrate tissue.

Coelenterazine-WS, a luciferin based ligand, is an additional compound that can be used and is also supplied by Donjindo Molecular Technologies.

A suitable polyether ligand for use as a compound in the present invention may be Calcium ionophore V-Selectophore® (10,19-Bis[(octadecylcarbamoyl)methoxyacetyl]-1,4,7,13,16-pentaoxa-10,19-diazacycloheneicosane), as shown below. This particular compound has long chain alkyl groups attached that provide lipid solubility allowing the compound to transport calcium across cell membranes.

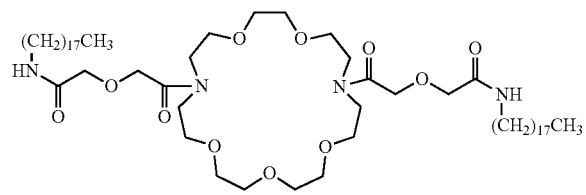

Variants of the crown ether motif have been reported by Gatto et al, II, J.A.C.S., vol. 106, No. 26, pp. 8240-8244 (1984) and Capel-Cuevas, et al, Talanta, Vol 78, pp. 1484-1488 (2009). These reports demonstrate that both the substituents as well as the constituent chalcogen can be varied and still provide the ability to chelate calcium.

Phosphate based ligands, such as phosphonates or phosphonic acids, have been used to chelate calcium to prevent scale in water systems. Some exemplary compounds that may be useful as compounds in the present invention, include but are not limited to, etidronic acid (INN) or 1-hydroxyethane 1,1-diphosphonic acid (HEDP); aminotris (methylenephosphonic acid) (ATMP); ethylenediamine tetra (methylene phosphonic acid) (EDTMP) (a phosphonate analog of EDTA); and diethylenetriamine penta(methylene phosphonic acid) (DTPMP).

Organic acids suitable for use as a compound of the present invention include, but are not limited to, citric acid and dipicolinic acid (pyridine-2,6-dicarboxylic acid or PDC).

Common chelating agents include desfuroxamine mesylate (used for iron toxicity, dimercaprol (BAL) (lead, preferred for arsenic and mercury), DMSA—an analogue of dimercaprol (given for lead and arsenic), D-penicillamine (for lead, arsenic, or mercury), and calcium disodium versante (CaNa2-EDTA). However, these compounds are generally used to chelate metals other than calcium, and may not have the requisite chemical structure to be water soluble and penetrate tissue, as needed by compounds of the present invention.

It is hypothesized that the compounds disclosed herein can soften plaque, such as calcified plaque, due to the disruption of the crystalline lattice. This disruption should be noticeable in, for example, known imaging techniques, such as IVUS and OCT. In particular, in IVUS imaging the disruption in the crystalline lattice should result in lower echogenicity producing a less intense reflection, and an increase in the hypo-echogenic reflection at the expense of the hyper-echogenicity reflections.

One of ordinary skill in the art would readily be able to determine if plaque has been softened and/or modified following treatment with a plaque-softening compound as disclosed herein. In an aspect, one of ordinary skill in the art can visualize whether the artery is more flexible after treatment. In another aspect, one of skill could attempt to manipulate the blood vessel to see if it resists manipulation before and after treatment. A blood vessel that is more easily manipulated after treatment would be understood to have had its plaque softened. As an example, one could measure the outward radial movement associated with compression forces generated by the inflatable balloon angioplasty to which the plaque is in apposition therewith. Alternatively, one could attempt to manipulate the blood vessel by bending it with a forceps. In a further aspect, "plaque softening" means increasing the hypo-echogenicity of a blood vessel following treatment of the blood vessel with the disclosed plaque-softening compounds. An increase in hypo-echogenicity could be determined using IVUS. In another aspect, "plaque-softening" means modifying the calcific nature of the native plaque matrix by, for example, disrupting the crystalline lattice or solubilizing calcium compounds within the plaque matrix.

Calcified plaque is not homogeneous and may comprise different types of calcium compounds, such as calcium oxalate and calcium phosphate, which have differing degrees of solubility. It is possible that the disclosed plaque-softening compounds can more easily penetrate into regions of plaque that are more soluble, such as calcium oxalate, and penetrate to a lesser degree regions of plaque that are more insoluble, such as calcium phosphate. For this reason, an area of plaque in a diseased blood vessel that is treated with a disclosed plaque-softening compound may not uniformly soften the plaque.

In an aspect, there is disclosed a complex that can be used for sustained, localized delivery of a pharmacological agent. The complex can comprise a naphthalimide compound having a solubilizing tail, a tether/linker, and a pharmacological agent. In an aspect, the pharmacological agent can be attached via a tether/linker to the naphthalimide compound. Upon activation by an activating agent, the amino group containing the tether/linker and pharmacological agent can be controllably released in an active form that will bond to tissues localizing the delivered pharmacological agent on a targeted tissue.

In an aspect, the nitrogen of the 4-amino group connected to the tether can attach to the tissue after activation by an activating agent. The activating agent can be selected from radiated energy, electromagnetic energy, laser, electric current, electrons, thermal neutrons, and chemicals. The tether and pharmacological agent will remain covalently attached to the tissue, likely collagen until such time that the collagen is turned over. Hydrolysis of the ester linkage will result in the release of the pharmacological agent.

To be clear, the pharmacological agent can be released over time depending on hydrolytic cleavage, photolysis cleavage, enzymatic cleavage, or a combination thereof of the pharmacological agent from the tether/linker. The localization, solubility, and release profile of the pharmacological agent can be tailored by selection of the appropriate tether/linker. Alternatively, the tether/linker and pharmacological agent can be attached together in a manner so that a cleavable bond does not result, thereby creating a permanent tether to the tissue.

Figure 1B:
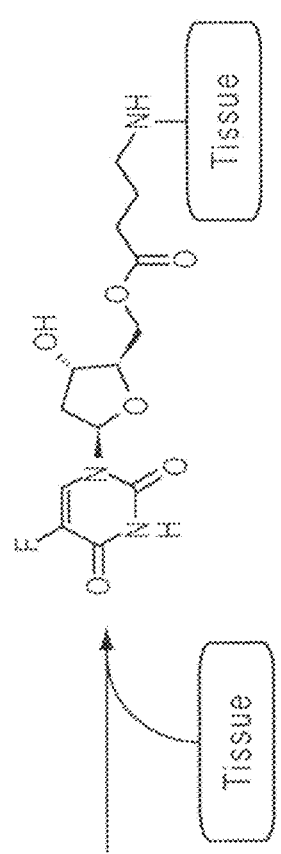
Figure 1C:
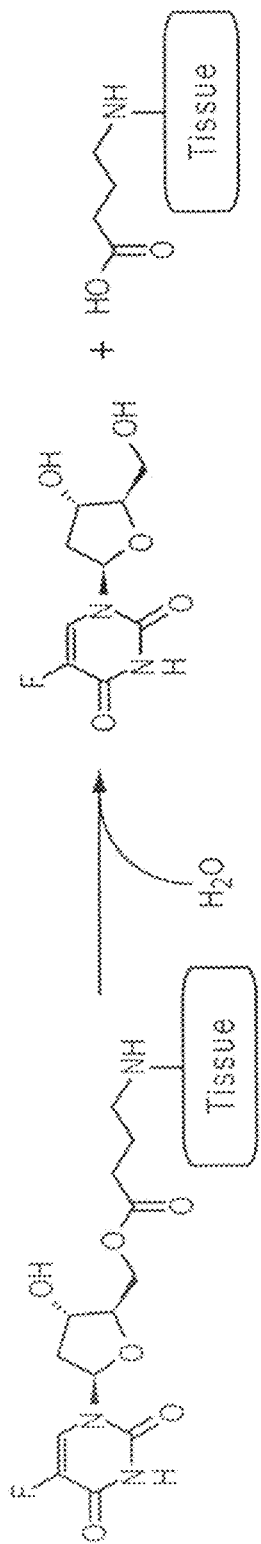

An exemplary complex is shown in Step A) of FIG. 1. The complex can comprise a pharmacological agent, such as Floxuridine (5-fluorodeoxyuridine) covalently bonded to a hydrolysable linker (GABA, gamma-aminobutyric acid) attached to a naphthalimide compound having a solubilizing tail. In step A) upon light activation by an activating agent, the naphthalimide compound provides a reactive site (N*) on the GABA linker connected to the pharmacological agent. The naphthalimide compound and its tail are released. In step B) in a subsequent dark reaction, the reactive species attaches to the target tissue thereby localizing the pharmacological agent to the target tissue. In step C), an ester functional group located between the GABA linker and the pharmacological agent can hydrolyze thereby releasing the pharmacological agent in its native configuration. In this particular example, the GABA linker can provide a rate constant that is projected to provide a half life of 4-5 days.

Any of the disclosed naphthalimide compounds and alternative plaque-softening compounds can be used as part of the complex used for localized delivery of a pharmacological agent.

As disclosed herein, the naphthalimide compound can comprise a solubilizing tail attached thereto. By thoughtful selection of the solubilizing tail, one of ordinary skill in the art can control the localization of the pharmacological agent. In an aspect, a hydrophilic functional group, such as a polyether functionality, for use as the tail can increase the solubility of the pharmacological agent and can direct the localization to collagen rich regions of tissue. A complex comprising a hydrophilic tail can easily enter the luminal side of a blood vessel wall and penetrate into the media. Alternatively, a complex comprising a hydrophobic tail can encounter a luminal barrier and therefore be excluded from the media.

The purposeful design of the covalent bond (e.g., ester, carboxyl, etc.) between the tether/linker and the pharmacological agent can be used to tailor delivery to specific treatment areas. An important consideration in the choice of the tether/linker is the relationship between the structures and the hydrolysis rate. For example, one of ordinary skill in the art can select a pharmacological agent that will form an ester linkage with a particular tether/linker. The hydrolysis rate of the ester linkage can then be determined. Depending upon the particular hydrolysis rate of the ester linkage, one of ordinary skill in the art could then introduce other derivatives of the tether/linker and/or pharmacological agent to determine the effects on the hydrolysis rate. By slightly altering the functional groups on the tether/linker, one of ordinary skill in the art would be able to determine the appropriate hydrolysis rate for the covalent bond between the tether/linker and pharmacological agent that would be suitable for the localization to the target tissue. For example, one of ordinary skill in the art could formulate a tether/linker library identifying tethers/linkers with hydrolysis release rates, e.g., $t_{1/2}$=3 days (0.01 $hr^{-1}$), $t_{1/2}$=7 days (0.004 $hr^{-1}$), $t_{1/2}$=14 days (0.002 $hr^{-1}$), $t_{1/2}$=28 days (0.001 $hr^{-1}$). The idea of creating a "linker library" with various linker structures and their known and/or expected hydrolysis rate and correlating that information to other similarly structured linker compounds to determine their hydrolysis rates is more fully explained in Example 28.

In an aspect, the hydrolysis release rate can be varied by simply adding electron withdrawing substituents in the form of halogens in order to influence the behavior of the ester functional group. The hydrolytic behavior of esters is highly dependent on their electronic structure and steric bulk. An increase in the electron withdrawing tendency leads to reaction rates that are substantially higher.

In another aspect, the hydrolysis rate can be varied by the functional groups present on the tether/linker. Table 1 describes six possible tethers with anticipated hydrolysis rates that vary from slow to fast.

TABLE 1

Structure and anticipated hydrolysis rates of linkers.

| # | Linker Structure | Source of Linker | Anticipated Cleavage Rate | Increasing Rate Of Hydrolysis/Faster Drug Delivery |
|---|---|---|---|---|
| 1 | 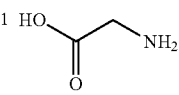 | Linker available from Sigma-Aldrich Glycine | slow | |

TABLE 1-continued

Structure and anticipated hydrolysis rates of linkers.

| # | Linker Structure | Source of Linker | Anticipated Cleavage Rate | Increasing Rate Of Hydrolysis/Faster Drug Delivery |
|---|---|---|---|---|
| 2 | HO-C(=O)-CH2-CH2-NH2 | Linker available from Sigma-Aldrich 3-Amino-propionic acid | slow | |
| 3 | HO-C(=O)-CH2-S-CH2-CH2-NH2 | In situ generated | Expected $t_{1/2}$~15 days Good for 30 day release | |
| 4 | HO-C(=O)-CH(OH)-CH2-NH2 | Linker available from Sigma-Aldrich 3-amino-2-hydroxy-propionic acid | | |
| 5 | HO-C(=O)-S-CH2-NH2 | In situ generated | Expected $t_{1/2}$~4 days Good for 7 day release | |
| 6 | HO-C(=O)-O-CH2-NH2 | In situ generated | fast | |

Compounds 1 and 2 are expected to form simple ester. These esters are expected to hydrolyze only slowly at physiological pH. In the unlikely situation that the local environment increases the hydrolysis rate to a level where the pharmacological agent is delivered too quickly, these tethers could be used to slow that rate.

There is little guidance on the release rates for esters under physiological conditions as hydrolysis has been explored primarily under acidic or basic conditions. Release rates with a glycine linker are consistently faster than a GABA linker possibly due to the autocatalytic formation of a 5-membered ring intermediate with the glycine linker. It is expected that a GABA linker will provide a hydrolysis release rate that would deliver about 80% of a pharmacological agent over a one-week period (2-3 half-lives).

Compound 3 has an electron withdrawing substituent near the carboxylic acid which will become part of the ester targeted for hydrolytic cleavage. The electron withdrawing group will speed the reaction when compared to the simple esters formed from compounds 1 and 2. This tether can be synthesized as part of the complex in situ before attachment to a pharmacological agent, such as Everolimus. Literature reports show a hydrolysis rate that is well suited to a 30 day delivery. The full structure of this conjugate is shown below including the solubilizing tail.

Compound 4 has additional electron withdrawing characteristics when compared to compound 3. This can provide a rate of hydrolysis that is somewhat faster than compound 3 and represents an example to tailor the release rates.

Compound 5 has a structure that is even more susceptible to hydrolysis and can provide a faster rate of release. This tether can be synthesized as part of the complex in situ before attachment to a pharmacological agent. Literature reports show a hydrolysis rate that is well suited to a 7 day delivery.

Of the compounds shown in Table 1, compound 6 will have the fastest release rate, likely too fast for a seven day delivery but represents a possible structure if the local environment stabilizes the ester and release rates are unexpectedly slow.

As discussed above, the tether/linker forms a hydrolysable covalent bond with a pharmacological agent. The pharmacological agent for use in the complex can be any agent that will form a covalent bond, i.e., a hydrolysable bond, with the disclosed tether/linker. Like the tether/linker, the pharmacological agent can also be selected to include functional groups that would affect the hydrolytic release rate from the tether/linker.

In an aspect, the pharmacological agent may be any agent comprising at least one hydroxyl or carboxylic acid functional groups. Hydroxyl functional groups on the pharmacological agent can be the target for attachment to the tether/linker via an ester linkage. Exemplary pharmacological agents comprising at least one alcohol functional group, include but are not limited to, paclitaxel, everolimus, sirolimus, zotarolimus, and biolimus. For example, both everolimus and sirolimus have a readily available reactive alcohol in the 40-position that is a good synthetic target for attachment. Similarly, both zotarolimus and biolimus have a readily available alcohol functional group in the 28-position.

Figure 2A:
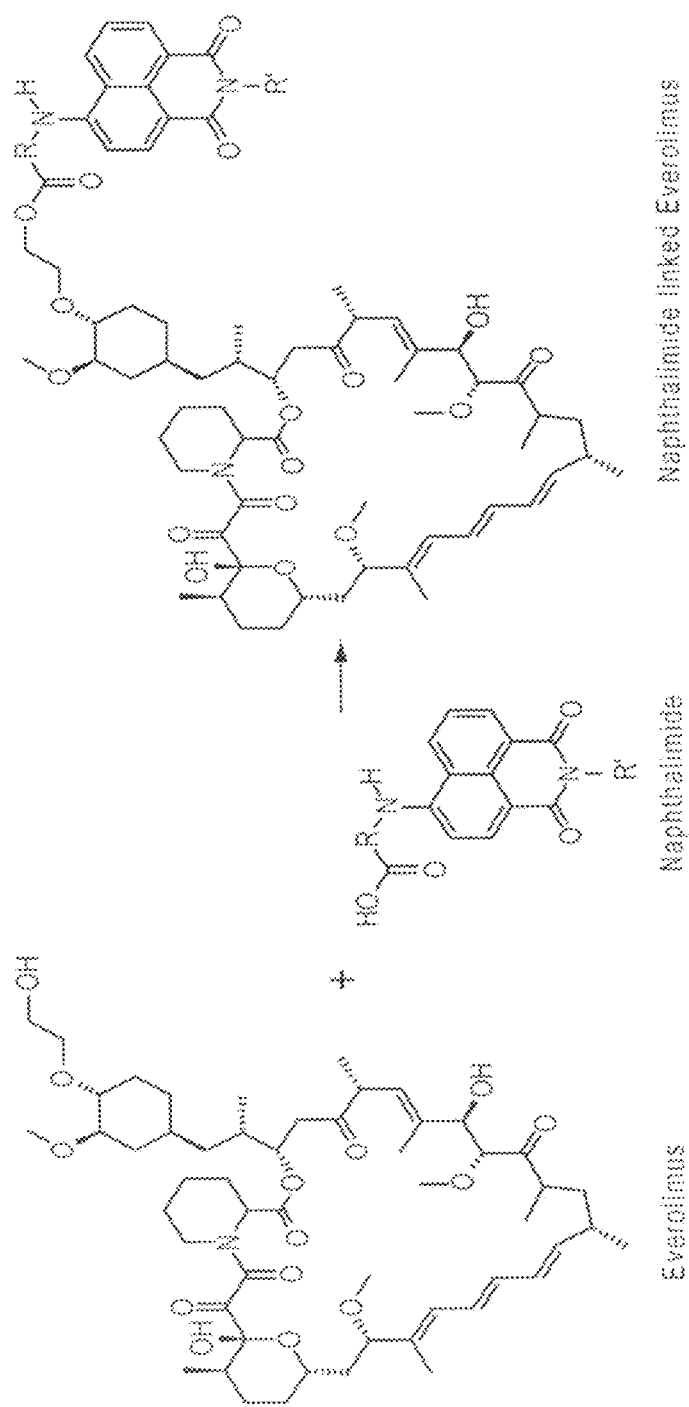
FIGS. 2A and 2B illustrate exemplary synthetic pathways for plaque-softening compounds tethered to pharmacological agents.
Figure 2B:
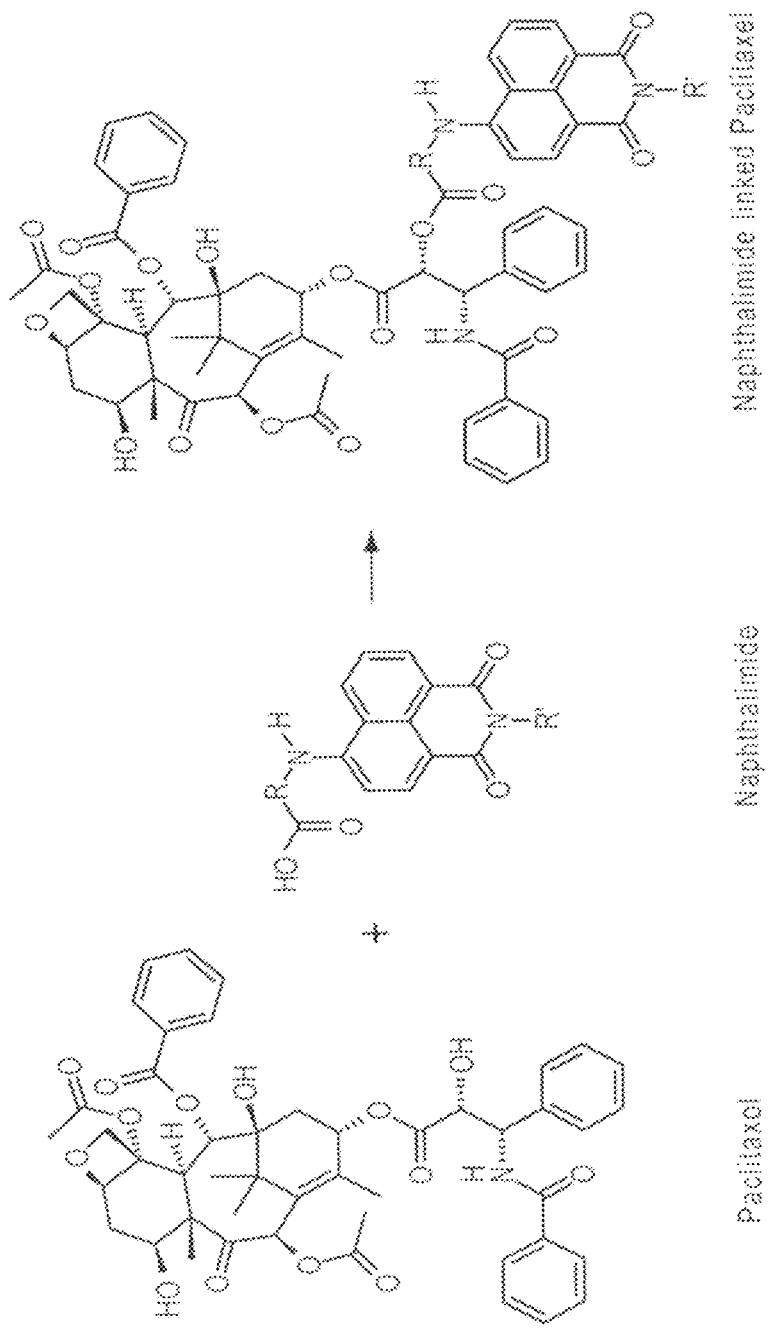

FIG. 2A illustrates a synthetic pathway for the production of the naphthalimide tethered to everolimus. FIG. 2B illustrates a synthetic pathway for the production of the naphthalimide tethered to paclitaxel. The reaction would be conducted with a DCC catalyst in organic solvent with purification to be complete on a silica gel column. The functional group R (the tether/linker) will control the rate of hydrolysis and the solubility and the R' (the tail) will control the water solubility of the compound.

Additional pharmacological agents that can be tethered to the compounds of the present invention include anti-thrombogenic agents, such as heparin, and magnesium sulfate; antiproliferation agents, such as paclitaxel and rapamycin; anticancer drugs; immunosuppressors; anti-infectives; antirheumatics; antithrombotic; HMG-CoA reductase inhibitors; CETP inhibitors ACE inhibitors; calcium antagonists; antihyperlipidemics; integrin inhibitors; antiallergics; antioxidants; GPIIbIIIa antagonists; retinoids; carotenoids; lipid-level lowering medicaments; DNA synthesis inhibitors; tyrosine kinase inhibitors; antiplatelets; anti inflammatories; tissue-derived biomaterials; interferons; monoclonal anti bodies; and NO production promoters.

Nonlimiting examples of the anticancer drugs include vincristine, vinblastine, vindesine, irinotecan, pirarubicin, doxorubicin, paclitaxel, docetaxel, mercaptopurine, and methotrexate.

Nonlimiting examples of the immunosuppressors include rapamycin and its derivatives, tacrolimus, azathioprine, cyclosporine, cyclophosphamide, mycophenolate mofetil, gusperimus, and mizoribine.

Nonlimiting examples of the anti-infectives, include antibiotics, antifungal, antiviral, antimycobacteria, antiprotozoal, antihelmintics/antiparasitic, and vaccines. Antibiotics include but are not limited to mitomycin, adriamycin, doxorubicin, actinomycin, daunorubicin, idarubicin, pirarubicin, aclarubicin, epirubicin, peplomycin, aminoglycosides, carbapenems, cephalosporins [1st-5th generation], aztreonam, fluoroquinolones, penicillins, macrolides, tetracyclines, monobactams, tigecycline, vancomycin, and zinostatin stimalamer. Antifungals include but are not limited to Amphotericin B, liposomal Amphotericin B, Lipid complex amphotericin B, flucytosine, nystatin, fluconazole, itraconazole, ketoconazole, posaconazole, voriconazole, terbinafine, caspofungin, micafungin, anidulafungin. Antivrials include but are not limited to acyclovir, adefovir, amantadine, cidofovir, entecavir, famciclovir, penciclovir, foscarnet, ganciclovir, interferon alpha, lamivudine, oseltamivir, ribavirin rimantadine, tenofovir, valacyclovir, valganciclovir, zanamivir, anti-HIV drugs. Anti-mycobacterials include but are not limited to ethambutol, isoniazid, pyrazinamide, rifabutin, rifampin, rifapentine, para-aminosalicylic acid, streptomycin, amikacin.

Nonlimiting examples of the antirheumatics include methotrexate, sodium thiomalate, penicillamine, lobenzarit, and DMARDs (disease modifying anti-rheumatic drugs, such as abatacept, adalimumab, anakinra, etanercept, tocilizumab, infliximab, rituximab, chloroquine, sulfasalazine, gold salts).

Nonlimiting examples of the antithrombotics include heparin, low molecular weight heparins (fondaparinux, enoxaparin, dalteparin), aspirin, warfarin, clopidogrel, prasugrel, ticagrelor, rivaroxaban, dipyridamole, abciximab, antithrombotic preparations, ticlopidine, and hirudin.

Nonlimiting examples of the HMG-CoA reductase inhibitors include serivastatin, serivastatin sodium, atorvastatin, nisvastatin, itavastatin, fluvastatin, fluvastatin sodium, simvastatin, rosuvastatin, and pravastatin.

Nonlimiting examples of the ACE inhibitors include quinapril, perindopril erbumine, trandolapril, cilazapril, temocapril, delapril, enalapril maleate, lisinopril, and captopril.

Nonlimiting examples of the calcium antagonists include hifedipine, nilvadipine, nicardipine, nifedipine, nimodipine, isradipine, felodipine, diltiazem, verapamil, benidipine, amlodipine, and nisoldipine.

Illustrative of the antihyperlipidemics is probucol, but may also include bile acid sequestrants, fibric acid derivatives, and statins.

Illustrative of the integrin inhibitors is AJM300.

Illustrative of the antiallergics is tranilast, but may also include antihistamines, antileukotrienes, mast cell stabilizers, decongestants, and glucocorticoids.

Nonlimiting examples of the antioxidants include catechins, anthocyanine, proanthocyanidin, lycopene, and β-carotene. Among the catechins, epigallocatechin gallate may be used.

Illustrative of the GPIIbIIIa antagonists is abciximab.

Illustrative of the retinoids is all-trans retinoic acid, but may also include Retinol, retinal, isotretinoin, alitretinoin, etretinate, acitretin, tazarotene, bexarotene, Adapalene.

Preferred examples of the flavonoids include epigallocatechin, anthocyanine, and proanthocyanidin.

Nonlimiting examples of the carotenoids include β-carotene and lycopene.

Illustrative of the lipid-level lowering medicaments is eicosapentaenoic acid including in combination with docosahexaenoic acid.

Illustrative of the DNA synthesis inhibitors are 5-FU, 6-mercaptopurine, 6-thioguanine, allopurinol, capecitabine, cytarabine, fludarabine, gemcitabine, leucovorin, methotrexate, and pemetrexed.

Nonlimiting examples of the tyrosine kinase inhibitors include imatinib, sunitinib, gefitinib, erlotinib, genistein, tyrphostin, and erbstatin.

Nonlimiting examples of the antiplatelets include ticlopidine, cilostazol, and clopidogrel.

Nonlimiting examples of the antiinflammatories include steroids such as dexamethasone and prednisolone.

Nonlimiting examples of the tissue-derived biomaterials include EGF (epidermal growth factor), VEGF (vascular endothelial growth factor), HGF (hepatocyte growth factor), PDGF (platelet derived growth factor), and BFGF (basic fibrolast growth factor).

Illustrative of the interferons is interferon-γ1a.

Illustrative of the NO production promoters is L-arginine.

As to whether one of these pharmacological agents or a combination of two or more different ones should be used, a selection can be made as needed depending on the case.

The plaque-softening compounds of the present invention can also be labeled. In an aspect, the compound is covalently bound to biotin via standard DCC coupling methods, as an example. Alternative methods for labeling a compound are known to those of ordinary skill in the art and are contemplated herein. The labeled compound will be easily detectable using a fluorescent or enzymatic assay linked to streptavidin from a streptavidin horseradish peroxidase system.

It is also possible to radiolabel the compounds of the present invention by the incorporation of labeled carbon, hydrogen, nitrogen, or oxygen during the conversion of the pharmacological agent. Any suitable radiolabel or isotopic marker known in the art can be used, such as hydrogen, carbon, pnictogens, chalcogens, and halogens, etc. However, it is to be understood that the labeled compounds of the present invention must be safe for administration to humans.

The compounds disclosed herein can be dissolved in a solvent to form a composition. In an example, the solvent can be phosphate buffered saline (PBS). Other suitable solvents include dimethylformamide, DMSO, ethanol, and isopropyl alcohol. In certain embodiments, the composition can optionally comprise one or more excipients, buffers, carriers, stabilizers, preservatives and/or bulking agents, and is suitable for administration to a patient to achieve a desired effect or result. The composition can be in any desired form, including but not limited to a liquid, a solid, a dispersion, a suspension, a hydrogel, a particle, a nanoparticle, a thin film, and shaped structure.

The plaque-softening compounds can be present in the composition in a concentration from about 0.01 mg/mL to about 100 mg/mL, for example from about 0.1 mg/mL to about 50 mg/mL, and as a further example from about 1 mg/mL to about 30 mg/mL.

The concentration of the compound, and optionally a tethered pharmacological agent, can be chosen such that a therapeutic, i.e., a plaque softening, effect is achieved when released into a blood vessel. One of ordinary skill in the art would readily be able to determine the concentration of the compound and/or the concentration of the pharmacological agent, in order to achieve the desired result.

The composition of the present invention may be provided in vials of various sizes for ease of use. In particular, an 8 mL vial can be used to hold 7 mL of the disclosed composition. The composition can be dispersed from the vial in one dose or is separate doses, for example a first bolus of about 4 mL, followed by a second bolus of about 0.5 to about 1.0 mL In an aspect, a saline flush can occur between application of the first and second bolus or after the second bolus. The compound can also be delivered from a diffusion catheter.

It is envisioned that the plaque-softening compound and a composition comprising the compound could be stored in a freeze-dried form, which could be reconstituted with saline/PBS prior to use.

In an aspect, there is disclosed a method for softening plaque present in a treatment zone of a blood vessel comprising a plaque matrix, the method comprising applying a bolus of a composition comprising a plaque-softening compound to the treatment zone of the blood vessel.

The composition disclosed herein can be applied to a blood vessel. In an aspect, a treatment zone of a blood vessel, such as an artery or vein, can be isolated. In another aspect, the composition is applied in an amount sufficient to provide a high systemic concentration. The composition can be injected into the blood vessel. In an aspect, the blood vessel is the superficial femoral artery (SFA) and its collateral branches. In another aspect, the composition of the present invention is applied to an isolated section of a blood vessel for an extended period of time, such as from about 1 second to about 1 hour, for example from about 1 minute to about 30 minutes, and for example from about 1 minute to about 10 minutes. The amount of time can vary depending upon the initial hardness and thickness of the plaque and the desired subsequent softness of the plaque.

The compositions of the present invention can be used to soften plaque, which can improve problems associated with diabetes, peripheral artery disease and coronary artery disease. The plaque lesions can vary in size. In an aspect, the plaque lesions range in length from about 1 to about 22 cm, for example from about 4 to about 9 cm, and as a further example about 4 to about 7 cm. The diameter of these plaque lesions can range from about 5 to about 7 mm.

In the event the plaque lesion is longer than the device used to apply the plaque-softening compound in a single treatment, it is envisioned that such longer plaque lesions can be treated in multiple step treatments, wherein the length of the lesion, and the length of the device to apply to the composition are factors in determining how many treatments may be needed to treat a lengthy plaque lesion.

In an aspect, the composition is delivered by a delivery system comprising an injection port and a treatment zone balloon. A light fiber is in the lumen of the delivery system and is designed to deliver blue light (i.e., 447 nm, for example 430-480 nm, wavelength) at low power. The blue light activates the PEG-based composition to cross-link with biomolecules of the vessel wall, such as collagen.

Any delivery system, including catheter designs with at least one balloon, can be used to deliver the plaque-softening composition to the treatment area, e.g., blood vessel. An exemplary delivery system can be found in U.S. Provisional Application No. 61/679,591, entitled "Endovascular Multi-Balloon Catheters with Optical Diffuser for Treatment of Vascular Stenoses," filed concurrently herewith, the disclosure of which is hereby incorporated by reference.

In particular, the vessel can be prepared by initial dilatation using angioplasty balloon to treat the stenotic region of diseased vessel (i.e., artery or vein). The composition is then injected between two occlusion balloons which isolate the treated vessel wall and bathe the vascular tissue. A secondary dilatation balloon located between the two occlusion balloons is inflated to restore the vessel lumen to the desired diameter. The blue light is delivered to "activate" the composition. The activated composition cross-links with native collagen fibers and/or covalently bonds a tethered drug to the blood vessel wall.

When activated, the naphthalimide compounds of the present invention have a singlet charge transfer state, which does not produce singlet oxygen. This is in contrast to singlet oxygen production, which is through triplet state sensitization. See Samanta, Ramachandram, Saoja, An investigation of the triplet state properties of 1,8-naphthalimides: a laser flash photolysis study, J. Photochem. Photobiol A; Chem, 101 (1996), 29-32 (and references therein). The naphthalimide compounds of the present invention decay predominately by intramolecular charge transfer state that leads to emission (C-T fluorescence). The lack of oxygen dependence of the emission of the naphthalimide compound indicates the charge transfer states are short lived.

Figure 3:
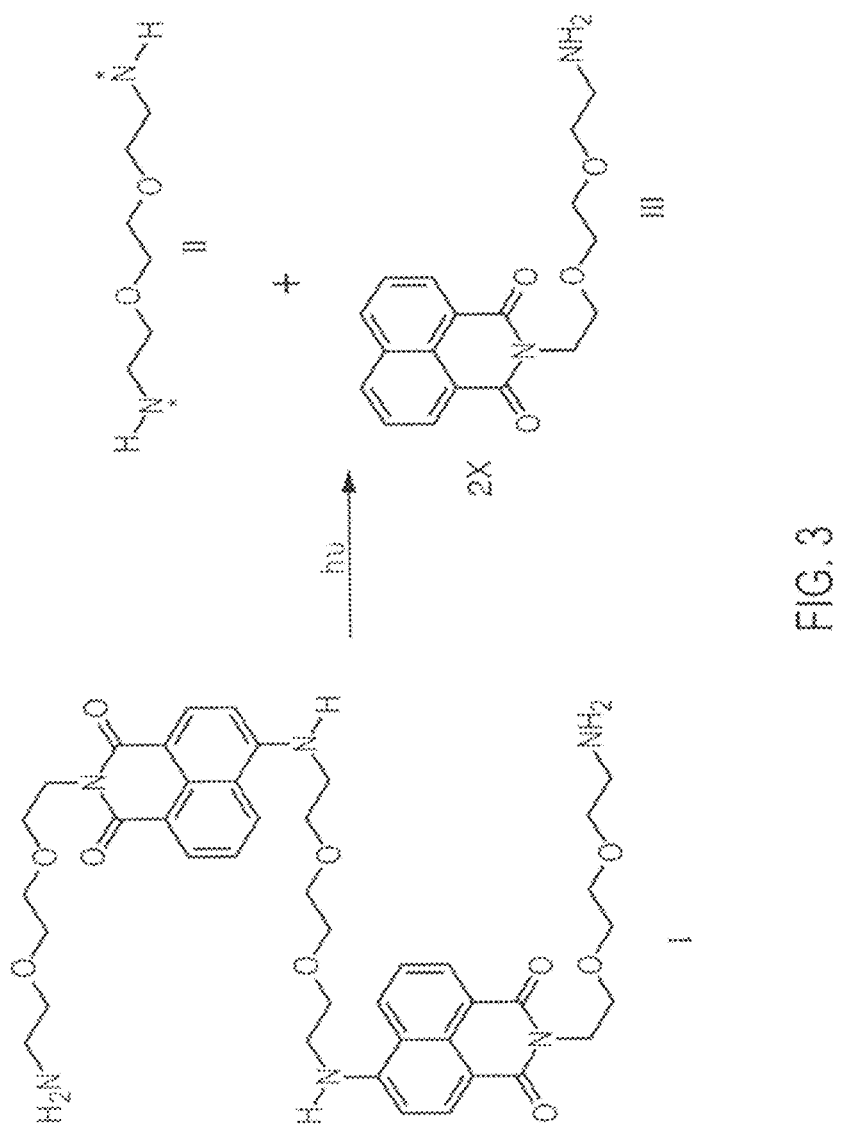
FIG. 3 illustrates a reaction scheme for the activation of a naphthalimide compound of the present invention.

The activation of the naphthalimide compound of the present invention is believed to follow the reaction scheme in FIG. 3. As illustrated in the reaction scheme, an exemplary dimer compound (I) is activated. The "linker" functional group (II) is released as well as two compounds (III). It is believed without being limited to any particular theory, that these reaction products (II) and (III) enter the systemic circulation and is excreted by the kidneys.

Fluorescence studies can be used to demonstrate that the composition comprising the disclosed naphthalimide compound can penetrate the blood vessel, and thus treatment over the entire area of the blood vessel can be ensured.

The methods of using the disclosed compositions can result in an increase in softened plaque as compared to plaque that has not been subjected to administration of the disclosed compositions. The change in the softness of the plaque can be readily visualized by one of ordinary skill in the art and/or by mechanical manipulation of section of a blood vessel comprising plaque. In particular, a treated section of blood vessel is characterized as being softer and more malleable. It is believed that the softened plaque will be more compliant and responsive to balloon dilatation, thereby resulting in an increase in lumen diameter of the blood vessel as well.

There is also disclosed a method of increasing a lumen diameter of an isolated section of a blood vessel, comprising isolating a section of a blood vessel lumen; and applying to the isolated section a plaque-softening compound, wherein the lumen area of the blood vessel is increased compared to the lumen area of a blood vessel that has not been treated with the compound. This method may further comprise after the step of isolating, a step of expanding a vessel lumen having a first diameter, which is smaller than a normal lumen diameter for the vessel at a location adjacent to the isolated section, to a second diameter which is equal to or greater than the normal lumen diameter. After the step of expanding, the method may further comprise a step of activating the plaque-softening compound with a sufficient amount of an activating agent.

In another aspect, there is disclosed a method of tacking-up of plaque against a wall of a vessel's lumen comprising isolating a section of a vessel's lumen comprising plaque; and applying to the plaque a plaque-softening compound comprising at least six ethyleneoxy groups, wherein the plaque tacks-up against the wall of the vessel's lumen.

This method may further comprise after the step of isolating, a step of expanding a vessel lumen having a first diameter, which is smaller than a normal lumen diameter for the vessel at a location adjacent to the isolated section, to a second diameter which is equal to or greater than the normal lumen diameter. The second lumen diameter can be maintained during an activating step. The second diameter of the lumen can comprise a diameter which exceeds the normal diameter by up to thirty percent. The lumen diameter can be expanded by balloon angioplasty. The step of expanding can be performed at least one of prior to, during, and subsequent to the applying step.

After the step of expanding, the method may further comprise a step of activating the plaque-softening compound with a sufficient amount of an activating agent.

One of ordinary skill in the art can use various techniques known in the art to clinically assess the softening of plaque. For example, a fluoroscope can be used to view the blood vessel with calcified plaque before and after treatment with the disclosed composition. Similarly, computed tomography angiograph (CTA) can be used pre- and post-treatment to observe the changes in the treated blood vessel comprising plaque.

Prior to performing a disclosed method, one of ordinary skill in the art may assess a possible plaque lesion by grading the amount of calcium present in the plaque matrix. For example, one may use a calcium grading scale as follows:

Grade 0—No Calcification:
No visual calcification present along the arterial wall of the artery prior to the injection of contrast.

Grade 1—Mild to Moderate Calcification:
Calcium is visible along one side of the arterial wall in the area of the target lesion prior to injection of contrast. The calcium present encompasses <50% of the total target lesion treatment area by visual estimate and/or the calcium is not circumferential (360°) in nature (i.e. on both sides of the vessel lumen extending 2 cm or greater on a single AP view) or classified as exophic calcification, no impedance of blood flow in the vessel.

Grade 2—Moderate to Severe Calcification:
Calcium is visible along one or both sides of the arterial wall in the area of the target lesion prior to injection of contrast. The calcium present encompasses ≥50% but <60% of total target lesion treatment area by visual estimate and/the calcium is not circumferential (360°) in nature (i.e. on both sides of the vessel lumen extending 2 cm or greater on a single AP view) or classified as exophic calcification, and does not impede blood flow by more than 50%.

Grade 3—Severe Calcification:
Calcium is visible along both sides of the arterial wall, covers 2 cm or greater of the target lesion area prior to injection of contrast, encompasses 60% of the total target lesion treatment area by visual estimate and/or the calcium is circumferential (360°) in nature (i.e. on both sides of the vessel lumen extending 2 cm or greater on a single AP view) or classified as exophic calcification, significantly impedes blood flow in the vessel.

EXAMPLES

Example 1—Synthesis and Initial Purification of a Compound of Formula (V)

In a 100 mL round bottom flask, 15 grams of JEFFAMINE® 148 (Sigma-Aldrich, St. Louis, Mo.) was combined with 1 gram of 4-bromo-1,8-naphthalic anhydride (Sigma-Aldrich, St. Louis, Mo.). The temperature was held from about 100 to about 110° C. for about 18 to about 24 hours, and was constantly stirred. The reaction mixture was cooled to room temperature, combined with 50 mL of ethanol (Pharmco-Aaper, Brookfield, Conn.), and then refrigerated at about 4° C. until crystals precipitated from solution (approximately 48 hours). The cold solution was then filtered by vacuum filtration, and the product, crystals of the compound of formula (V), were washed with 10 mL of cold ethanol. The percent yield after precipitation with ethanol was calculated to be 25%.

Purification of the crystals involved combining the isolated product with 30 mL of ethanol and heating the mixture to boiling. When all of the crystals were dissolved, the heat was removed and the solution cooled to room temperature, then refrigerated to about 4° C. overnight, allowing crystals to precipitate from solution. The crystals were isolated using vacuum filtration, rinsed with 10 mL of cold ethanol, and allowed to air dry. No significant losses were recorded during this recrystallization step. The material prepared in this fashion was approximately 75% pure naphthalimide dimer, the desired product, with the impurity profile composed of monomeric analogues.

Example 2—Preparation of the Compound of Formula (V) Standard Solution

The naphthalimide solution was prepared as described in Example 1. A 5.0 mg/mL solution was prepared by diluting the compound of formula (V) with phosphate-buffered saline (PBS). With constant stirring, the sample pH was adjusted to 7.4 by dropwise addition of a 10% (v/v) solution of acetic acid. The final concentration of the solution was confirmed by spectrophotometric analysis (Ocean Optics, USB4000), in which the absorbance (440 nm) of a 1:200 dilution of the compound of formula (V) solution in isopropyl alcohol was measured. The observed absorbance of this sample was 0.5.

Example 3—Naphthalimide Purity by HPLC

A chromatographic separation was performed on a modular HPLC system with a PDA detector and data analysis package (Varian), and detection wavelengths of 210, 254, 360, and 440 nm, The analytical separation was achieved using $C_{18}$ column (Alltima HP, 5 μm, 4.6×250 nm, Alltech) and gradient elution. The elution solvents consisted of mobile phase A, 0.15 (v/v) TFA (aq), and mobile phase B, a 90:10 ACN:water with 0.1% (v/v) TFA. A 1:5 dilution (PBS) of the compound of formula (V) naphthalimide standard solution from Example 2 was analyzed. Using a 20 μL injection volume and a flow rate of 1.0 mL/min the standard solution was introduced onto a column that had been pre-equilibrated for 10 minutes with a 95:5 mobile phase ratio of solvents A and B, respectively. Subsequent elution of the analytes was accomplished using a linear gradient with a 1 minute hold at the beginning to 90% mobile phase B at 20 minutes, followed by a 5 minute hold at the end of the gradient.

Example 4—Residual Amine Determination by HPLC Analysis

20 µL of the naphthalimide solution from Example 2 was placed in a micro-centrifuge tube and diluted with 180 µL of reaction buffer (0.15 M NaHCO$_3$, pH=8.6). The sample was vortex mixed and then 200 µL of the dabsyl chloride reagent (12.4 mM DABS-Cl in acetone) was added. The samples were incubated at 70° C. for 15 minutes with intermittent vortex mixing, and then cooled in an ice bath for 5 minutes. Next, 400 µL of a dilution buffer (50:25:25 (v/v/v) acetonitrile:ethanol:mobile phase A (chromatographic mobile phase)) was added and the sample mixed. Samples were then centrifuged at 10,000 rpm (Eppendorf 541R) for 5 minutes and then analyzed.

The chromatographic separation was performed on a modular HPLC system with a PDA detector (436 mm) and data analysis package (Varian). The analytical separation was achieved using C$_{18}$ column (Alltima HP, 5 µm, 4.6×250 mm, Alltech) and gradient elution. The elution solvents consisted for mobile phase A, 96% 9 mM Na$_2$HPO$_4$, 4% DMF and 0.1% TEA (aq.), and mobile phase B, 80:20 ACN:water. A 20 µL injection volume and flow rate of 1.0 mL/min were used with a starting mobile phase ratio of 92:8 mobile phase A to B, respectively, a two minute hold, and then a gradient to 100% mobile phase B at 40 minutes followed by a 10 minute hold. JEFFAMINE® 148 standards were prepared and used to determine linearity and limit of detection for the compound of formula (V) standard solution.

Example 5—Isolation and Purification of a Compound of Formula (V) Using Preparative HPLC A preparative HPLC approach was used to isolate and specifically purify the compound of formula (V) dimer from the compound of formula (V) naphthalimide product produced from the ethanol crystallization. The HPLC method used was based on the purity method outlined above; however, method modifications were made to replace acetonitrile with ethanol and TFA with acetic acid in the mobile phase. The preparative separation utilized a C$_{18}$ column (X-bridge, 10 µm, 19×250 mm, Waters). The mobile phase consisted of mobile phase A, 0.1% acetic acid (aq), and mobile phase B, 9:1 ethanol:water (0.1% v/v acetic acid). The column was pre-equilibrated at a starting mobile phase of 95% A:5% B for 20 minutes, at the start of the gradient was a 2 minute hold followed by a linear gradient to 90% B at 40 minutes and a 10 minute hold. An injection volume of 8.5 mL (12 mg/mL purified compound of formula (V)) and flow rate of 8.5 mL/minute were used as well as a detector wavelength of 440 nm. The compound of formula (V) fractions were collected and analyzed using the analytical purity method presented above. Fractions meeting a minimum purity criterion were combined and the solvent driven off by rotovapping the solution to dryness. Excess acetic acid was removed by repeated (two total) dissolution of the product in deionized water followed by rotovapping to dryness. Finally the product was quantitatively transferred from the round bottom flask to a freeze drying flask by dissolving the product in a minimal amount of deionized water. This solution was frozen at a temperature of −80° C. for a minimum of 24 hours. This final purification approach effectively removed excess solvent and acetic acid from the product as a dimer solution at the desired pH value of 7.4. The naphthalimide dimer solution has demonstrated excellent stability for periods up to 18 months. The dimer in powder form has shown no evidence of degradation for periods exceeding two years of storage in a dessicator at −20° C.

Example 6—Spectral Characterization of the Naphthalimide Monomer and Dimer

Standards of the naphthalimide monomer and dimer were analyzed by ESI-MS analysis for molecular weight (MW) confirmation. Standards were analyzed on a Waters A-TOF I mass spectrometer. A stock solution of the purified solid was prepared in PBS at a concentration of 2 mg/mL. Serial dilution was used to prepare solutions of decreasing concentration until the limit of detection was reached. Absorbance ($\lambda_{max}$) curves were measured for the naphthalimide dimer using PBS, DMF, and IPA as the dilution solvent. The extinction coefficient for the naphthalimide monomer was only determined in IPA.

In view of the foregoing, one of ordinary skill in the art would be able to synthesize the disclosed monomer, dimer, trimer (star, capped, linear) naphthalimide compounds disclosed herein.

Example 7—Plaque Penetration

Diseased arteries were obtained from limb amputations (leg) due to advanced Periperal Arterial Disease (PAD) from patients at a regional hospital. The received arteries were evaluated and chosen such that the diseased section was of reasonable size to accommodate the treatment catheter balloon length being used. The catheter balloon diameter used was also matched to the diameter of the artery and capable of achieving a 1:1.25 (ratio of artery diameter to balloon diameter) overstretch. The artery was laid in a petri dish and an angioplasty balloon was inserted and inflated for 60 seconds to impart the desired overstretch. While the angioplasty balloon was inflated a permanent marker was used to define the treatment zone (where the overstretch was imparted by the balloon) on the outer surface of the artery. The angioplasty balloon was deflated and removed. The inner lumen of the diseased artery was exposed to a plaque softening composition comprising a compound of formula (V) naphthalimide formulation (2 mg/mL in phosphate buffered saline, pH=7.4) for a period of 5 minutes. For the purpose of filling the artery, one end was clamped, the artery was held upright and a syringe was used to dispense the naphthalimide solution until the inner lumen was filled. The open end of the artery was then clamped and the soaking period of 5 minutes commenced. After the 5 minute soaking period, the clamps were removed and a treatment catheter with a dilatation balloon and capable of housing a light fiber for light activation was centered in the treatment zone of the artery as defined by the markings made on the outside of the artery. The treatment balloon was inflated to a similar diameter as the angioplasty balloon in the previous step and light activation was imparted using the light fiber contained in the central lumen of the catheter and illuminating through the treatment balloon. Light activation involved using a laser (447 nm) and a power level of 625 mW/cm delivered to the treatment zone for a period of 60 seconds. After completion of light activation, the laser was turned off, the treatment zone balloon was deflated and the catheter removed from the artery. Control arteries having no exposure to the plaque softening compound were treated in an identical manner to those receiving the plaque softening compound, however, phosphate buffered saline (pH 7.4) was used in place of the plaque softening compound, i.e., the naphthalimide compound. Arteries were cut open lengthwise and the treated section was evaluated by visual examination.

Figure 4A:
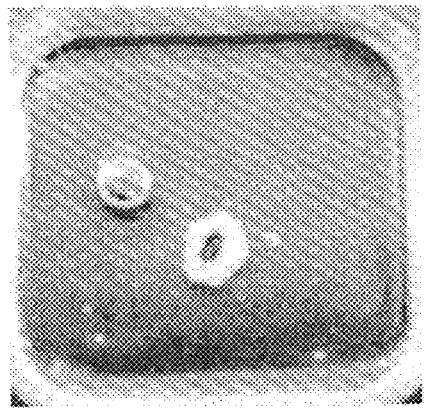
FIGS. 4A-F are photos illustrating various aspects of the present invention.
Figure 4B:
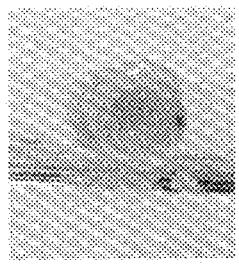
Figure 4C:
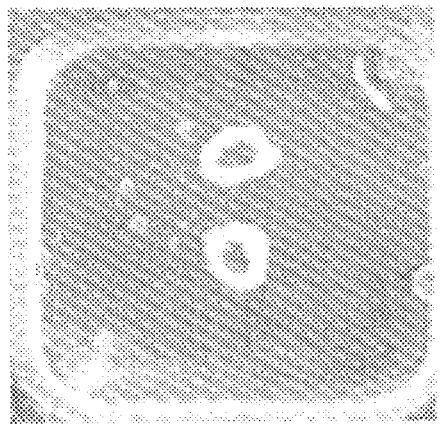
Figure 4D:
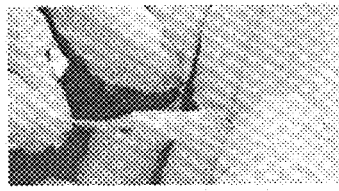
Figure 4E:
Figure 4F:
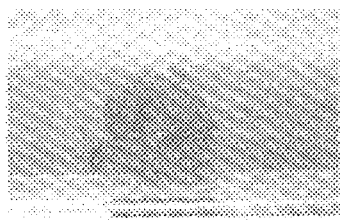

FIGS. 4A and 4B are photos of an untreated section of popliteal artery that was fairly healthy, having only a slight plaque formation. FIGS. 4C and D are photos of the same artery after angioplasty with a 25% overstretch. FIGS. 4E and F are photos of the same artery after it has been treated, i.e., soaked with the plaque softening composition comprising the compound of formula (V).

Figure 5A:
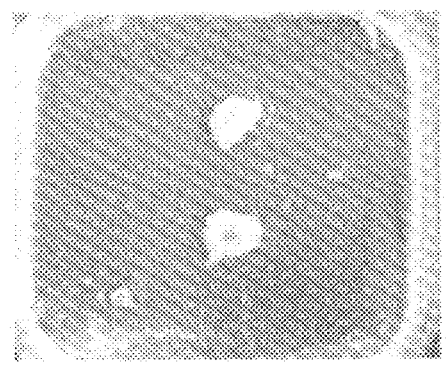
FIGS. 5A-F are photos illustrating various aspects of the present invention.
Figure 5B:
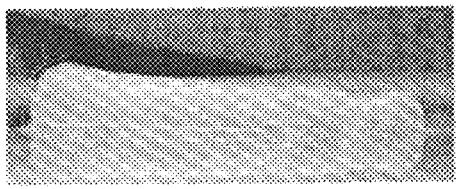
Figure 5C:
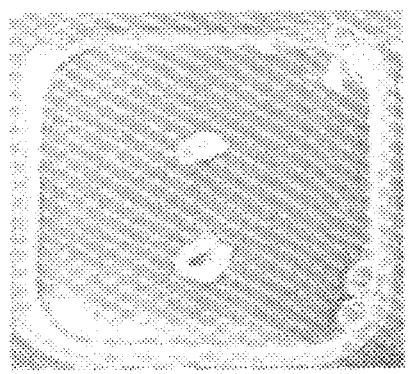
Figure 5D:
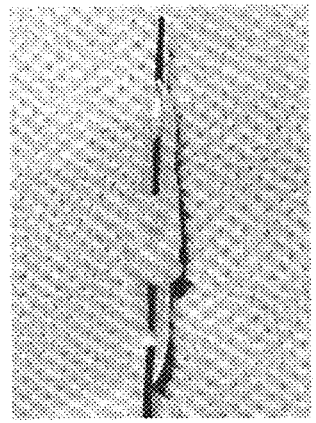
Figure 5E:
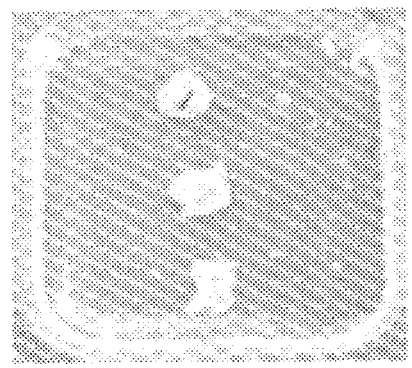
Figure 5F:
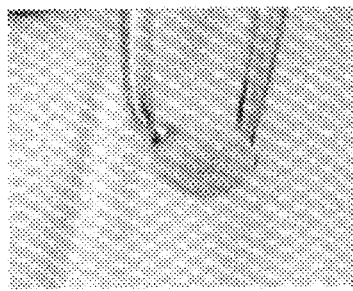

FIGS. 5A and 5B are photos of an untreated section of tibial artery that was partially covered in hard or soft plaque. FIGS. 5C and D are photos of the same artery after angioplasty with a 37% overstretch. FIGS. 5E and F are photos of the same artery after it has been treated, i.e., soaked with the plaque softening composition comprising the compound of formula (V).

Figure 6A:
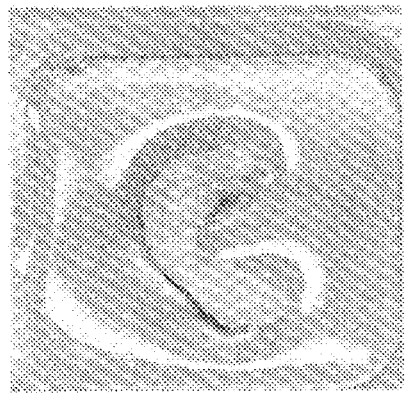
FIGS. 6A-F are photos illustrating various aspects of the present invention.
Figure 6B:
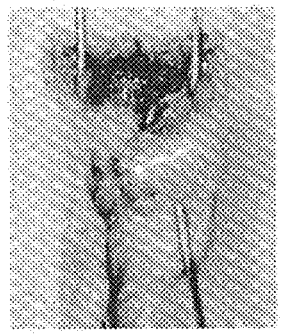
Figure 6C:
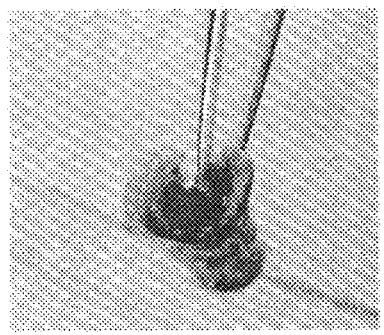
Figure 6D:
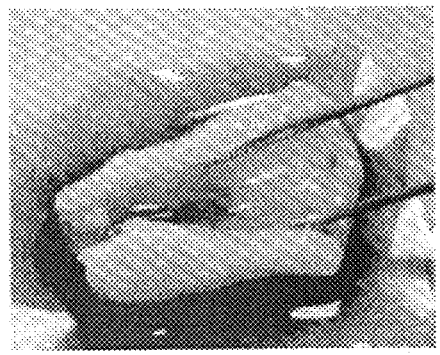
Figure 6E:
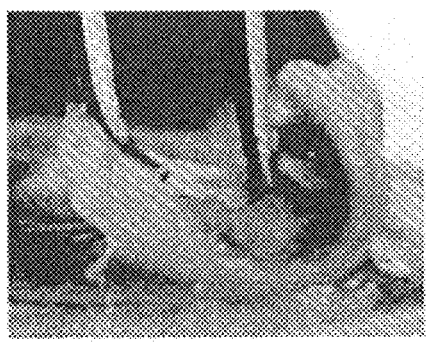
Figure 6F:
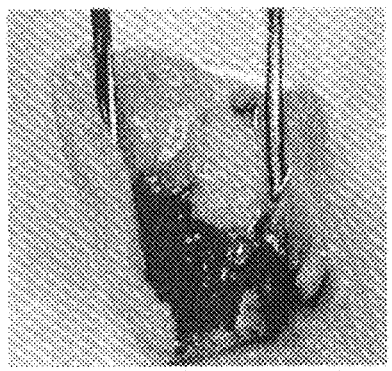

FIGS. 6A, 6B, and 6C are photos of an untreated section of popliteal artery that was partially covered in hard or soft plaque. As can be seen in FIG. 6B the artery was cut open lengthwise (no angioplasty). FIGS. 6D, 6E and 6F are photos of the same artery after it has been treated, i.e., soaked with the plaque softening composition comprising the compound of formula (V).

Figure 7A:
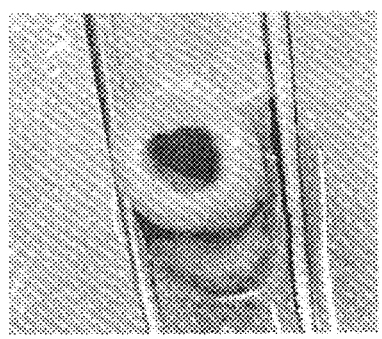
FIGS. 7A-E are photos illustrating various aspects of the present invention.
Figure 7B:
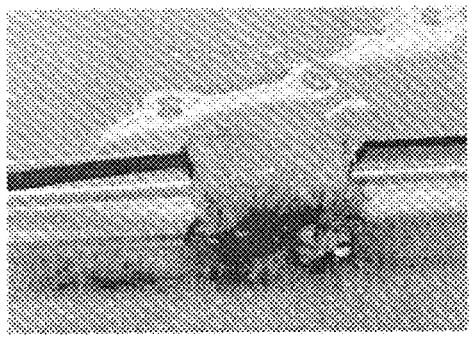
Figure 7C:
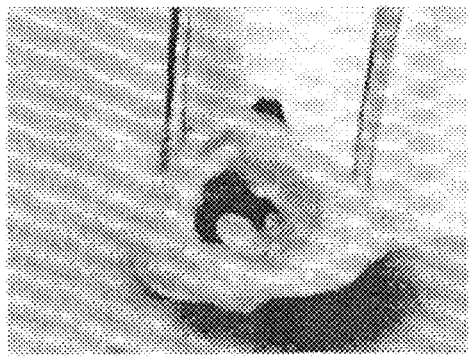
Figure 7D:
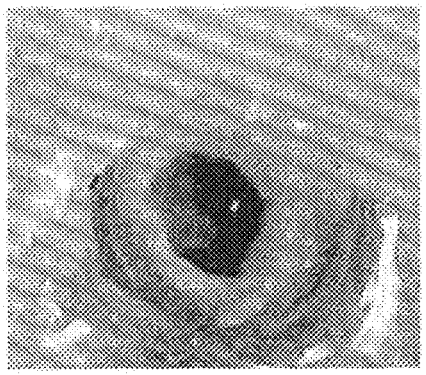
Figure 7E:

FIG. 7A is a photo of a section of popliteal artery having large areas of soft plaque. FIGS. 7B and 7C are photos of the same artery after angioplasty with a 25% overstretch. FIGS. 7D and 7E are photos of the same artery after it has been treated, i.e., soaked with the plaque softening composition comprising the compound of formula (V).

Figure 8:
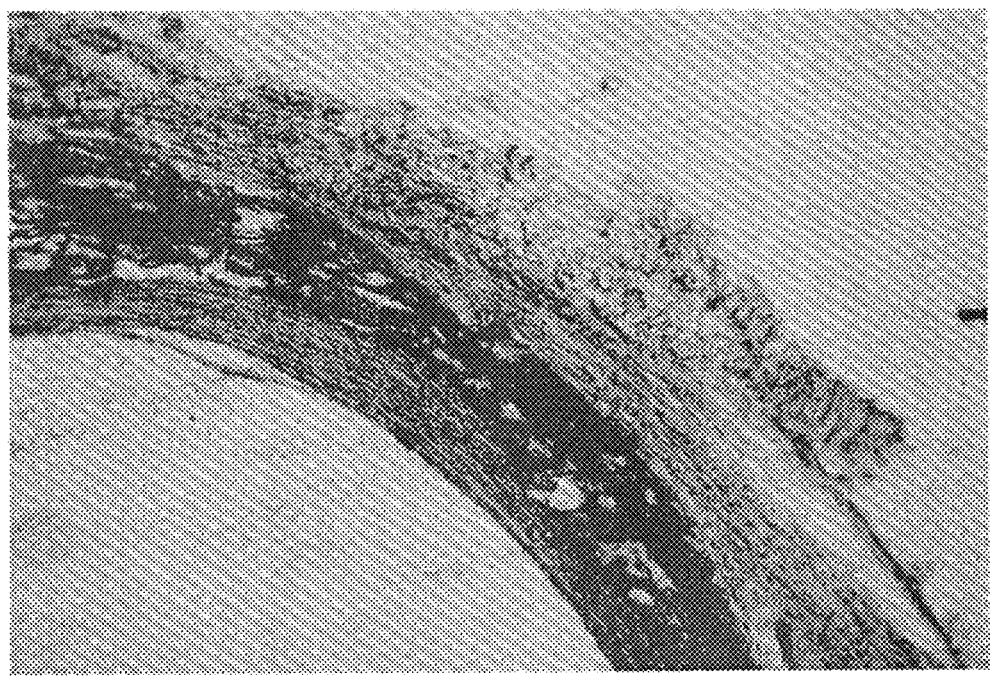
FIG. 8 is an image captured on a microscope showing the various layers of a blood vessel and the crystalline plaque (black area) located between the two media layers of tissue.

Prior to cutting the artery for visual examination samples from the treated and untreated sections were collected and preserved for histological examination. This sample preparation involved using surgical scissors to cut a section of approximately 2 mm in length and placing the section into OCT embedding medium in a plastic mold. The sample was then immediately immersed in liquid nitrogen for a period of at least 1 hour. After this time, samples were stored in a −80° C. freezer until ready for further analysis. Histological analysis involved placing the frozen section into a cryostat and cutting into sections of 10 microns in thickness. Individual sections were placed onto poly-L-lysine coated glass slide, coverslipped from frozen using Cytoseal 60 and viewed under dark field magnification (10×) using a Zeiss Axiovert 200 microscope. Additional histological evaluation was performed using H&E staining which allowed for better elucidation of the soft plaque. The crystalline nature of hard plaque is readily visible without staining. Under this magnification the crystalline structure of the calcific plaque was readily visible, as shown in FIG. 8 the dark area between the two lighter colored areas of the media. Specific landmarks, such as the presence and appearance of both hard (calcified) and soft plaque, were identified. There was a definitive visual observation of apparent softened plaque in the treated region. There was a definitive observation of tacking of intimal flaps.

Microscopic Evaluation—

Figure 9A:
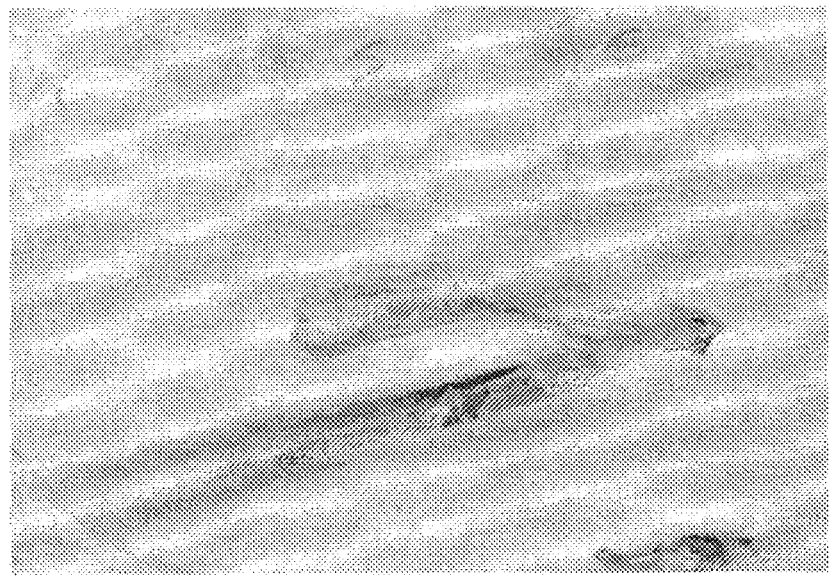
FIGS. 9A and 9B are photos of an isolated section of a blood vessel before and after it has been subjected to a plaque-softening compound of the present invention.
Figure 9B:
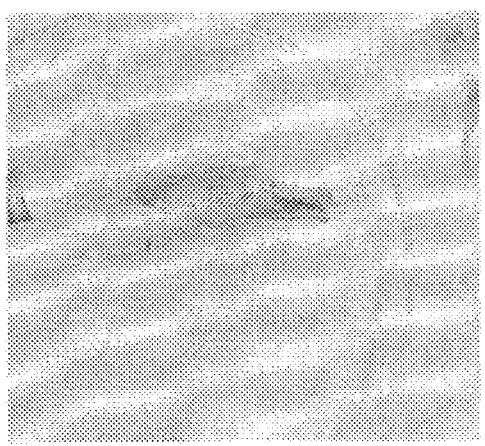
Figure 10:
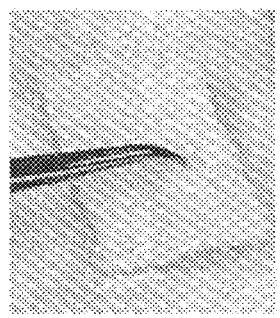
FIG. 10 is a photo of an untreated section of a blood vessel after angioplasty and exhibiting a tissue dissection or fissure.

In particular, the treated plaque was more malleable. See FIGS. 9A-B. FIG. 9A is a photo of an isolated section of a blood vessel comprising a plaque matrix. The shriveled nature of the artery represents what the untreated section of the artery looked like after the artery was cut open. FIG. 9B is a photo is the blood vessel of FIG. 9A after it has been subjected to application of composition comprising a plaque-softening compound. The treated section is distinguishable from the untreated portion of the artery as it is distended and smoother. The appearance of the untreated portion (to the right) is very similar to the shriveled nature of the entire artery as shown in FIG. 10A. The treated and untreated sections of artery were viewed under a microscope. There was less evidence of calcium crystals in the treated sections.

Example 8—Tissue Immersion

A sample of human tissue from the common and lower femoral artery was received. It was stored in saline and refrigerated until use. Based upon visual and tactile observations, the arteries were approximately 7-8 mm in diameter and contained evidence of both hard and soft plaque. The soft plaque has a yellow fatty appearance that is distinguishable from the vessel wall. The hard plaque presents itself as hard pieces of material that can be pulled (with a forceps) from the soft plaque. Sections of the artery suitable for catheter work were segregated and stored in phosphate buffered saline (PBS), pH=7.4. From the remaining arterial sections, pieces of tissue containing both hard and soft plaque were removed. These pieces were either placed in a solution of PBS (pH=7.4), or dimeric naphthalimide, such as a compound of formula (V) (which is in PBS, pH=7.4). Prior to immersion in either solution the relative hardness of the plaque was evaluated via manual manipulation with a forcep. After a 5 minute soak in solution (typical exposure time), no difference in the samples soaked in PBS was noticed (control). There was a slight softening of the plaque exposed to a compound of formula (V) (inventive example). The samples were then left in their respective solutions for an additional 90 minutes. The plaques soaking in the PBS (control) remained hard, whereas the plaques soaking in the compound of formula (V) (inventive example) were significantly softer and more pliable.

Example 9—Tissue Receiving Only Angioplasty

The tissue was an artery approximately 7.4 mm in diameter. An Ultra-thin SDS 8 mm×30 mm catheter was used to dilate the artery to 7.55 mm (approximately a 2% overstretch). A fissure or a possible dissection running down the length of the tissue sample was observed. See FIG. 10

Figure 11A:
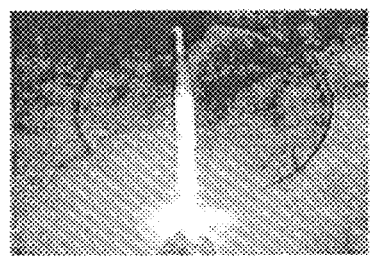
FIG. 11A is a photo of a section of artery being activated.
Figure 11B:
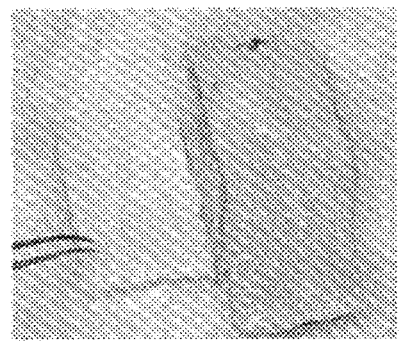
FIG. 11B is a photo of a side-by-side comparison of an untreated section of a blood vessel (on the left) with a treated section of a blood vessel (on the right).

Example 10—Tissue Receiving a Plaque-Softening Composition Comprising a Compound of Formula (V) and then Angioplasty A section (6.5 cm in length) of artery was exposed to the composition for 5 minutes. An 80 mm catheter was used to impart a 25% overstretch to the artery. The angioplasty was followed by photoactivation at 1800 mW for 60 seconds using the same 80 mm catheter with a 60 mm light fiber centered in the catheter. See FIG. 11A. When this artery was opened up there was no fissure observed as with the previous artery, however, there did appear to be somewhat of a seam which may indicate the photoactivated repair of a fissure after the plaque is pre-softened and then dilated. See FIG. 11B.

Example 11—Tissue Receiving Angioplasty and then a Plaque-Softening Composition Comprising a Compound of Formula (V)

Figure 12:
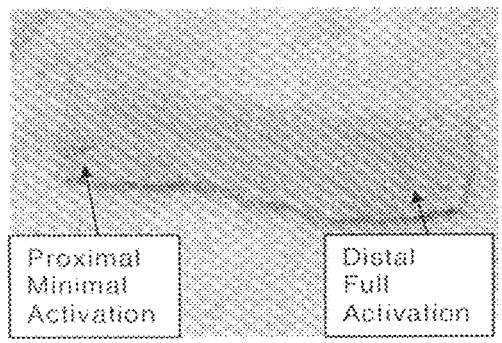
FIG. 12 is a photo of a treated section of blood vessel after activation of a plague-softening compound.

A catheter with an 80 mm treatment zone balloon was used however the photoactivating light fiber was only 60 mm in length. During activation it was noted that the light fiber was shifted distally in the catheter. This meant that the distal end of the artery was receiving photoactivation, however, the proximal end received little or no light. A fissure down the length of the artery was again observed. At the proximal end where there was minimal light activation there did not appear to be repair. Distally down the artery towards adequate photoactivation there appeared to be a seam indicating repair. At the very distal end there was a small flap which indicated that full repair may not have occurred. See FIG. 12.

Example 12—Other Photoactivated Material

Figure 13:
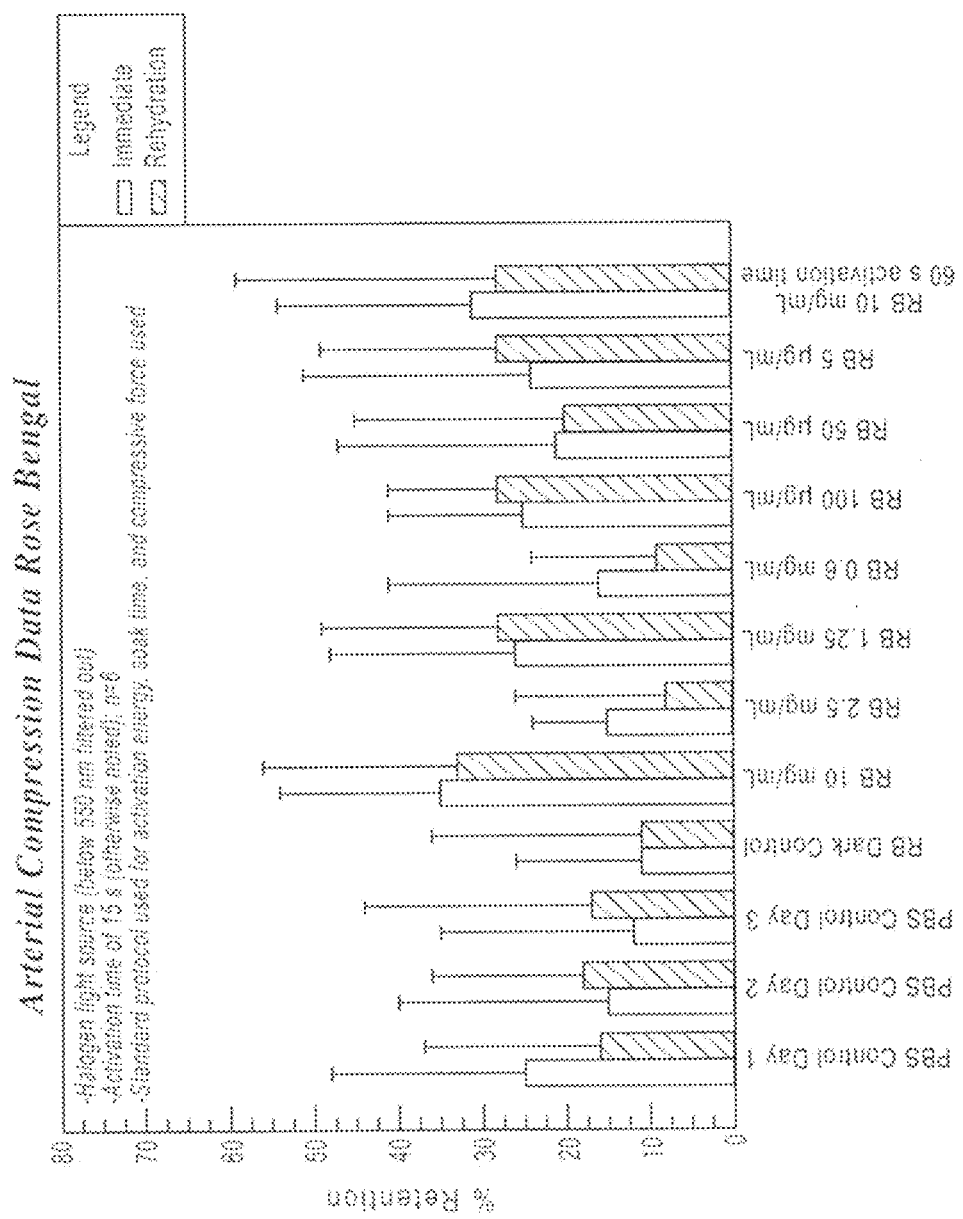
FIG. 13 is a graph illustrating arterial compression data for rose Bengal.

Singlet oxygen generating species, such as Rose Bengal, riboflavin, and methylene blue were tested to determine if they would be effective at arterial compression. No efficacy was observed, as shown in FIG. 13.

Example 13—Attachment and Release of Pharmacological Agent Tethered to a Compound of Interest A fresh excised porcine artery can be cleaned of excess tissue and rinsed in PBS. The artery wall can undergo angioplasty to simulate clinical injury. The artery can be filled with a 1.0 mg/mL solution of a pharmacological agent bound to a compound of interest, such as a naphthalimide compound, and allowed to soak for 5 minutes. A balloon catheter capable of accommodating a cylindrically illuminating fiber can be inflated in the artery to expel any extra material. The artery can be irradiated to activate the naphthalimide compound and effect the attachment of the pharmacological agent to the blood vessel wall. After irradiation, the balloon will be deflated and removed. Arterial material outside of the treatment zone, that material not around the illumination zone will be removed and discarded. The artery will be rinsed with PBS and then soaked in PBS multiple times in the dark for at least 1 hour to remove any unbound material.

To determine the attachment of the pharmacological agent to the blood vessel, the artery can be blotted dry and weighed. The artery will be homogenized and warmed to 40° C. in a basic (high pH) solution. This basic treatment will result in the rapid hydrolysis of the bond, e.g., an ester bond, and the complete release of the pharmacological agent, e.g., Everolimus. The total amount of the tethered pharmacological agent can be determined by HPLC.

To determine the release (hydrolysis) rate, a section of treated artery can be blotted dry and weighted. The artery will be placed in PBS and incubated at 37° C. Aliquots of buffer can be removed and analyzed via HPLC to determine the amount of pharmacological agent released as a function of time.

Example 14—A Proposed Synthesis of a Capped Naphthalimide Trimer

Dissolve 0.500 gram of 4-chloro-1,8-naphthalic anhydride (2.16 mmoles, mw=232) in 100 ml of anhydrous ethanol. Add 7.3 mg TEA (0.072 mmoles, mw=101). Add 0.316 grams of JEFFAMINE® T-403 (0.718 mmoles, mw=440) and protect the reaction vessel with a drying tube. (Note: The reaction produces water, the reaction may be facilitated by the addition of 20 grams of dry molecular sieves.) The reaction should be heated to 50° C. The reaction should be monitored by TLC on fluorescence plates. The product should NOT be fluorescent when viewed under blue (450 nm) light. The reaction will be run for up to 168 hours, if the reaction is not complete at this time, the solution will be verified to be basic (add TEA as necessary). If basic, the reaction temperature will be increased in 10° C. step up to reflux. Chromatography was on silica gel may be used to purify the product, the solvent system to be determined by TLC.

Dissolve 0.53 grams (0.5 mmoles, mw=1065.45) of the 4-chloro-⅓T403-naphthalimide in 1000 ml of o-dichlorobenzene (bp=178-180° C.). After the naphthalimide is completely dissolved, add 0.22 grams of JEFFAMINE®T-403 (0.5 mmoles, mw=440). The reaction will be refluxed in the dark under nitrogen and the reaction monitored by the increase in fluorescence and TLC for up to 168 hours. Partially reacted material will be fluorescent but will not be moved from the origin on TLC. While the large volume of solvent has been selected to prevent formation of higher order aggregates, it will slow the reaction unacceptably. If the reaction is too slow, the volume of solvent may be reduced. It is expected that this capped naphthalimide trimer may have fast plaque penetration, but low water solubility.

Example 15—Synthesis of 4-Chloro-Butyl Naphthalimide

Dissolve 0.500 gram of 4-chloro-1,8-naphthalic anhydride (2.16 mmoles, mw=232) with 100 ml of anhydrous ethanol in a 250 ml round bottom flask. Add 0.22 g TEA (2.2 mmoles, mw=101). Place a small stir bar in the flask. Add a cooled reflux condenser to the flask. Place the flask in a heating mantel on a stir plate and heat to reflux. The 4-chloro-1,8-naphthalic anhydride should dissolve. After the 4-chloro-1,8-naphthalic anhydride has dissolved, add 0.16 g butyl amine (2.2 mmoles, mw=73.14) For ease of handling, add 0.2 ml of butyl amine directly through the reflux condenser. Allow the reaction to reflux for 12-24 hours. Allow the reaction mixture to cool to room temperature. The reaction can sit until your next day in the lab. Determine the extent of the reaction by TLC on normal phase TLC with 50:50 hexane:ethyl acetate as the solvent system. The product should NOT be fluorescent when viewed under blue (450 nm) light. The end product is expected to result in a more hydrophobic trimer.

Example 16—Addition of Trimeric Jeffamine T-403 to the Reaction Mixture of Example 15

Return the reaction mixture to reflux. Add 0.316 grams of Jeffamine 1-403 (0.72 mmoles, mw=440) directly through the condenser. Add 0.22 g TEA (2.2 mmoles, mw=101) directly through the condenser. Allow the reaction to reflux for 48-72 hours. Allow the reaction mixture to cool to room temperature. The reaction can sit until your next day in the lab. If crystals or oil forms, collect by filtration or decanting. If there is no apparent product, add 100 ml of water and cool at 4° C. to bring the product out of solution. The end product is expected to result in a more hydrophobic trimer.

Example 17—Characterization of Product from Example 16

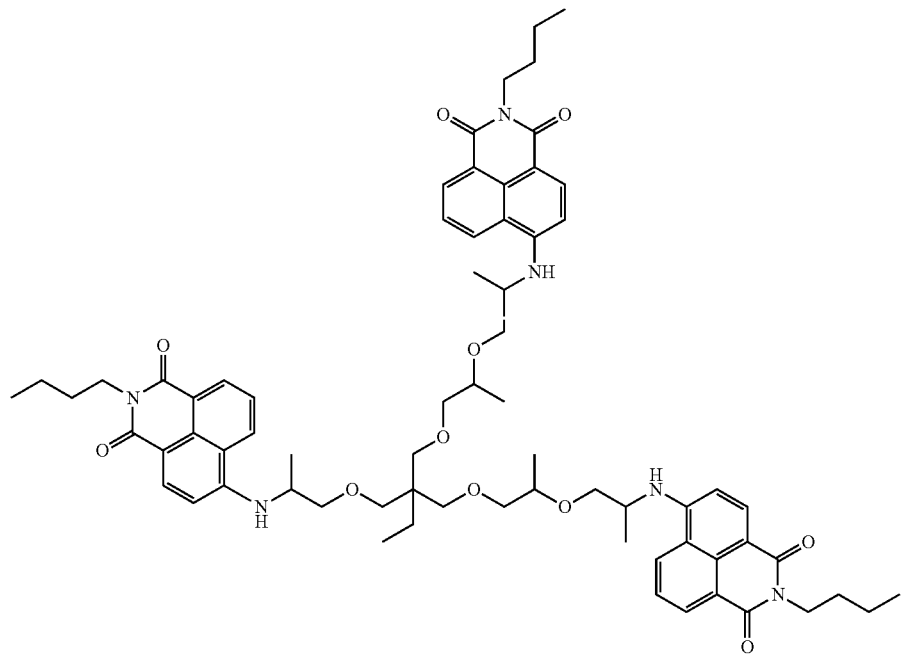 [SMILES: CCCCN1C(=O)c2cccc3c(NC(C)COCC(CC)(COCC(C)OCC(C)Nc4ccc5c6c(cccc46)C(=O)N(CCCC)C5=O)COCC(C)OCC(C)Nc4ccc5c6c(cccc46)C(=O)N(CCCC)C5=O)ccc(c23)C1=O]

Estimate the purity by TLC on normal phase TLC with 50:50 hexane:ethyl acetate as the solvent system. The product should be fluorescent when viewed under blue (450 nm) light.

Estimate the aqueous solubility by adding small aliquots of product to 10 ml of PBS with vigorous stirring. When the solution appears to be saturated and in equilibrium with solid product (or oil), continue to stir for 30 minutes. Then allow to settle for 30 minutes and then measure the absorbance at 440 nm. Make serial 1:10 dilutions in PBS if the measured absorbance is above 1.

Example 18—Synthesis of Boc-Protected Jeffamine—148

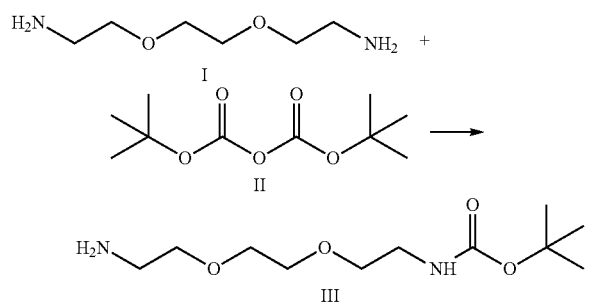

Jeffamine-148 (I) was dissolved in THF and cooled to 0° C. in an ice bath while stirring. Boc-anhydride (II), 0.5 molar equivalent, was dissolved in an equal volume of THF and added dropwise to the cooled solution. The drop rate was monitored to ensure the reaction temperature did not rise above 5° C. Upon completion of the Boc-anhydride addition, the reaction vessel was removed from the ice bath and allowed to warm to room temperature. The reaction was stirred at room temperature overnight. An equal volume of saturated NaCl was added to the reaction mixture and extracted three times with $CH_2Cl_2$. The organic layer was dried over anhydrous $MgSO_4$, filtered, and the solvent evaporated to leave the product as an oil. The crude product was chromatographed on silica gel eluting with a 10:4:1 solvent mixture of $CH_2Cl_2$:$CH_3OH$:$NH_4OH$. LCMS, APCl ionization—gives a product with mass of 248 (M+H=249).

$^1$HNMR Analysis (Integrations in Parentheses)—

The singlet at 1.4 ppm (9H) was due to the Boc group. The triplet at 2.85 ppm (2H) was the $H_2NCH_2$— group. The broad singlet at 3.3 ppm (2H) was due to the —$NH_2$ group. The complex signal at 3.5 ppm (4H) was due to the —(CO)$NCH_2CH_2O$— groups, which were not identical but overlap significantly at 400 MHz. The signal at 3.55 ppm (2H), partially overlapping the signal at 3.5 ppm was due to the $H_2NCH_2CH_2O$— group. The signal at 3.6 ppm (4H) was the —$OCH_2CH_2O$— group. The signal at 7.24 ppm was residual solvent.

Example 19—Synthesis of 4-chloro-N-Boc-Jeffamine Naphthalimide (V)

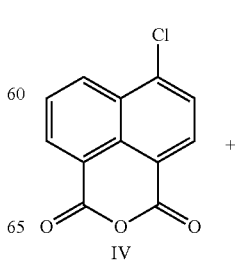

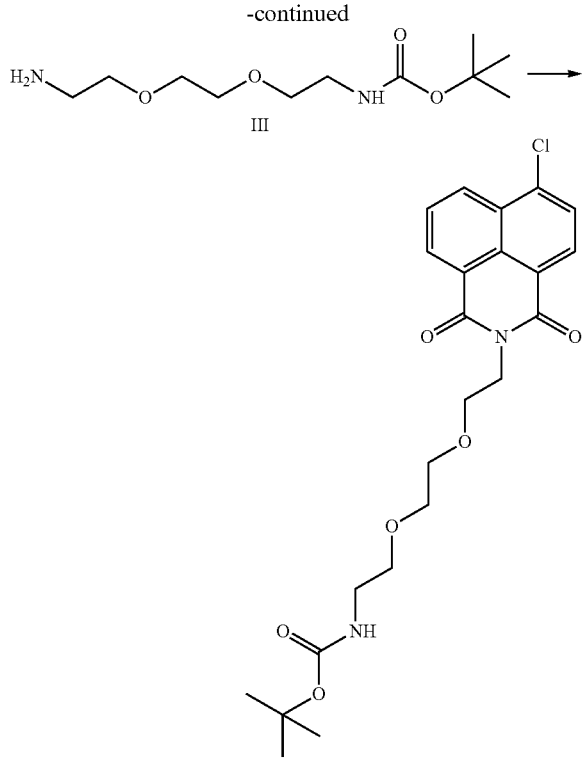

4-chloro naphthalic anhydride (IV) was suspended with stirring in 3A sieve dried ethanol and heated to 55° C. Boc-Jeffamine (III), 1 molar equivalent, was added dropwise to the suspension. The heat was increased to 85° C., excess triethylamine was added in one portion, and the reaction was stirred overnight. The reaction was cooled and the solvent evaporated. The crude reaction mixture was chromatographed on silica gel eluting with $CH_2Cl_2$.

$^1$HNMR Analysis (Integrations in Parentheses)—

Analysis of the region from 1.4-4 ppm was similar to the Boc-Jeffamine analysis above. The signal at 1.4 ppm (10H) was the Boc group, at 3.5 ppm (2H) is the —$(CO)_2NCH_2CH_2O$— group, at 3.6 ppm (2H) was the —$(CO)NHCH_2CH_2O$— group, at 3.65 ppm (2H) was the $(CO)NHCH_2CH_2O$— group, and at 3.85 ppm (4H) was the —$OCH_2CH_2O$— group. The signals were shifted slightly downfield due to the imide group. The most significant shift was the signal at 4.4 ppm (2H) due to the —$(CO)_2NCH_2CH_2O$— group. The aromatic region was characteristic of the 4-chloro-1,8-naphthalimide group. The complex signal at 7.85 ppm (3H) was due to the protons on the C2, C3, and C6 positions. The doublet at 8.5 ppm (1H) was due to the proton on the C5 position and the doublet of doublets at 8.65 ppm (1H) was due to the proton at the C7 position. The signal at 1.6 ppm was due to residual water and the signals at 2.0 ppm, 3.2 ppm, and 7.24 ppm were due to residual solvent.

Example 20—Synthesis of EDR-148 Terminated Head Linked T-403 Trimer

The 4-chloro-N-Boc-Jeffamine Naphthalimide was used._In particular, the product of example 21 was used without purification. The reaction volume was reduced to 20 ml and 2 mL of this solution was added to 10.0 mL of three different solvents: dimethylformamide (DMF), 1-butanol, and dimethylsulfoxide (DMSO). 0.132 g of JEFFAMINE® T-403 (mw=440) was added directly through the condenser. The reaction refluxed for 24 hours. The condenser was removed from the flask to evaporate any excess ethanol, which would lower the boiling point. The condenser was attached again and the reaction refluxed for 6 days before being analyzed on HPLC, UV-Vis, and TLC.

TLC—

The solution with the 1-butanol was a dark amber color, but the final product did not fluoresce indicating that the desired product did not form. The solution with the DMSO was dark amber and very viscous but the final product did not fluoresce indicating that the desired product did not form.

The solution with the DMF was also a dark amber, the reaction went to completion indicated by the presence of a visibly fluorescenct product and the UV-vis results. A mixture of products was made. The TLC plate showed two bright green spots at Rfs of 0.52 and 0.76. The 0.52 spot is hypothesized to be either a monomer or dimer product, as shown below.

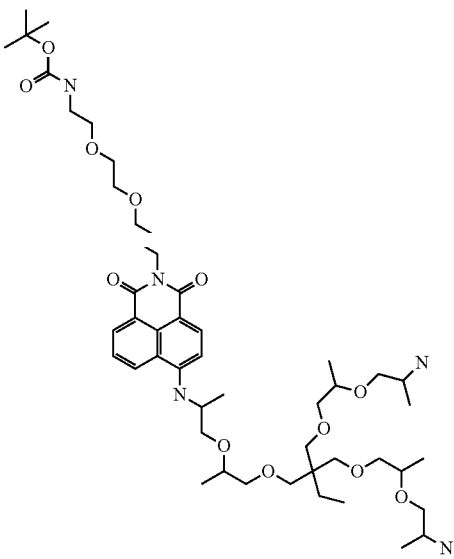

monomer product
Formula Weight: 906.16(4)
Exact Mass: 905.57252303(4)
Formula: $C_{47}H_{79}N_5O_{12}$

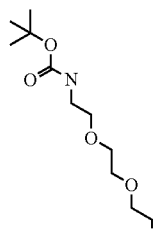

45
-continued
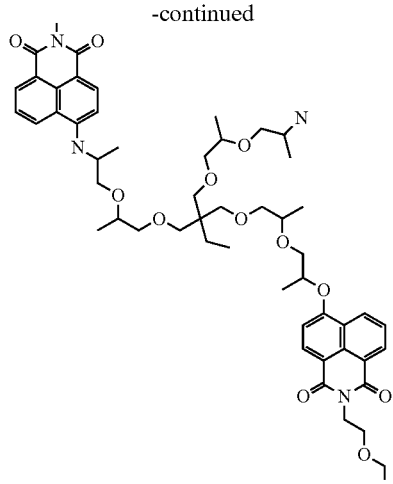
46
-continued
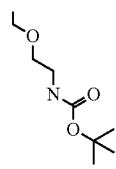
dimer product
Formula Weight: 1332.62(6)
Exact Mass: 1331.75160960(5)
Formula: $C_{70}H_{105}N_7O_{18}$
The 0.76 spot was concluded to be either the dimer product shown above or a trimer product shown below.
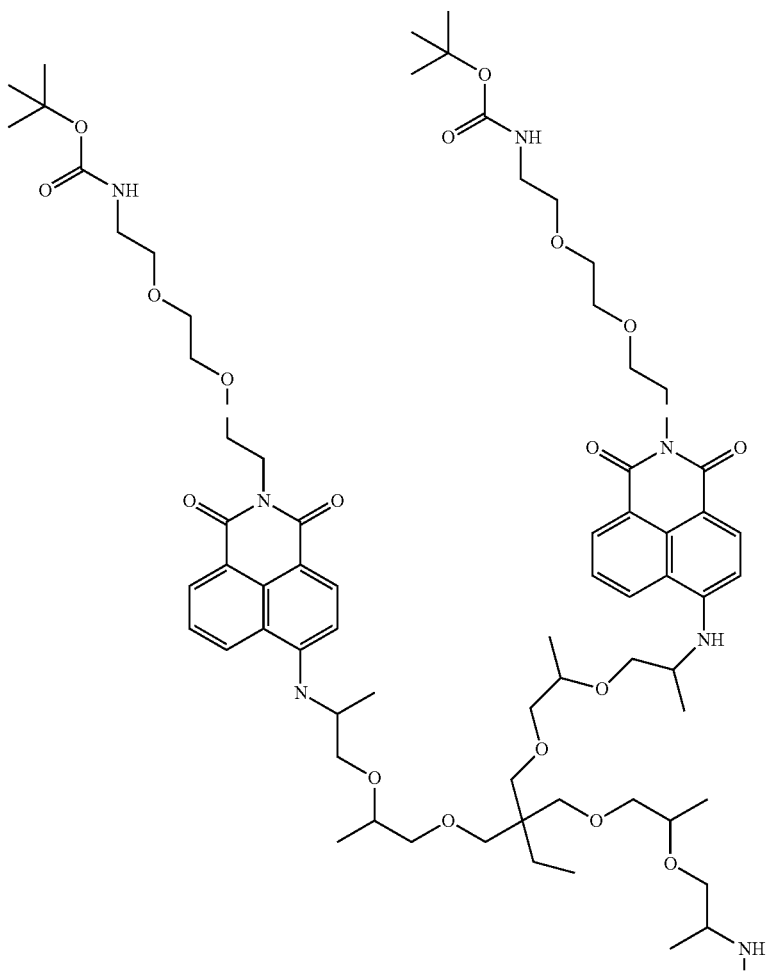

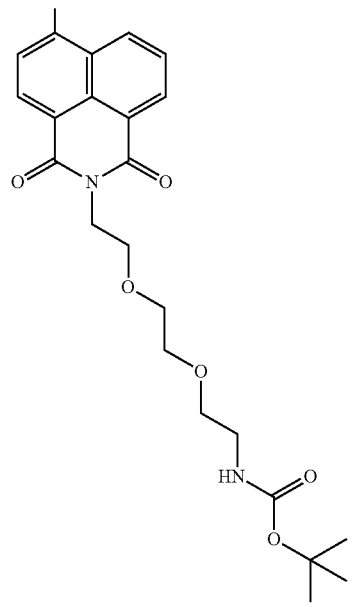

trimer product
Formula Weight: 1759.08(8)
Exact Mass: 1757.93069618(6)
Formula: $C_{93}H_{131}N_9O_{24}$ UV-Vis—

The 1-butanol solvent product was tested. The spectrum showed that the solution looked almost identical to the intermediate. There were large peaks at 280, 340, and 360 nm. The only difference was that there was a small peak at 440 nm. It could be concluded that the reaction did not go to completion due to the solvent's low boiling point.

The DMF solvent results showed peaks only at 280 and 435-445 nm. It can be concluded that the reaction when to completion because the 340 and 360 nm peaks disappeared and were replaced by the typical 435-445 nm peak indicating substitution in the 4 position of the naphthalimide.

HPLC:

The DMF product had the first major component at 6.9 minutes and a second major component at 8.7 minutes. The maximum absorbance was at 440 nm. The Rxn Trimer (1-butanol) had a major component at 9.4 minutes, which is the same as the intermediate. The maximum absorbance was at 340 nm. This is consistent with a completed reaction in the DMF solvent (no intermediates present) and an incomplete reaction in butanol (intermediates still present). The reaction in DMSO showed no absorbance peaks indicating a solvent ill-suited to the reaction.

Example 21—A Proposed Reaction Scheme for Forming a Naphthalimide Complex

Step 1 is to perform Example 18.

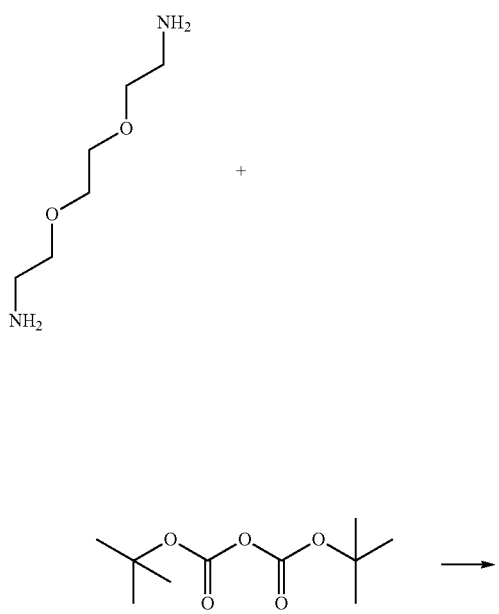

-continued
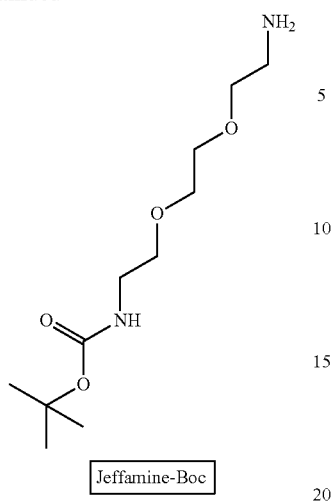
Jeffamine-Boc
-continued
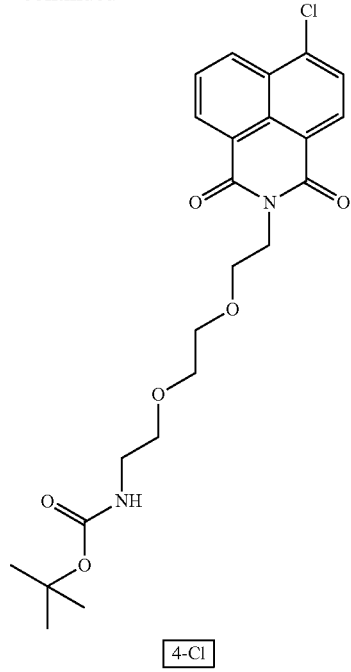
4-Cl
Step 2 is to perform Example 19
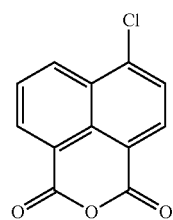
+
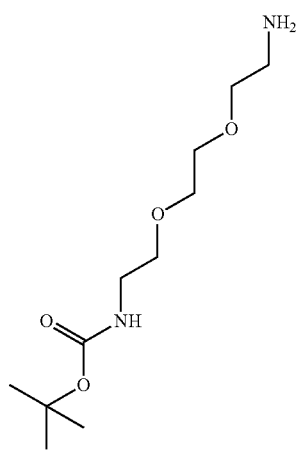
Step 3 is to combine a Boc-protected amino group, i.e., a linker (see Example 22 below) with a drug mimic
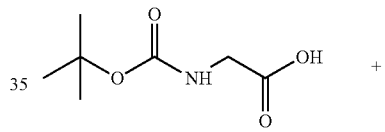
+
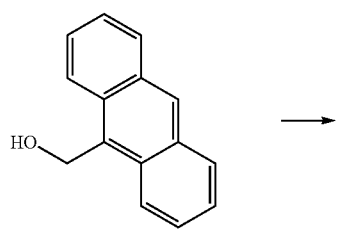
→
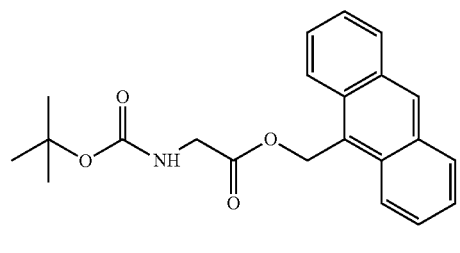
DCC
Step 4 is to couple the Boc-protected naphthalimide compound to the linker/drug perhaps by performing Example 23 or Example 24 below to form a naphthalimide complex for use in localized drug delivery.

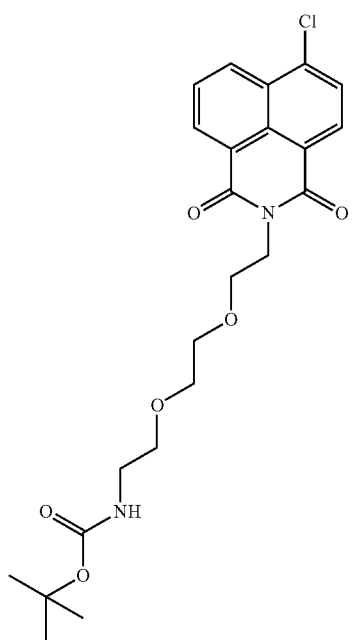

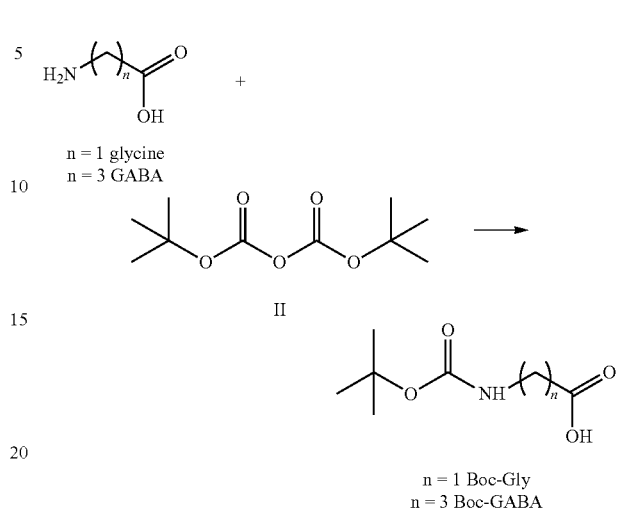

n = 1 glycine
n = 3 GABA

II n = 1 Boc-Gly
n = 3 Boc-GABA

Example 22—Boc Protection of Amino Acids

The amino acid, 0.10 mole (glycine or gamma amino butyric acid), was dissolved in 50 ml of water with stirring. Triethylamine, 3 mole equivalents was added in one portion. Boc anhydride (II), 1 mole equivalent, dissolved in DMF was added dropwise. The reaction was stirred overnight. The reaction mixture diluted with 600 mls water, cooled to 0° C., and the pH was adjusted to 2 with 6M HCl. The mixture was extracted with ethylacetate, the organic layer was washed with brine and dried over anhydrous $Na_2SO_4$. The organic layer was evaporated and the resulting oil crystallizes upon setting.

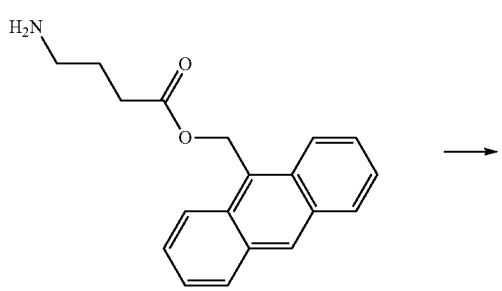

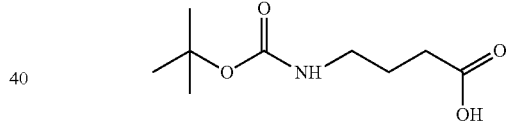

$^1$HNMR Analysis BocGABA (Integrations in Parentheses)—

The signal at 1.3 ppm (9H) was the Boc group. The multiplet at 1.57 ppm (2H) was the —$CH_2CH_2CH_2$— group. The triplet at 2.15 ppm (2H) was the —$CH_2CH_2COOH$ group. The triplet at 2.8 ppm (2H) was the $ROOCNHCH_2$— group. The signal at 6.8 ppm (1H) was the carboxylic acid proton in DMSO solvent. The singlet at 2.45 ppm was residual DMSO.

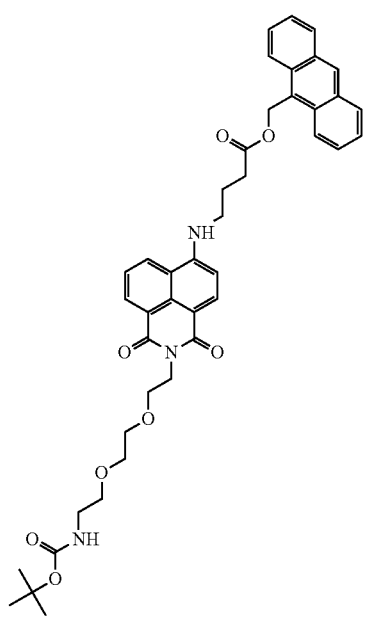

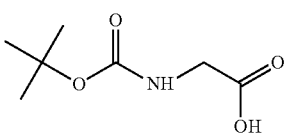

$^1$HNMR Analysis BocGlycine (Integrations in Parentheses)—

The signal at 1.4 ppm (10H) was the Boc group. The complex signal at 3.8-3.9 ppm (2H) was the —$NHCH_2COOH$ group. The broad singlet at 10.15 ppm (1H) was the carboxylic acid proton. Signals at 2.8 ppm, 2.9 ppm, and 8 ppm were due to residual DMF. The signal at 7.24 ppm was residual CHCl₃.

Example 23—the Yamaguchi Coupling of Amino Acids and Alcohols

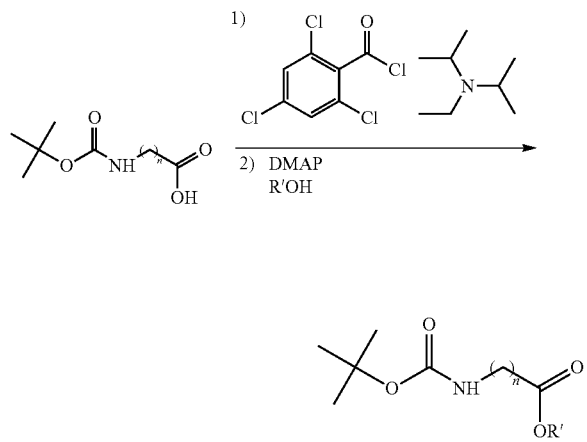

n = 1 Boc-Gly  R' = benzyl, 3-phenylpropyl
n = 3 GABA
n = 1 Boc-Gly benzyl ester, 3-phenylpropyl ester
n = 3 GABA benzyl ester, 3-phenylpropyl ester The N-Boc protected amino acid was dissolved in toluene or benzene. Diisopropylethylamine, 3 mole equivalent, and 2,4,6-Trichlorobenzoyl chloride, 1.33 molar equivalent, were added to the stirred solution. The reaction was stirred at room temperature for 6 hours. The alcohol dissolved in a minimum amount of solvent was added dropwise to the stirred solution followed by addition of DMAP (dimethylaminopyridine) dissolved in a minimum amount of solvent in one portion. The reaction was stirred for 3 hours. An equal volume of saturated $NH_4Cl$ was added, the reaction mixture filtered and extracted with ethylacetate. The organic layer was dried over anhydrous $MgSO_4$ or $Na_2SO_4$, filtered, and the solvent evaporated. The crude reaction product was chromatographed on silica eluting with ethylacetate or $CH_2Cl_2$.

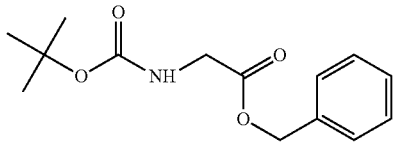 [SMILES: CC(C)(C)OC(=O)NCC(=O)OCc1ccccc1]

$^1$HNMR analysis N-Boc Benzyl Glyconate. This is a spectrum on the crude reaction mixture of benzyl alcohol and Boc-glycine using the Yamamguchi process. The Boc region (1.4 ppm) showed two peaks as not all Boc-glycine was reacted. The region from 5-5.3 ppm due to the benzyl protons showed two singlets, confirming the incomplete reaction. The shift of the glycine —CH₂— group and the multiple signals for the Boc and benzyl groups confirmed that the Yamaguchi reaction was successful, though incomplete.

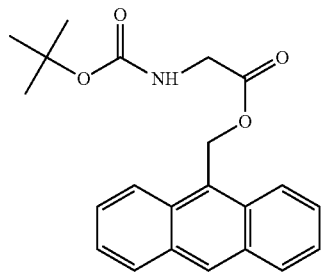 [SMILES: CC(C)(C)OC(=O)NCC(=O)OCc1c2ccccc2cc2ccccc12]

$^1$HNMR Analysis N-Boc Anthryl Glyconate (Integrations in Parentheses)—

The signal at 1.4 ppm (9H) was due to the Boc group. The broad signal at 4.4 ppm (2H) was due to the glycine —CH₂— group. The signals at 6.2 ppm (1H) and 6.4 ppm (1H) were due to the "benzylic"-CH₂— group. The signals from 7.4-8.5 ppm were characteristic of a 9-substituted anthracene. The less than optimal integration ratios was due to difficulties in separating the product from the anthrylmethanol. The signals at 1.2 ppm, 2.0 ppm, 2.1 ppm, and 2.3 ppm were residual solvents. The signal at 7.24 ppm was residual CHCl₃

Example 24—the Fisher Esterifcation of Amino Acids and Alcohols

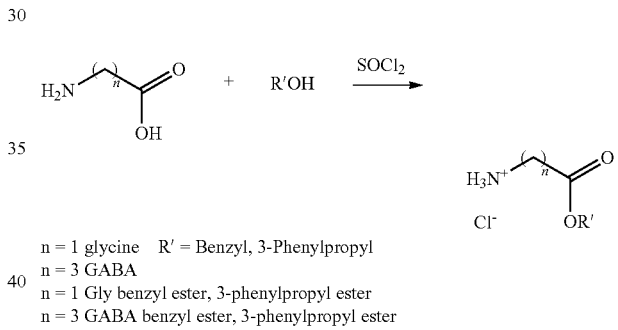

n = 1 glycine  R' = Benzyl, 3-Phenylpropyl
n = 3 GABA
n = 1 Gly benzyl ester, 3-phenylpropyl ester
n = 3 GABA benzyl ester, 3-phenylpropyl ester The amino acid was suspended in the alcohol, 50 mole equivalents, and cooled to 0° C. while stirring. Thionyl chloride, 5 mole equivalents, was added dropwise to the cooled solution. The drop rate was monitored to ensure the temperature does not exceed 10° C. Upon completion of the thionyl chloride addition, the reaction was heated at 95° C. for 5 hours. The reaction mixture was cooled to room temperature, then placed in an ice bath and ethyl ether added until the solution turned turbid. This typically required 5× the volume of alcohol used. The mixture was allowed to set at 0° C. for an hour and filtered. The crude product was recrystallized from ethanol and ethyl ether.

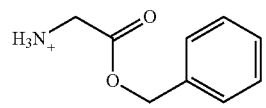 [SMILES: NCC(=O)OCc1ccccc1]

$^1$HNMR Analysis Benzyl Glycinate (Integrations in Parentheses)—

The singlet at 3.8 ppm (2H) is the $ROOCCH_2NH_3^+$ group. The singlet at 5.15 ppm (2H) was the benzylic group. The multiplet at 7.3 ppm (5H) was the aromatic system. The broad singlet at 8.6 ppm (3H) was the ammonium group. The signal at 2.4 ppm was residual DMSO and the signal at 3.33 ppm was residual water.

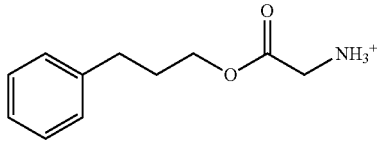 [SMILES: [NH3+]CC(=O)OCCCc1ccccc1]

¹HNMR Analysis 3-Phenylpropyl Glycinate (Integrations in Parentheses)—

The multiplet at 1.8 ppm (2H) was the ArCH₂CH₂CH₂O— group. The triplet at 2.6 ppm (2H) was the benzyl group. The singlet at 4.0 ppm (2H) was the ROOCCH₂NH₃⁺ group. The triplet at 4.1 ppm (2H) was the ArCH₂CH₂CH₂O— group. The complex doublet at 7-7.3 ppm (5H) was the aromatic system. The broad singlet at 8.6 ppm (3H) was the ammonium group.

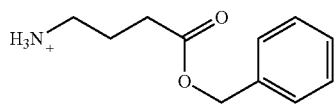 [SMILES: NCCCC(=O)OCc1ccccc1]

¹HNMR Analysis Benzyl GABA (Integrations in Parentheses)—

The multiplet at 1.8 ppm (2H) was the —CH₂CH₂CH₂— group. The triplet at 2.45 ppm (2H) was the —CH₂CH₂CH₂COOR group. The triplet at 2.8 ppm (2H) was the —CH₂CH₂CH₂NH₃⁺ group. The singlet at 5.0 ppm (2H) was the benzylic group. The broad signal at 7.3 ppm (5H) was the aromatic system. The broad singlet at 8.15 ppm (3H) was the ammonium group.

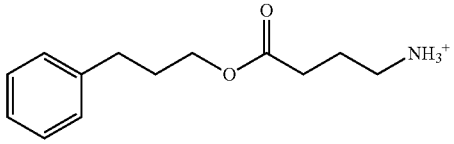 [SMILES: [NH3+]CCCC(=O)OCCCc1ccccc1]

¹HNMR Analysis 3-Phenylpropyl GABA (Integrations in Parentheses)—

The multiplet at 1.9 ppm (2H) was due to the BzCH₂CH₂CH₂O— group. The multiplet at 2.1 ppm (2H) was due to the ROOCCH₂CH₂CH₂NH₃⁺ group. The triplet at 2.4 ppm (2H) was the ROOCCH₂CH₂CH₂NH₃⁺ group. The tripet at 2.6 ppm (2H) was the BzCH₂CH₂CH₂O— group. The complex group at 3.1 ppm (2H) was the ROOCCH₂CH₂CH₂NH₃⁺ group. The triplet at 4.0 ppm was the BzCH₂CH₂CH₂O(O)C— group. The complex doublet at 7.1-7.3 ppm (5H) was the aromatic system and the broad singlet at 8.2 ppm (3H) was the ammonium group.

Example 25—Linker Attachment to 4-Cl (V)

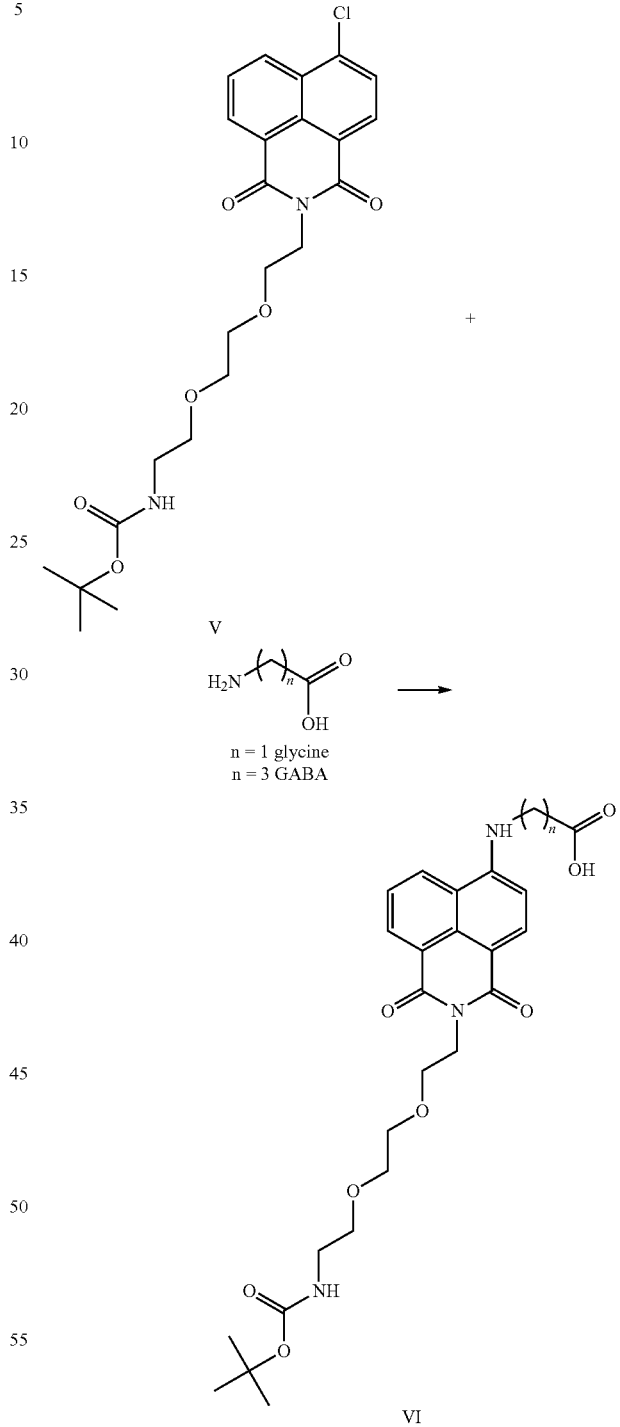

4-chloro-N-Boc-Jeffamine-1,8-naphthalimide was dissolved in boiling methanol. The amino acid, 1 mole equivalent, was dissolved in water and 1.5 mole equivalent Na₂CO₃ added to the aqueous solution. The aqueous solution of the amino acid was added to the boiling methanol solution and the mixture refluxed for 30 minutes. The reaction was cooled and the pH adjusted to pH=3-4 with 10% HCl. The solution was extracted with ethylacetate, the organic layer dried, and evaporated.

Example 26—Linker Solution Hydrolysis

The hydrolysis rate of a linker was studied without attachment to a naphthalimide compound or tissue attachment under physiological conditions. The work verified the expected hydrolysis rate and when combined with ex vivo data allows the influence of the tissue on the hydrolysis rate to be determined.

The ex-vivo studies using porcine arteries were completed with the presence of antibiotics to prevent microbial growth over the time course of the study (100 U/ml penicillin, 100 μg/ml streptomycin and 50 μg/ml gentamicin). The rate of hydrolysis was studied in the presence and absence of this antibiotic cocktail to verify that no effect is seen on the hydrolysis rate and no interference in the analytical method was seen.

Samples—

FEG (FITC modified with ethanolamine linked to GABA) (5-[2-(4-aminobutanoyloxy)ethylcarbamothioylamino]-2-(3-hydroxy-6-oxo-xanthen-9-yl)benzoic acid)) in PBS at 37° C.

FEG in PBS at 37° C. in the presence of 100 U/ml penicillin, 100 μg/ml streptomycin and 50 μg/ml gentamicin.

Sample Preparation

A 20 mg/mL stock solution of a drug mimic, such as an FITC derivative, was prepared by weighing out approximately 20 mg of material and diluting with 1 mL of H20. The release rate of each compound, the free mimic from its respective linker, was studied in duplicate as a function of time and pH (phosphate buffered saline (PBS) at pH=1, pH=7.4, and pH=10). The starting concentration for each preparation was 400 μg/mL of drug mimic with attached linker (20 μL of stock solution diluted with 980 μL of hydrolysis PBS). In order to more accurately mimic clinical conditions samples were prepared and stored in a 37° C. oven with slow agitation using a rotating mixer until analyzed using HPLC. The concentration of the target complex was determined in duplicates at multiple time points (t=0, 8, 24, 48, 72, 144, 216 hours) using the HPLC conditions below and quantitation using a standard curve. A 2 mg/mL stock solution of the target complex was prepared by weighing out approximately 20 mg of target complex and diluting with 10 mL of $H_2O$. The following concentrations from the stock solution were prepared by performing serial dilutions in $H_2O$:

| Standard | Standard Concentration | Preparation |
|---|---|---|
| A | 200 | 100 μL stock + 0.9 mL $H_2O$ |
| B | 100 | 500 μL Standard A + 500 μL $H_2O$ |
| C | 50 | 500 μL Standard B + 500 μL $H_2O$ |
| D | 10 | 200 μL Standard C + 800 μL $H_2O$ |
| E | 5 | 500 μL Standard D + 500 μL $H_2O$ |
| F | 1 | 200 μL Standard E + 800 μL $H_2O$ |

Figure 15A:
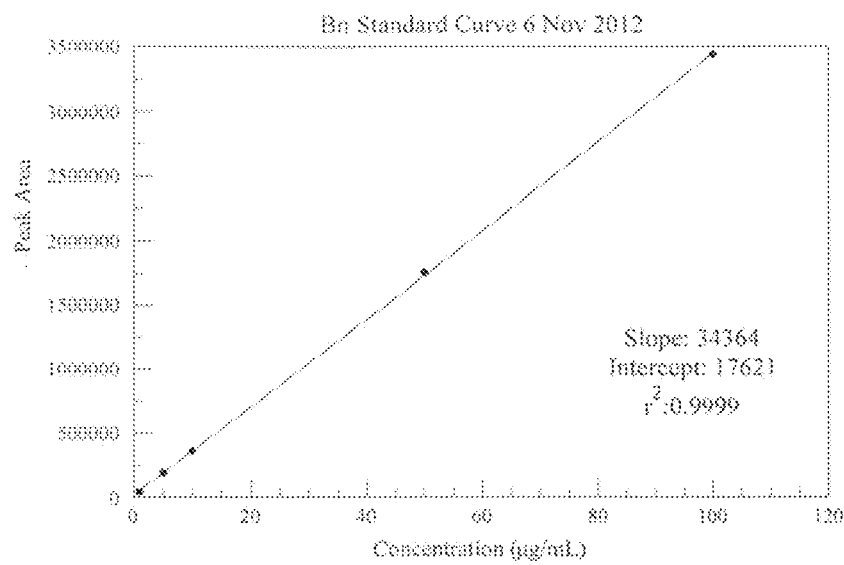
FIG. 15A shows the standard curve of the benzyl alcohol drug mimic.

Quantitation using a standard curve was used to determine the amount of drug mimic released (μg) at each time point and duplicate sample preparations at each time point were averaged. FIG. 15A shows the standard curve of the benzyl alcohol drug mimic. The detection limit of the method was 1 μg/mL. The standard curve for 3-phenylpropanol was also linear over the range of 1 μg/mL to 100 μg/mL with a detection limit of the method at 1 μg/mL.

Figure 15B:
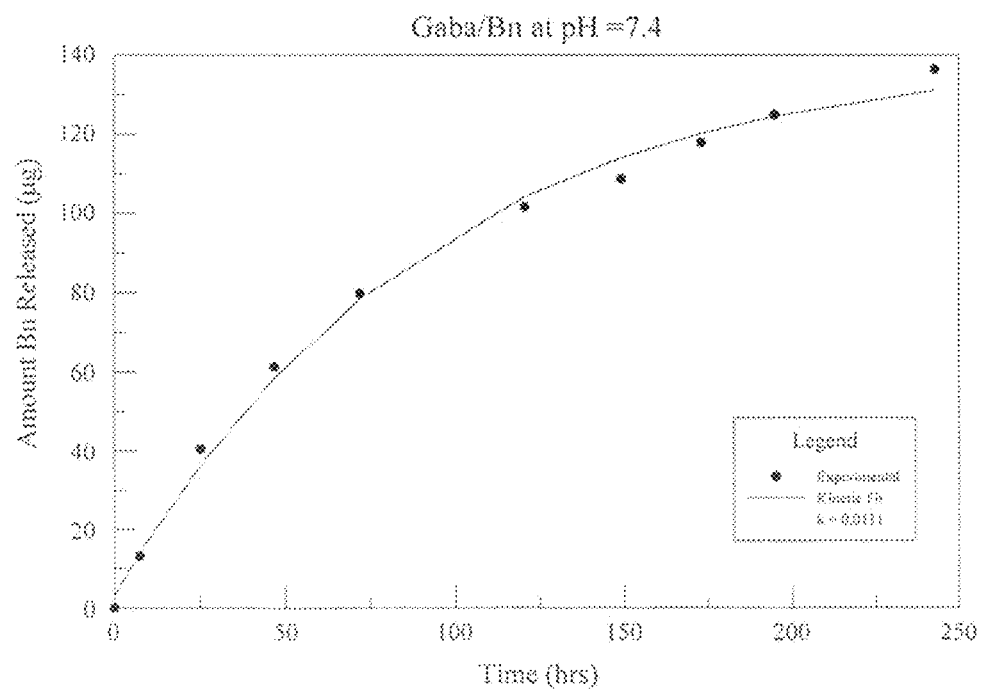
FIG. 15B shows a sample kinetic curve for free Bn and 3PP.
Figure 16:
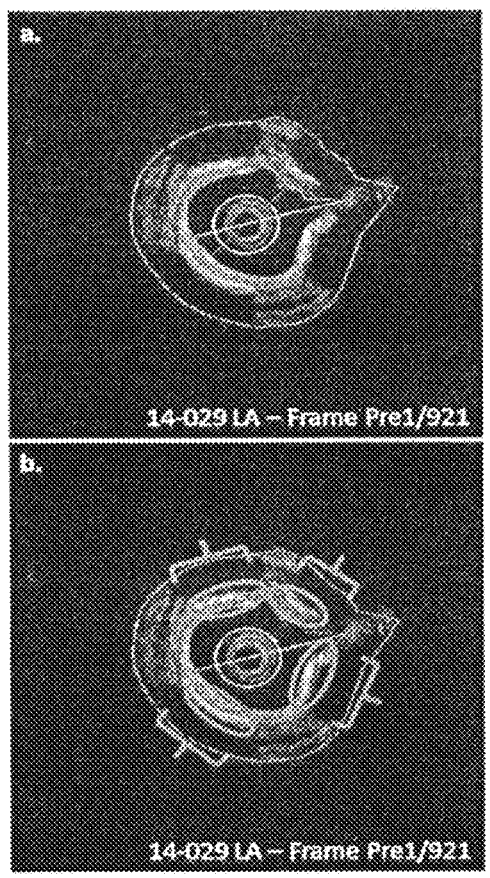
FIG. 16 are IVUS images illustrating a blood vessel wall and areas of plaque in the same artery.

Using the HPLC release data calculated for the free Bn and 3PP, shown below, kinetic curves were plotted (concentration vs time) for each compound using PSI Plot. The concentration was fit to a first order kinetic equation, where $C_T = C_F - C_c e^{-kt}$ ($C_T$ is the concentration at each time point (μg), $C_F$ is the final concentration (μg), $C_c$ is the change in concentration (μg), and k is the rate constant ($hr^{-1}$). If the reaction rate didn't display first order kinetics (ie: there was a systematic deviation between the experimental points and the calculated rate constant) other kinetic models were examined. Typically data was collected until at least 90% of the expected product was released. A sample kinetic curve is shown in FIG. 15B.

The HPLC method was able to determine the identity of each compound and the component linker and drug mimic by the retention time as shown in the Table below.

Analytical Column: Alltima HP Rocket C18 3μ 53 mm×7 mm

Mobile Phase: A: 0.1% Trifluoroacetic acid(aq) (TFA), B: 9:1 Acetonitrile:Water (0.1% TFA)

Gradient: 95% A hold for 1 minute, then ramp to 65% B at 7 minutes, hold for 0.5 minutes (Equilibration time 5 minutes)

Detector: PDA detector at 440 nm Fluorescence detector excitation wavelength at nm emission wavelength at nm Injection Volume: 20 μL Flow Rate: 2.5 mL/min

| Compound | Retention Time (minutes) |
|---|---|
| Bn | 3.9 |
| GABA/Bn | 4.5 |
| Gly/Bn | 3.7 |
| 3PP | 5.4 |
| GABA/3PP | 5.3 |
| Gly/3PP | 4.7 |

Bn = benzyl alcohol
GABA = γ-aminobutytic acid
Gly = glycine
3PP = 3-phenylpropanol Using the concentration versus time data, a rate constant was calculated for each compound at various pHs. A summary of that data is presented in the Table below. From this data, it is apparent that the GABA linker provides rate constants consistent with the desired release rate. The enhanced rate for the hydrolysis of the Gly/Bn is likely due to the formation of an internal 5 membered ring that would be autocatalytic.

| Structure | Name | pH 1 | pH 7.4 | pH 10 |
|---|---|---|---|---|
| phenethyl ester of GABA | GABA/3PP | 0.034 | 0.010 | 0.124 |
| phenethyl ester of Gly | Gly/3PP | 0.004 | 0.082 | 0.155 |
| benzyl ester of GABA | GABA/Bn | 0.026 | 0.011 | 0.226 |
| benzyl ester of Gly | Gly/Bn | 0.002 | 0.311 | 0.156 |

Ex Vivo Release

The ex vivo release studies can be conducted using slaughterhouse porcine carotid arteries according to the following procedure. It can be expected that this work would demonstrate photochemical attachment of the pharmacological agent and subsequent hydrolytic cleavage releasing the drug mimic (FITC).

Sample Preparation

A section of fresh carotid artery (~4×20 mm) can be filled (~0.25 ml) with a 1 mM solution of the target solution and allowed to soak for a period of five minutes. The solution can be prepared fresh before each use as hydrolysis of the ester occured in the prepared solution. After the soak, the solution can be removed and retained for a concentration determination. This would set a baseline of the amount of material that entered the blood vessel and would be available for photochemical attachment for later calculation of efficiency. The complex can be photochemically activated, 450 mW of 450 nm light distributed by a radially emitting fiber placed inside a clear catheter for 60 seconds. The blood vessel can be quickly rinsed in PBS. The arterial wall can be cut lengthwise and the wall thickness recorded. Four sections of the artery (~4×4 mm) can be cut from the artery and placed into separate vials containing 1 ml of PBS supplemented with antibiotics. The area of the remaining arterial segment can be measured and then placed into a vial containing 5 ml of PBS supplemented with antibiotics. The PBS can be supplemented with antibiotics to prevent microbial growth over the study time. (100 U/ml penicillin, 100 μg/ml streptomycin and 50 μg/ml gentamicin.) All samples can be gently agitated at 37° C.

The larger sample can be used for hydrolytic release studies as monitored by HPLC. Sampling can occur over the course of four days. 100 μL of sample can be removed, the protein can be precipitated and filtered through a 0.22 μm filter. The samples can then be immediately analyzed for both the target complex as well as the modified FITC derivative. Appropriate recovery studies can be undertaken.

The data can be used to determine the hydrolysis rate as well as the efficiency of attachment. It can be expected that the complex, the mimic and a family of compounds from side reactions would be detected.

In Vivo Release

The intent of this study can be to provide in vivo proof of concept showing delivery, photochemical attachment and subsequent hydrolytic release. This data can be the estimation of parameters to be used in following studies. The following treatment groups will be utilized:

| Treatment Groups | Rational | Light | Dark |
|---|---|---|---|
| Saline | This sample will address possible coloration due to injection trama | | √ |
| Drug Mimic 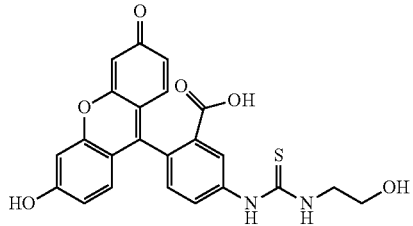 [SMILES: O=C(O)c1cc(NC(=S)NCCO)ccc1-c1c2ccc(=O)cc-2oc2cc(O)ccc12] | This sample will allow the measurement of the rate at which released drug mimic is cleared from the treatment area | | √ |
| Mimic + Linker 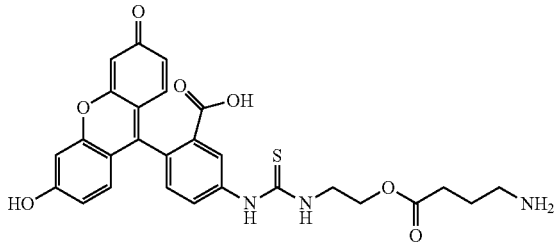 [SMILES: NCCCC(=O)OCCNC(=S)Nc1ccc(-c2c3ccc(=O)cc-3oc3cc(O)ccc23)c(C(=O)O)c1] | This sample will allow the measurement of the rate at which the unattached drug mimic/linker complex is cleared from the treatment area. The unattached drug mimic/linker complex would only be present as a result of a non-productive photo chemical reaction. | | √ |
| Mimic + Linker + Naphthalimide 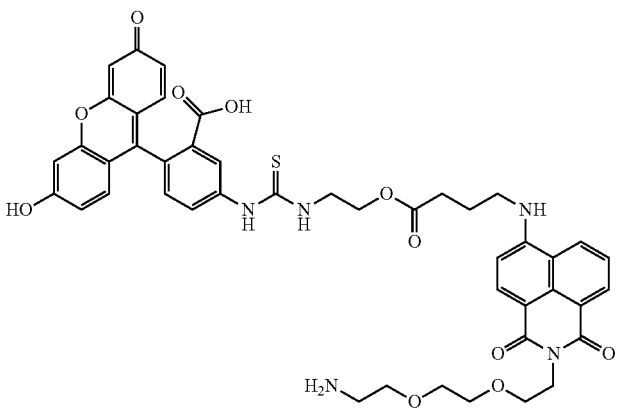 [SMILES: NCCOCCOCCN1C(=O)c2cccc3c(NCCCC(=O)OCCNC(=S)Nc4ccc(-c5c6ccc(=O)cc-6oc6cc(O)ccc56)c(C(=O)O)c4)ccc(c23)C1=O] | This is the drug delivery molecule which is capable of delivering and attaching the drug mimic + linker to the tissue. | √ | √ |
| Mimic + Linker + Naphthalimide 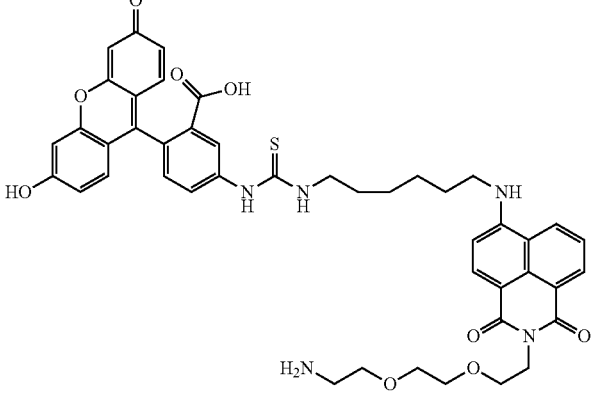 | This complex is identical to the compound above but without the cleavable linker. This will attach the drug mimic without the ability to hydrolytically release. The permanence of the drug mimic will be indicative of the underlying collagen stability. | √ | √ |

Hairless Sprague-Dawley rats will be injected sub dermally with 0.1 ml of a 1 mM solution of the target solution on the back. Animals will be lightly anesthetized with gas isoflurane to facility easier injection. 8-10 areas will be circled with surgical pens to identify the injection site. The solution will be allowed to equilibrate for 5 minutes and photos will be taken of the area. For a subset of the injection sites, the compound will be activated by exposure to 450 nm light evenly distributed over the injection area (1500 mW for 2 minutes). At 0, 24, 48, 72 and 96 hours, the rats will be anesthetized, photographed, and skin samples will be harvested. A biopsy punch will be used to take a sample around the injection site. The tissue will be blotted dry and subsequently homogenized in a minimal amount of PBS to produce a slurry that can be read in a plate reader. A serial dilution of 1 mM FITC will be used as the standard curve (1, 0.1, 0.01, 0.001, 0.0001, 0.00001, 0.000001, 0.000001, 0.0000001, 0.00000001). Other biopsy tissues will be analyzed by standard histological methods.

Example 27—IVUS Analysis of Human Cadaveric Arterial Samples

The following equipment was used in this Example: IVUS, Boston Scientific iLab 120 CARTR, UPN Product number: H749iLab120CARTRO, manufactured April 2011, Serial number 7347. The software is iReview version 1.0. The catheter is Boston Scientific Atlantis SR Pro 40 MHz Coronary Imaging Catheter, catalog number 38942, 3.6 F×135 cm.

IVUS images have identified different types of plaque, e.g., soft, mixed, hard, and calcified. M. Sahara, et al., "Soft Plaque Detected on Intravascular Ultrasound Is the Strongest Predictor of In-Stent Restenosis: an Intravascular Ultrasound Study," *European Heart Journal*, 25: 2026-2033 (2004), the disclosure of which is hereby incorporated by reference. For example, calcified plaque has been identified by two characteristics, i.e., a high echogenicity resulting in an intense reflection (bright white) and the presence of an acoustic shadow behind the plaque because the ultrasound cannot penetrate the calcified plaque. It has been found that treatment of a blood vessel comprising plaque, such as calcified plaque, with a plaque-softening compound of the present invention changed the echogenicity of the plaque, which is consistent with a change in the calcific nature of the plaque.

Postmortem diseased femoral arteries (both left and right) were received approximately 16 hours after the time of death. The samples were inspected to assess the level of disease. When palpated both the right and left arteries were extremely hard and rigid throughout the entire length of both arteries. Occlusion was visually judged as ranging from 20-60%. The artery was placed in PBS and IVUS pullback (0.5 mm/s) was completed three times (PRE 1, PRE 2, PRE 3). The artery was placed in a clean petri dish, filled with 2.5 mM of a composition comprising the disclosed plaque-softening compound, such as 4-amino-1,8-naphthalimide, and allowed to soak for 5 minutes. The artery was thoroughly rinsed with PBS to remove any excess plaque-softening compound. The artery was then placed into PBS and an IVUS pullback was conducted three times (SOAK 1, SOAK 2, SOAK 3). A balloon angioplasty catheter was placed into the artery and inflated to the reference vessel diameter (RVD) without any overstrech. A radially emitting light fiber was inserted into the catheter and centered in the angioplasty balloon. The composition was activated by exposure to blue light (447 nm) at an intensity of 1800 mW for 60 seconds. The balloon catheter was removed and an IVUS pullback was completed three times (POST 1, POST 2, POST 3). After treatment, the artery became more flexible and softer.

Figure 17:
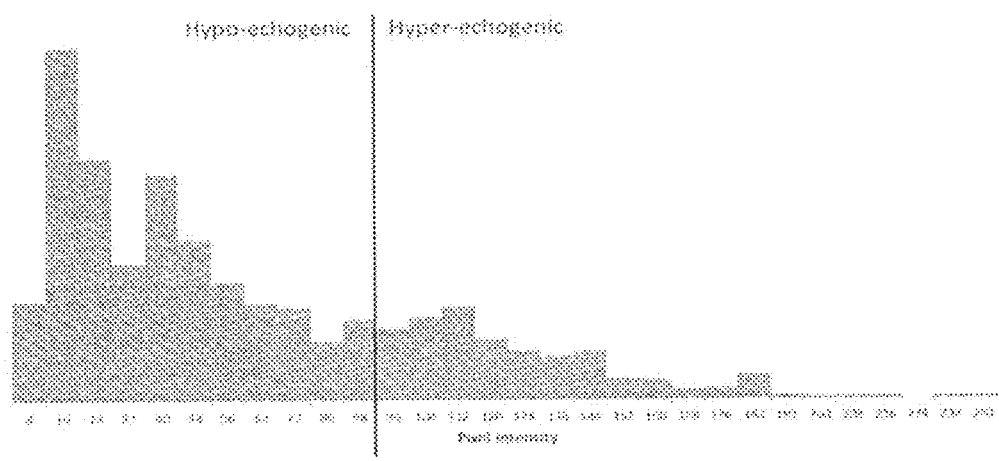
FIG. 17 is a histogram based on IVUS imaging of a blood vessel and illustrates the echogenicity of the blood vessel at frame 921.

Each frame of each pullback (PRE 1, PRE 2, PRE 3, SOAK 1, SOAK 2, SOAK 3, POST 1, POST 2, POST 3) was analyzed and calcified plaque was identified including the acoustic shadow behind each area of plaque. FIGS. 15a and 15b are the IVUS images from frame 921 of PRE 1 and illustrate the existence of plaque. For each frame, the intensity of each gray pixel (based upon 255 shades of gray, "AVI" format and 521×521 pixels) within the arterial wall was determined. FIG. 17 is a histogram illustrating the gray scale of frame 921, PRE 1, wherein the y-axis is the pixel count and the x-axis is the pixel intensity. So, for example, there were a lot of pixels having a pixel intensity of 16 and very few pixels having a pixel intensity of 168. It is known that the relative amount of hypo-echogenic and hyper-echogenic reflections can be used to measure the change in calcified plaque. See S. Brugaletta, et al., "Serial In Vivo Intravascular Ultrasound-Based Echogenicity Changes of Everolimus-eluting Bioresorbable Vascular Scaffold During the First 12 Months After Implantation," *JACC: Cardiovascular Interventions*, 4 (12):1281-1289 (2011), the disclosure of which is hereby incorporated by reference. For example, it is known that pixels with a gray scale intensity of 92 or lower were judged to be hypo-echogenic and those with a gray scale intensity of 93 or higher were judged to be hyper-echogenic. To be clear, in the instant Example, the mean gray value of the adventitia was used to classify tissue components as either hypo- or hyper-echogenic. One of ordinary skill in the art could easily determine the gray scale threshold for any data set in order to classify tissue components as either hypo- or hyper-echogenic.

The pixel intensity of the entire IVUS pullback data was analyzed as a single data set. The data indicated a relative shift of pixel intensity towards hypo-echogenicity, i.e., the number of pixels having a gray scale or 92 or lower was greater for the SOAK and POST IVUS pullbacks as compared to the PRE IVUS pullbacks. The ratio of hypo-echogenic to hyper-echogenic pixels, as shown below, increased with the SOAK and POST treatment, which indicated softening of the plaque.

| Treatment | Hypo-Echogenic pixels/Hyper-Echogenic pixels |
|---|---|
| PRE 1, PRE 2, PRE 3 | 4.320 |
| SOAK 1, SOAK 2, SOAK 3 | 4.699 |
| POST 1, POST 2, POST 3 | 5.011 |

Figure 18:
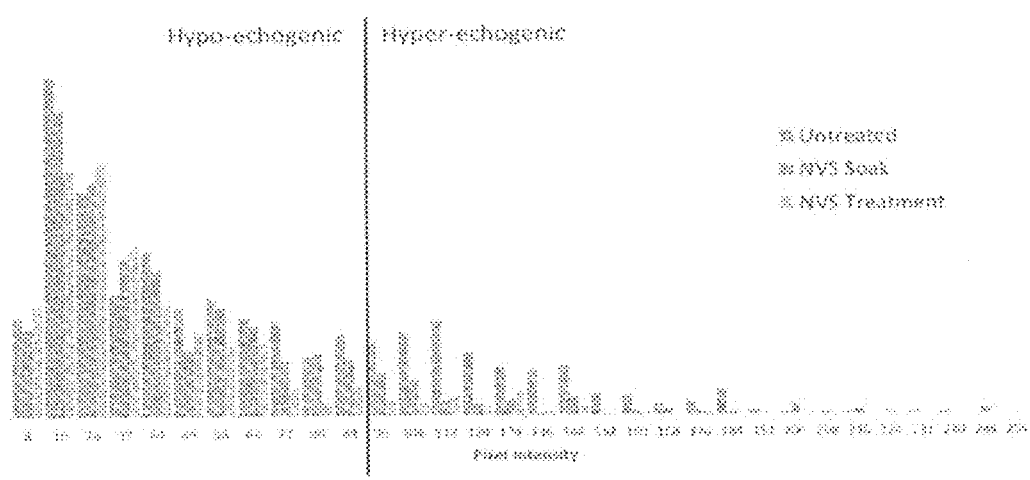
FIG. 18 is a histogram based on IVUS imaging of a blood vessel and illustrates the echogenicity of the blood vessel at frame 921, before treatment, after soak, and after full treatment.

A review of the POST 1, POST 2, and POST 3 IVUS images indicated that the plaque was not uniformly softened across the blood vessel. Areas of the arteries that were more effected by the treatment were further studied by conducting a single frame analysis. For example, the single frame analysis of frame 921 indicated the presence of calcified plaque in the untreated artery (PRE 1), wherein the intensity of the IVUS reflections was decreased after (SOAK 1), and further decreased after treatment with the light fiber (POST 1). FIG. 18 illustrates the histogram for this frame and displays a significant shift to hypo-echogenic values after both the SOAK and the Treatment. As can be seen from FIG.

18, the pixel count (y-axis) of hypo-echogenicity has increased after the SOAK and the Treatment as compared to the pixel count for the untreated (PRE). The ratio of hypo-echogenic to hyper-echogenic pixels at frame 921, as shown below, increased with the SOAK and POST treatment, which indicated softening of the plaque.

| Treatment | Hypo-Echogenic pixels/Hyper-Echogenic pixels |
|---|---|
| PRE 1, PRE 2, PRE 3 | 2.729 |
| SOAK 1, SOAK 2, SOAK 3 | 7.500 |
| POST 1, POST 2, POST 3 | 12.556 |

Figure 19:
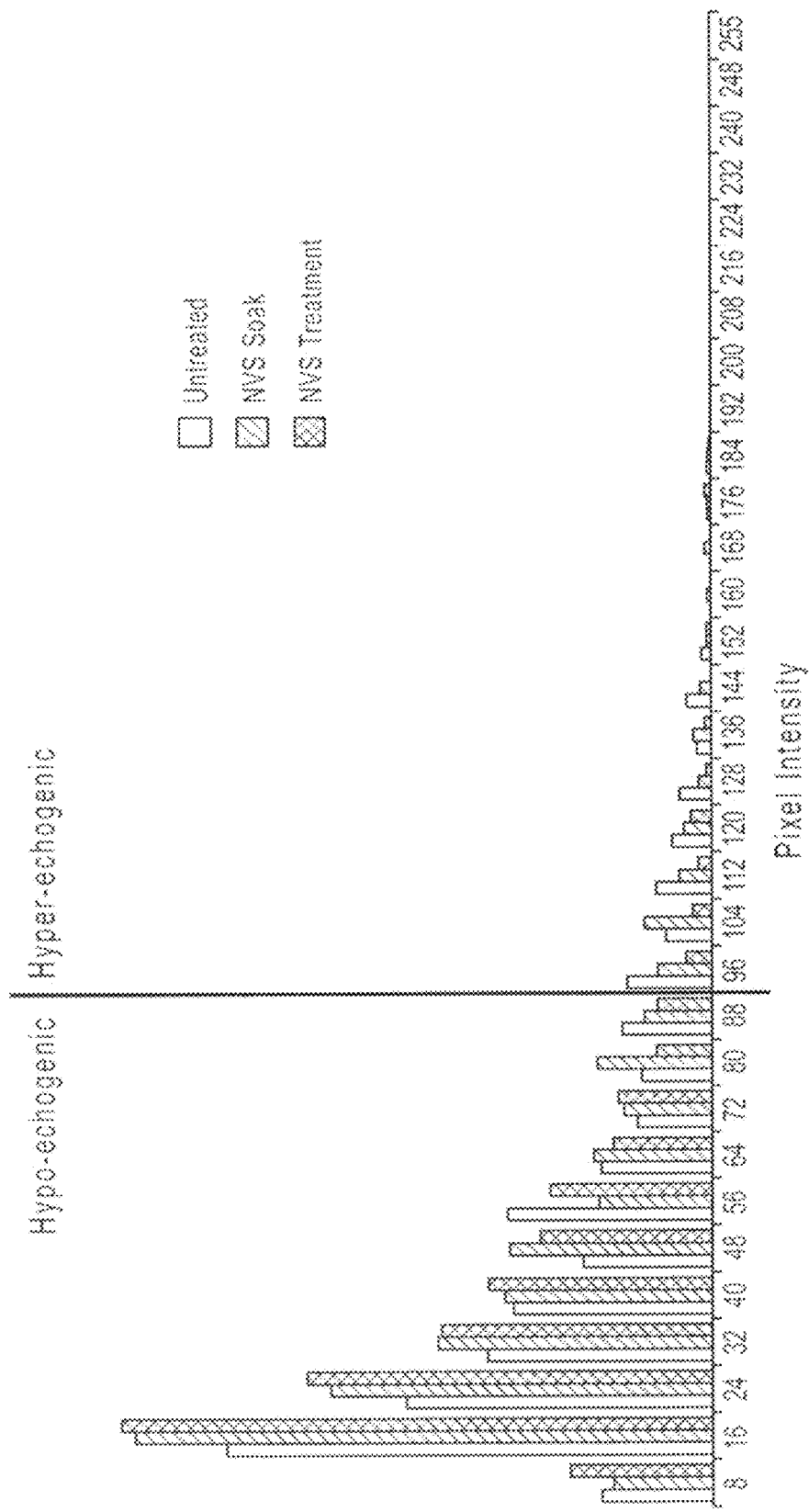
FIG. 19 is a histogram based on IVUS imaging of a blood vessel and illustrates the echogenicity of the blood vessel at frame 2925, before treatment, after soak, and after full treatment.

As another example, a single frame analysis of frame 2925 indicated the presence of calcified plaque in the untreated artery (PRE 1), wherein the intensity of the IVUS reflections was decreased after (SOAK 1), and further decreased after treatment with the light fiber (POST 1). FIG. 19 illustrates the histogram for this frame and displays a significant shift to hypo-echogenic values after both the SOAK and the Treatment. As can be seen from FIG. 19, the pixel count (y-axis) of hypo-echogenicity has increased after the SOAK and the Treatment as compared to the pixel count for the untreated (PRE). The ratio of hypo-echogenic to hyper-echogenic pixels at frame 2925, as shown below, increased with the SOAK and POST treatment, which indicated softening of the plaque.

| Treatment | Hypo-Echogenic pixels/Hyper-Echogenic pixels |
|---|---|
| PRE 1, PRE 2, PRE 3 | 6.297 |
| SOAK 1, SOAK 2, SOAK 3 | 9.043 |
| POST 1, POST 2, POST 3 | 21.050 |

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound selected from the group consisting of

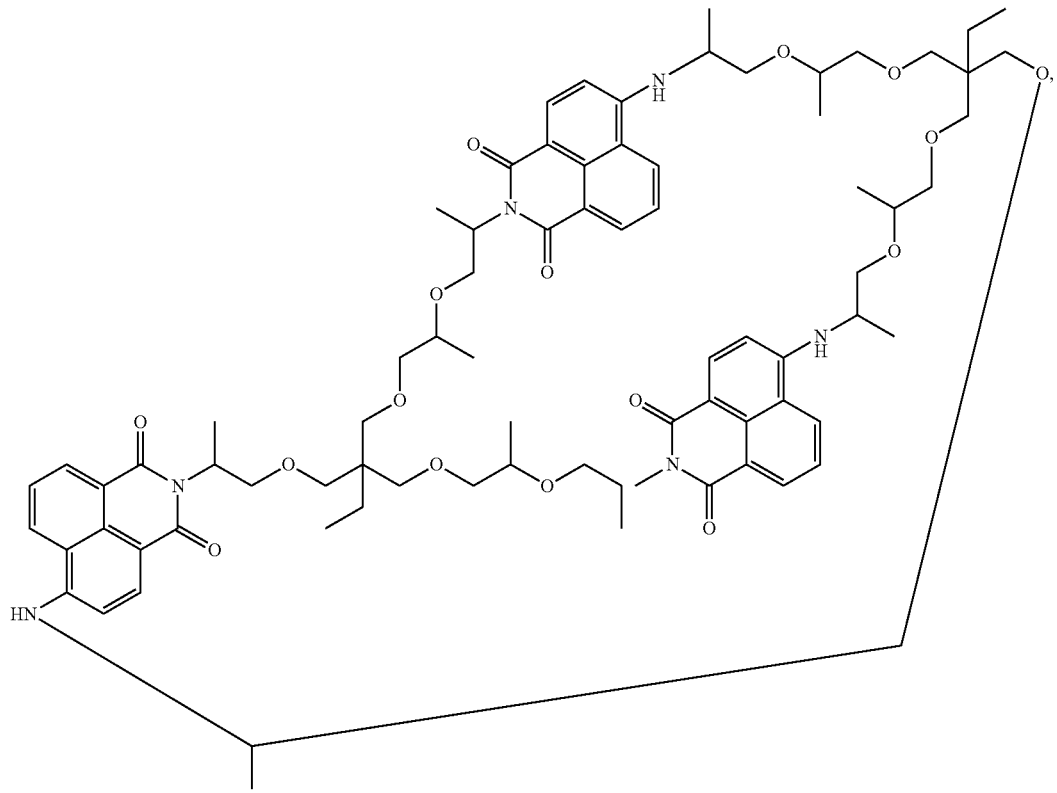 [SMILES: CCCOC(C)COCC1(CC)COCC(C)OCC(C)N2C(=O)c3cccc4c(ccc(c34)C2=O)NC(C)COC(C)COCC(CC)(COCC(C)OCC(C)Nc2ccc3c4c(cccc24)C(=O)N(C)C3=O)COCC(C)Nc2ccc3c4c(cccc24)C(=O)N(C3=O)C(C)COC1]

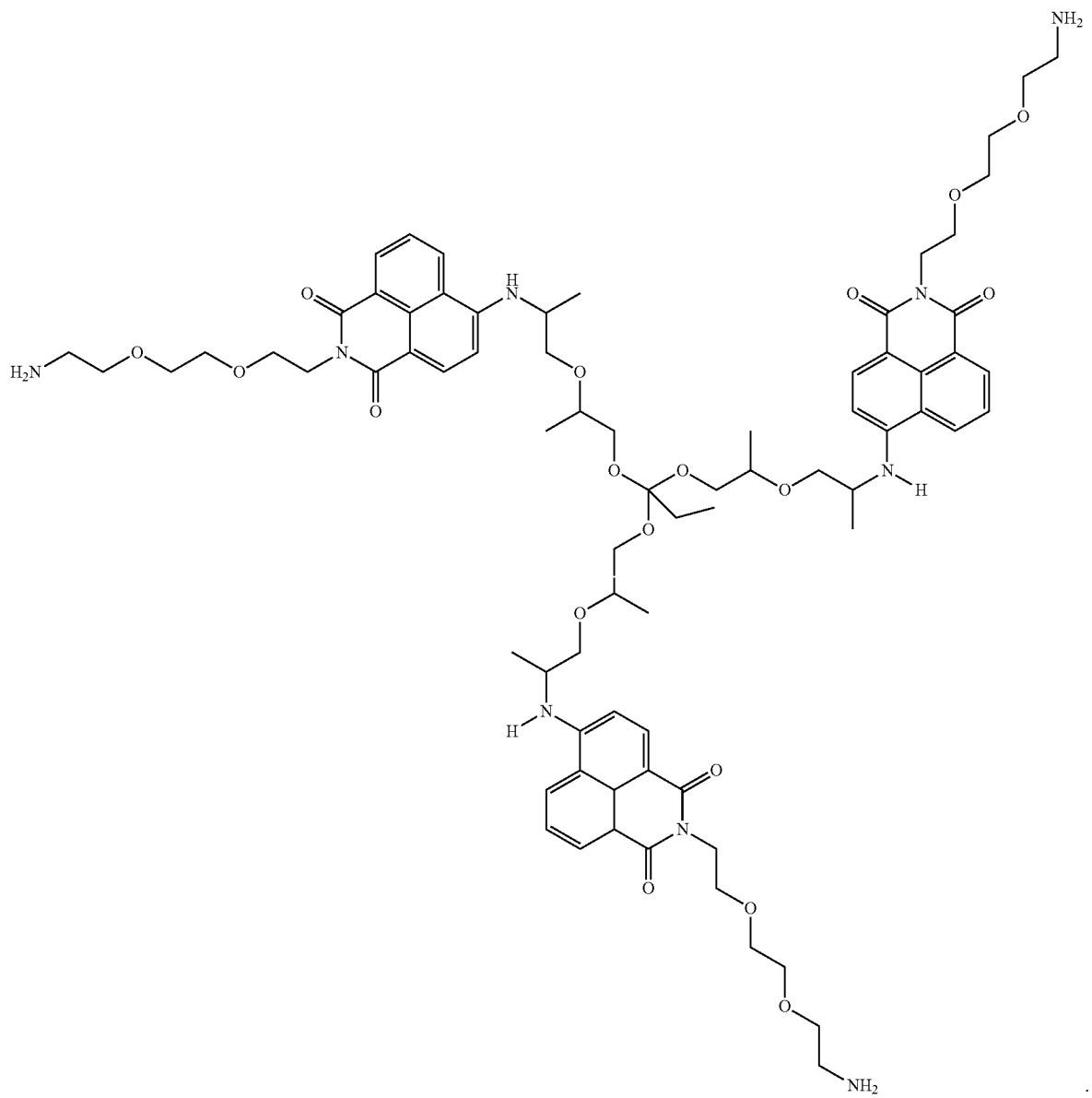 [SMILES: CCC(OCC(C)OCC(C)NC1=CC=C2C(=O)N(CCOCCOCCN)C(=O)C3C=CC=C1C23)(OCC(C)OCC(C)Nc1ccc2c3c(cccc13)C(=O)N(CCOCCOCCN)C2=O)OCC(C)OCC(C)Nc1ccc2c3c(cccc13)C(=O)N(CCOCCOCCN)C2=O]

2. A method of softening plaque in a treatment zone of a blood vessel comprising a plaque matrix; the method comprising:
applying a bolus of a composition comprising the compound of claim 1 to the treatment zone of the blood vessel, wherein the blood vessel is an artery or a vein.

3. The method of claim 2, wherein the compound is applied for a period of time from about 1 second to about 1 hour.

4. The method of claim 2, wherein the plaque matrix comprises lesions ranging in length from about 4 to about 9 cm.

5. The method of claim 2, further comprising activating the compound with a sufficient amount of an activating agent.

6. The method of claim 5, wherein the activating agent is selected from the group consisting of radiated energy, electromagnetic energy, laser, electric current, electrons, thermal neutrons, and chemicals.

7. The method of claim 5, further comprising tacking-up of plaque against a wall of a lumen of a vessel.

8. The method of claim 7, further comprising a step of expanding the vessel lumen having a first diameter, which is smaller than a normal lumen diameter for the vessel at a location adjacent to the isolated section, to a second diameter which is equal to or greater than the normal lumen diameter.

9. The method of claim 7, wherein the second diameter of the lumen comprises a diameter which exceeds the normal diameter by up to thirty percent.

10. The method of claim 7, wherein the lumen diameter is expanded by balloon angioplasty.

11. The method of claim 7, wherein the expanding step is performed at least one of prior to, during, or subsequent to the applying step.

12. A method of producing the compound of claim 1, the method comprising:
combining a first polyetheramine and a boc-anhydride to form a boc-protected polytheramine;

combining a halogen-substituted-1,8-naphthalimide, wherein the halogen is substituted in the 4-position, and the boc-protected polyetheramine to form a 4-halogen-N-Boc-polyetheramine-naphthalimide; and combining the 4-halogen-N-Boc-polyetheramine-naphthalimide with a second polyetheramine to form a reaction product comprising the naphthalimide trimer.

13. The method of claim 12, wherein the first and second polyetheramine are the same or different.

14. A composition comprising the compound of claim 1 dissolved in a solvent.

15. The composition of claim 14, wherein the solvent is selected from the group consisting of phosphate buffered saline, ethanol, dimethylsulfoxide, dimethylformamide, and isopropyl alcohol.

16. The composition of claim 14, wherein the compound is present in the composition at a concentration of about 1 mg/mL.

17. The compound of claim 1, which is

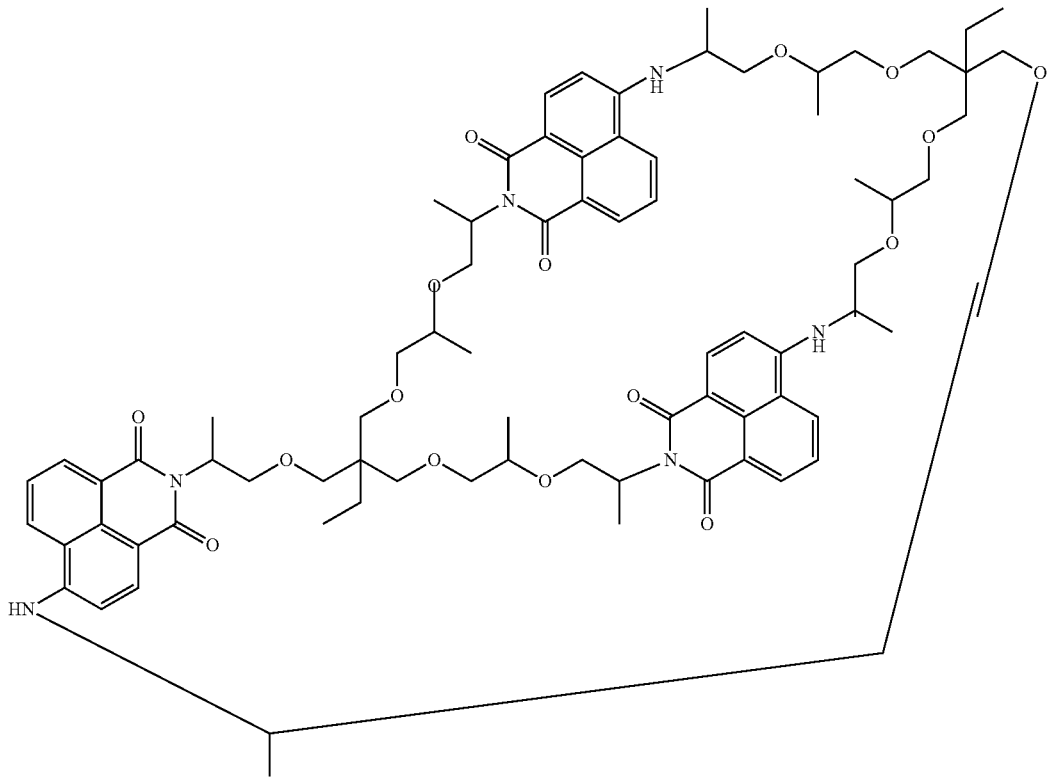

,

18. The compound of claim 1, which is

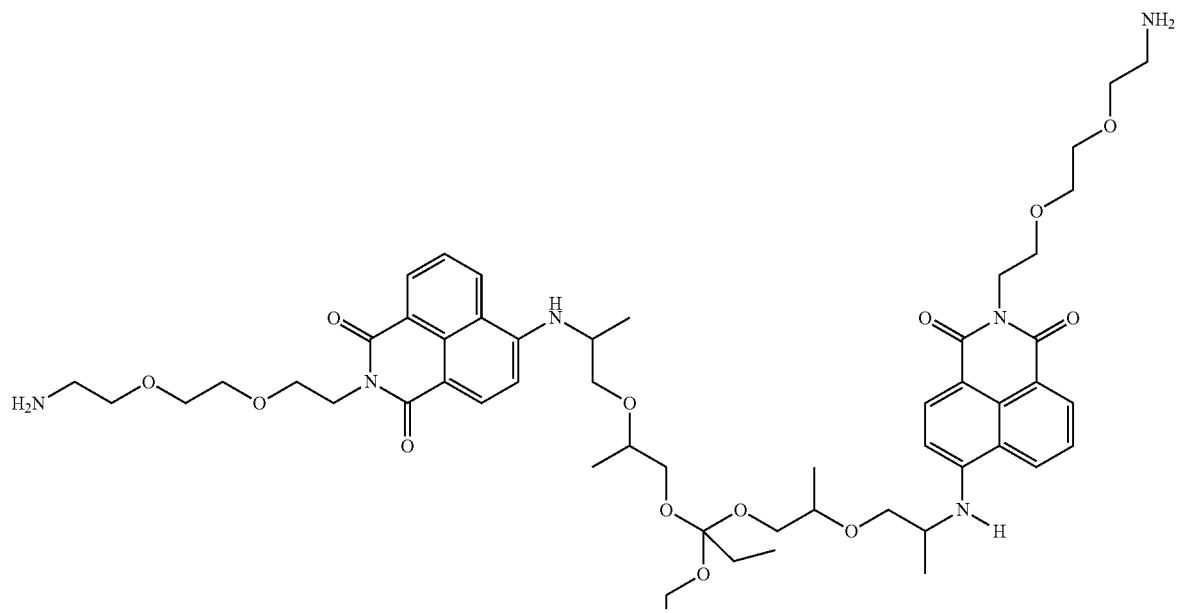

-continued
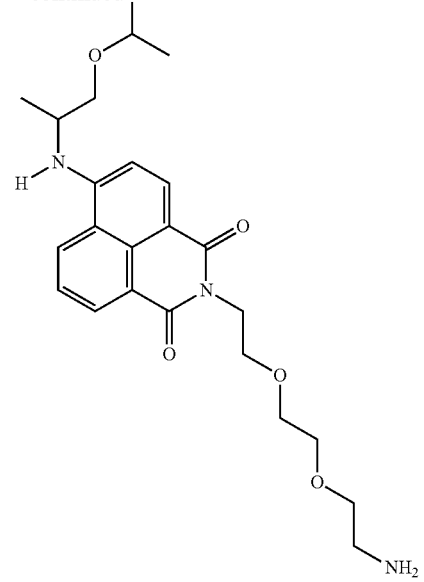
,